(12) United States Patent
Macielag et al.

(10) Patent No.: US 9,815,790 B2
(45) Date of Patent: Nov. 14, 2017

(54) CHEMICALLY MODIFIED QUINOLINE AND QUINOLONE DERIVATIVES USEFUL AS CB-1 INVERSE AGONISTS

(71) Applicant: Janssen Pharmaceutica NV, Beerse (BE)

(72) Inventors: Mark J. Macielag, Gwynedd Valley, PA (US); Yue-Mei Zhang, Wellesley, MA (US); Michael N. Greco, Lansdale, PA (US); Barry A. Springer, Wilmington, DE (US); William V. Murray, Belle Mead, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/239,476

(22) Filed: Aug. 17, 2016

(65) Prior Publication Data

US 2017/0057922 A1    Mar. 2, 2017

Related U.S. Application Data

(60) Provisional application No. 62/210,481, filed on Aug. 27, 2015.

(51) Int. Cl.
*C07D 215/44* (2006.01)
*C07D 401/12* (2006.01)
(52) U.S. Cl.
CPC ......... *C07D 215/44* (2013.01); *C07D 401/12* (2013.01)
(58) Field of Classification Search
None
See application file for complete search history.

(56) References Cited

U.S. PATENT DOCUMENTS

| | | | |
|---|---|---|---|
| 5,968,952 A | 10/1999 | Venet et al. | |
| 6,037,350 A | 3/2000 | Venet et al. | |
| 9,266,835 B2* | 2/2016 | DeCorte | C07D 215/44 |
| 9,464,055 B2* | 10/2016 | DeCorte | C07D 215/44 |
| 2004/0067968 A1 | 4/2004 | Angibaud et al. | |
| 2015/0239845 A1 | 8/2015 | DeCorte et al. | |

OTHER PUBLICATIONS

Kang, Jung Seok. "Emerging PEGylated Drugs", *Expert Opin. Emerging Drugs*,(2009), 14(2) p. 363-380.

Leriche, G. et al. "Cleavable linkers in chemical biology", Bioorg Med Chem, (2012), 20, p. 571-582.
International Search Report for PCT/US2016/047335 dated Oct. 27, 2016.

* cited by examiner

*Primary Examiner* — Brian J Davis
(74) *Attorney, Agent, or Firm* — Thomas J. Dodd

(57) ABSTRACT

Disclosed are compounds, compositions and methods for treating of disorders that are affected by the modulation of the CB1 receptor. Such compounds are represented by Formula (I)

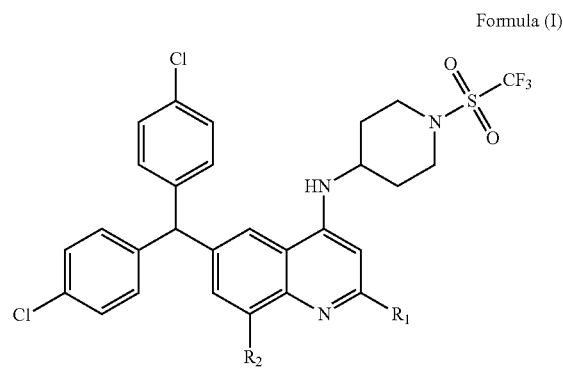

Formula (I)

wherein $R_1$, $R_2$, $R_3$, $L^1$, n, v, r, w, and g are defined herein. and further represented by Formula (II)

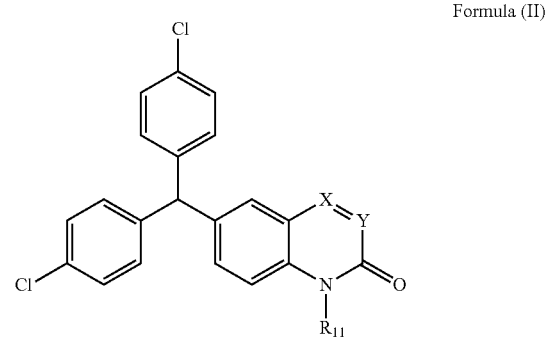

Formula (II)

wherein the group "X═Y", ring A, $R_{10}$, $R_{11}$, $R_{30}$, W, and t are defined herein.

33 Claims, No Drawings

CHEMICALLY MODIFIED QUINOLINE AND QUINOLONE DERIVATIVES USEFUL AS CB-1 INVERSE AGONISTS

CROSS-REFERENCE TO RELATED APPLICATIONS

This application claims the benefit of U.S. Provisional Application 62/210,481, filed on Aug. 27, 2015 which is incorporated by reference herein in its entirety.

FIELD OF THE INVENTION

The present invention relates to chemically modified quinoline and quinolone derivatives and to their use in the treatment of disorders and conditions mediated by the cannabinoid-1 (CB-1) receptor; more particularly, in the treatment of disorders and conditions responsive to inverse agonism of the CB-1 receptor. For example, the compounds of the present invention are useful in the treatment of metabolic disorders.

BACKGROUND OF THE INVENTION

Centrally penetrant cannabanoid-1 receptor (CB1) inverse agonist compounds are efficacious for weight loss, glycemic control and treatment of cardiovascular risk factors associated with obesity and/or Type II diabetes mellitus. However such compounds are also associated serious adverse effects such as anxiety, depression, suicidal ideation, and others, which adverse effects preclude their use. Peripherally restricted cannabanoid-1 receptor (CB1R) inverse agonists aim to selectively inhibit the CB1R in organs/tissues outside the blood-brain barrier, for example in the liver, adipose tissue and/skeletal muscle, to avoid the adverse effects. Thus, there remains a need for peripherally restricted cannabanoid-1 receptor (CB1R) inverse agonists for the treatment of, for example metabolic disorders, such as obesity, Type II diabetes mellitus, and Syndrome X.

The compounds of this invention are peripherally restricted CB1R inverse agonists and represent novel therapeutic agents for the treatment of metabolic disorders such as obesity and Type II diabetes. PEGylation (covalent attachment of a polyethylene glycol polymer) has been used to improve the bioavailability and ease of formulation of small molecule drugs having poor aqueous solubilities. PEGylation may confer beneficial properties on protein, peptide, and small molecule drugs, including extended in vivo half-life, enhanced aqueous solubility, reduced immunogenicity of peptides and proteins, and potentially limited brain penetration.

Thus, PEGylated CB-1 inverse agonists of the present invention may provide therapeutic benefit for the treatment of metabolic disorders such as obesity, Type II diabetes mellitus, and Syndrome X without the adverse effects associated with antagonism of the CB-1 receptor.

PEGylation of small molecule drugs, however, poses distinct challenges. In particular, identification of permissive sites on the small molecule to which the PEG polymer may be attached without loss of biological activity can be difficult. In addition, the high molecular weight (10-40 kDa) and polydisperse nature (range of molecular weights) of commercially available PEGs makes the development of sensitive and robust methods for analysis of the PEG-small molecule conjugate extremely problematic.

To address the problems associated with bioanalysis of PEG-small molecule conjugates, the present invention also includes a linker that is stable in vivo but permits quantitative liberation of a discrete small molecule from the PEG polymer under orthogonal chemical cleavage conditions ex vivo. The small molecule can be analyzed and quantified using conventional methods such as mass spectrometry. The utility of cleavable linker technology in chemical biology has been recently reviewed (*Bioorganic and Medicinal Chemistry* 20 (2012) 571-582).

SUMMARY OF THE INVENTION

The present invention is directed to CB-1 inverse agonists, more particularly quinoline derivatives, compounds of Formula (I)

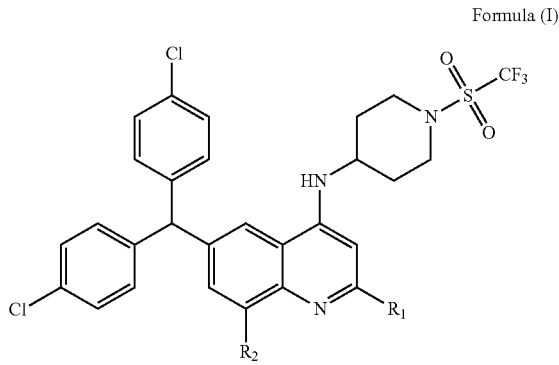

Formula (I)

wherein
$R_1$ and $R_2$ are selected from the group consisting of
i) hydrogen, ii)

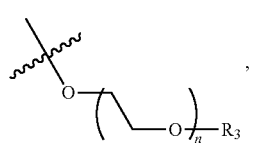

iii)

-continued iv)

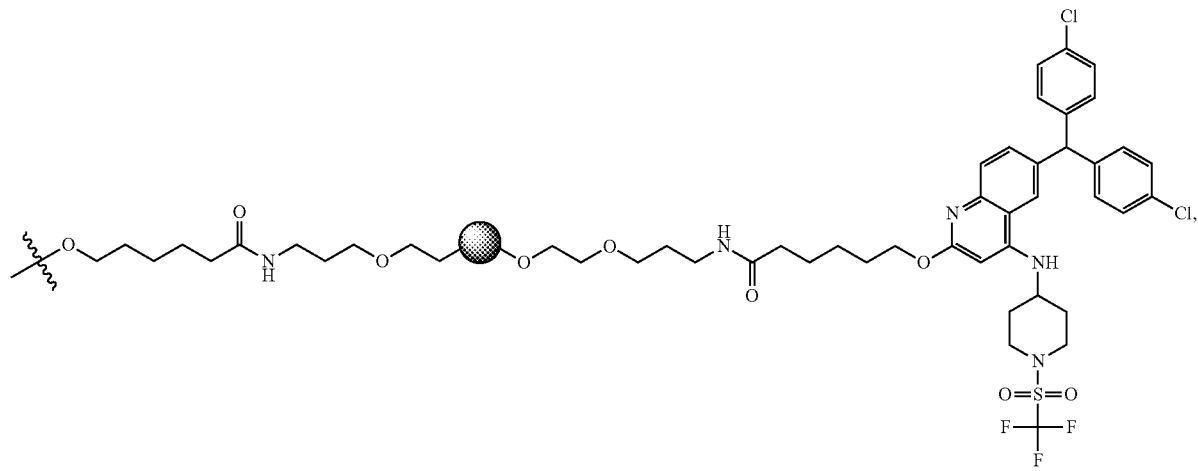

v)

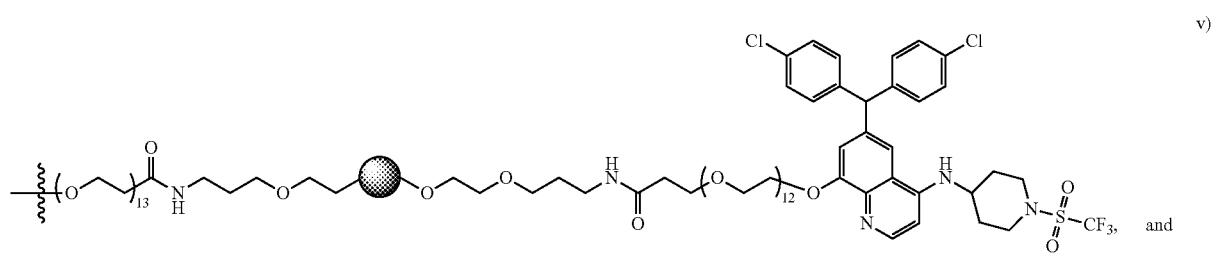
and vi)

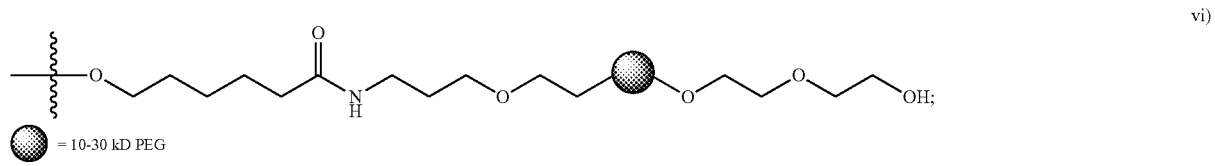

● = 10-30 kD PEG such that one of $R_1$ and $R_2$ is hydrogen in every instance;

$R_3$ is a substituent selected from the group consisting of methyl, $C_{1-4}$ alkoxycarbonylamino-ethyl, $C_{1-4}$ alkoxycarbonyl-ethyl, carboxyethyl, aminoethyl, hydrogen, 4-hydroxymethylphenyl, or a substituent selected from the group consisting of

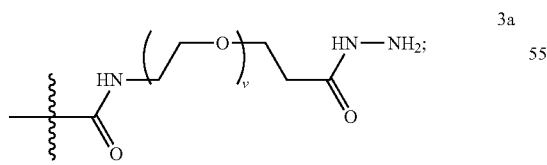
3a

-continued

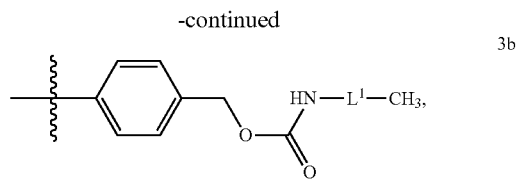
3b wherein $L^1$ is selected from

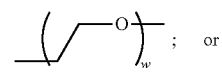
; or

-continued

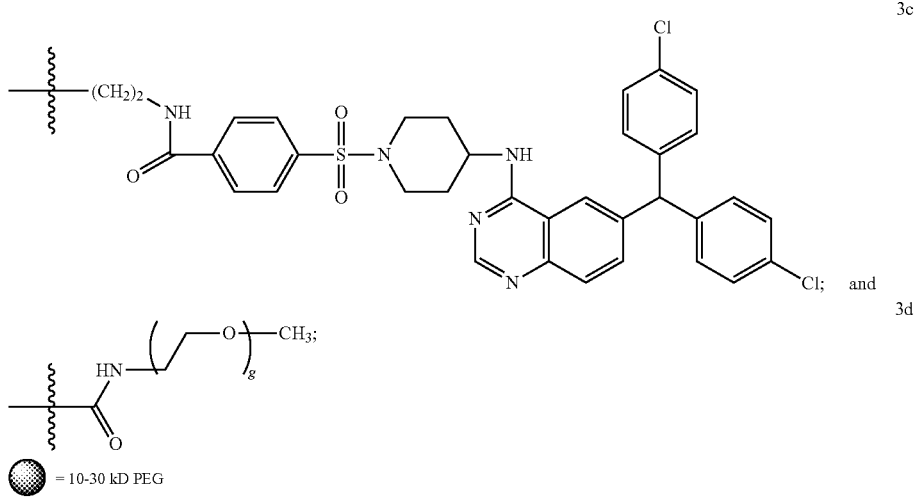

3c

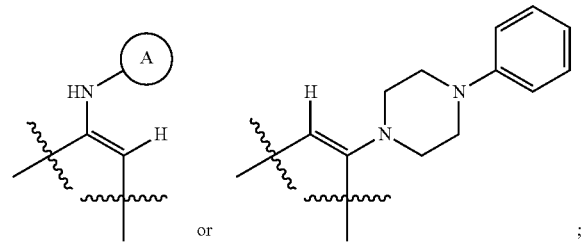

= 10-30 kD PEG n is an integer from 2 to 36;
v is an integer from 1 to 12;
r is an integer from 2 to 7;
w is an integer from 1 to 24;
g is an integer from 1 to 24;

or an enantiomer, diastereomer, or pharmaceutically acceptable salt form thereof.

The present invention is also directed to CB-1 inverse agonists, more particularly quinolone derivatives, of Formula (II)

Formula (II)

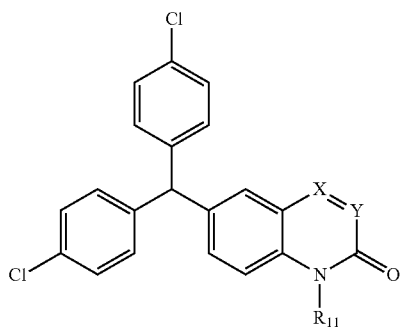

wherein the group "X=Y" is such that when X=Y is

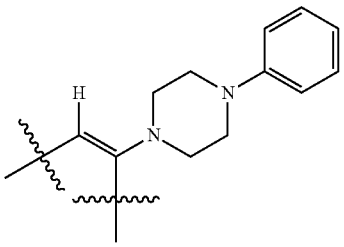

$R_{11}$ is

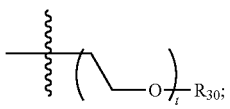

ring A is selected from

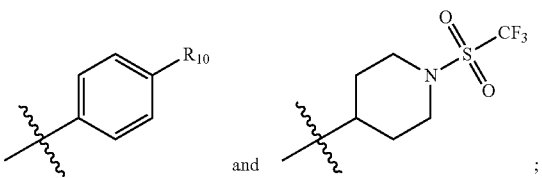

and $R_{10}$ and $R_{11}$ are selected from the group consisting of hydrogen or

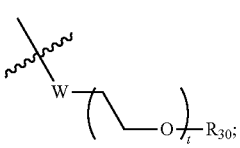

wherein W is O or absent; and such that one of $R_{10}$ and $R_{11}$ is hydrogen in every instance where both $R_{10}$ and $R_{11}$ are present;

$R_{30}$ is a substituent selected from the group consisting of hydrogen, methyl, $C_{1-4}$ alkoxycarbonylamino-ethyl, $C_{1-4}$ alkoxycarbonyl-ethyl, carboxyethyl, aminoethyl, and 4-hydroxymethylphenyl;

t is an integer from 2 to 14;

or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I) or Formula (II), or a pharmaceutically acceptable salt form thereof.

Also provided are processes for making a pharmaceutical composition comprising, consisting of, and/or consisting essentially of admixing a compound of Formula (I) or Formula (II), and a pharmaceutically acceptable carrier, a pharmaceutically acceptable excipient, and/or a pharmaceutically acceptable diluent.

Exemplifying the invention are methods of treating a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain) comprising administering to a subject in need thereof a therapeutically effective amount of any of the compounds or pharmaceutical compositions described above.

The present invention further provides methods for treating or ameliorating a disease, syndrome, or condition in a subject, including a mammal and/or human in which the disease, syndrome, or condition is affected by the inverse agonism of the CB-1 receptor, such as obesity, Type II diabetes mellitus, or Syndrome X, using a compound of Formula (I) or Formula (II).

The present invention also is also directed to the use of any of the compounds described herein in the preparation of a medicament wherein the medicament is prepared for treating a disease or condition that is affected by the inverse agonism of the CB-1 receptor, selected from the group consisting of obesity, Type II diabetes mellitus, and Syndrome X, in a subject in need thereof.

The present invention is also directed to the preparation of PEGylated quinoline and PEGylated quinolone derivatives that act as selective inverse agonists of the CB-1 receptor.

Exemplifying the invention are methods of treating a disorder modulated by CB-1 receptor selected from the group consisting of obesity, Type II diabetes mellitus, and Syndrome X, comprising administering to a subject in need thereof a therapeutically effective amount of any of the compounds or pharmaceutical compositions described above.

In another embodiment, the present invention is directed to a compound of Formula (I) for use in the treatment of a disorder affected by the inverse agonism of CB-1 selected from the group consisting of obesity, Type II diabetes mellitus, and Syndrome X.

In another embodiment, the present invention is directed to a compound of Formula (II) for use in the treatment of a disorder affected by the inverse agonism of CB-1 selected from the group consisting of obesity, Type II diabetes mellitus, and Syndrome X.

In another embodiment, the present invention is directed to a composition comprising a compound of Formula (I) or a compound of Formula (II), for the treatment of a disorder affected by the inverse agonism of CB-1 selected from the group consisting of obesity, Type II diabetes mellitus, and Syndrome X.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}alkyl)_2amino$-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl. The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(=O)OH.
The term "formyl" refers to the group —C(=O)H.
The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

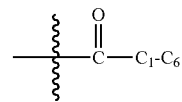

alkyl

One skilled in the art will recognize that the compounds of Formula (II) of the present invention, wherein "X=Y" is

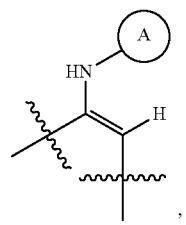

may exist as tautomers. More particularly, the quinolone core, wherein $R_{11}$ is hydrogen, may be present in either of the following keto/enol tautomeric forms or as a mixture of said keto/enol tautomeric forms:

Formula (II) Tautomeric Forms.

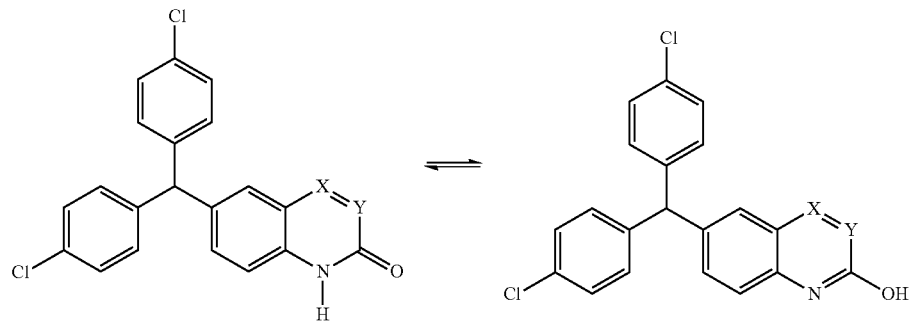

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "CB-1 inverse agonist" is intended to encompass a compound that interacts with CB-1 receptor to substantially decrease its constitutive activity.

The term "CB-1-modulated" is used to refer to the condition of being affected by the modulation of the CB-1 receptor, including but not limited to, the state of being mediated by the CB-1 receptor, for the treatment of a disease or condition such as Type II diabetes.

As used herein, unless otherwise noted, the term "disorder modulated by the CB-1 receptor" shall mean any disease, disorder or condition characterized in that at least one of its characteristic symptoms is alleviated or eliminated upon treatment with a CB-1 receptor inverse agonist. Suitable examples include, but are not limited to obesity, Type II diabetes mellitus, and Syndrome X.

As used herein, unless otherwise noted, the term "affect" or "affected" (when referring to a disease, syndrome, condition or disorder that is affected by inverse agonism of CB-1) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of the instant invention are useful in methods for treating or ameliorating a disease, a syndrome, a condition or a disorder that is affected by the inverse agonism of CB-1 receptor. Such methods comprise, consist of and/or consist essentially of administering to a subject, including an animal, a mammal, and a human in need of such treatment, amelioration and/or prevention, a therapeutically effective amount of a compound of Formula (I) or a compound of Formula (II), or an enantiomer, diastereomer, solvate or pharmaceutically acceptable salt thereof.

In particular, the compounds of Formula (I) and Formula (II), or an enantiomer, diastereomer, solvate or pharmaceutically acceptable salt form thereof are useful for treating or ameliorating diseases, syndromes, conditions, or disorders such as obesity, Type II diabetes mellitus, and Syndrome X.

More particularly, the compounds of Formula (I) and Formula (II), or an enantiomer, diastereomer, solvate or pharmaceutically acceptable salt form thereof are useful for treating or ameliorating Type II diabetes mellitus, comprising administering to a subject in need thereof a therapeutically effective amount of a compound of Formula (I) or a compound of Formula (II), or an enantiomer, diastereomer, solvate or pharmaceutically acceptable salt form thereof as herein defined.

Embodiments of the present invention include a compound of Formula (I)

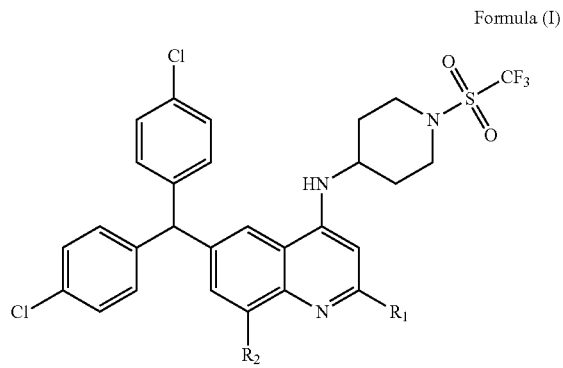

Formula (I)

wherein a) $R_1$ and $R_2$ are selected from the group consisting of
 i) hydrogen, ii)

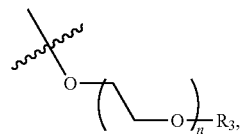

iii)

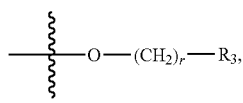

r is an integer from 2 to 5;

iv)
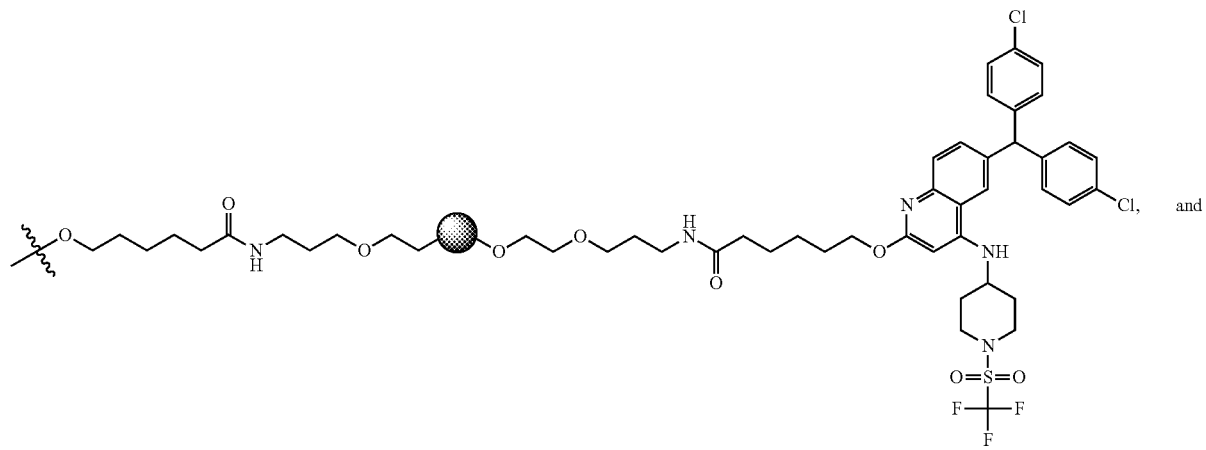
and
v)
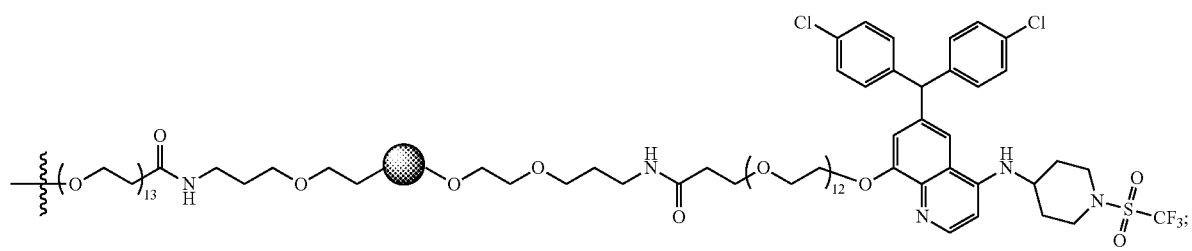
● = 20-30 kD PEG
such that one of $R_1$ and $R_2$ is hydrogen in every instance;
b) $R_1$ and $R_2$ are selected from the group consisting of
  i) hydrogen,
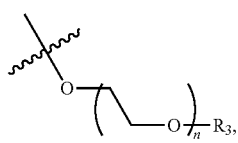
wherein n is an integer selected from the group consisting of
  ii) 3, 4, 6, 7, and 11;
iii)
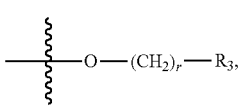
wherein r is 5;

iv)

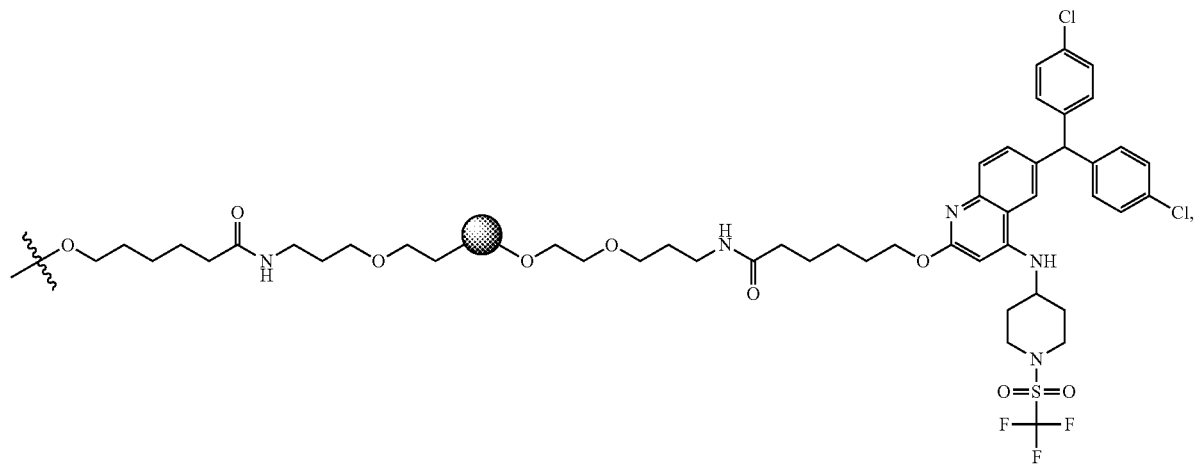

= 20 or 30 kD PEG v)

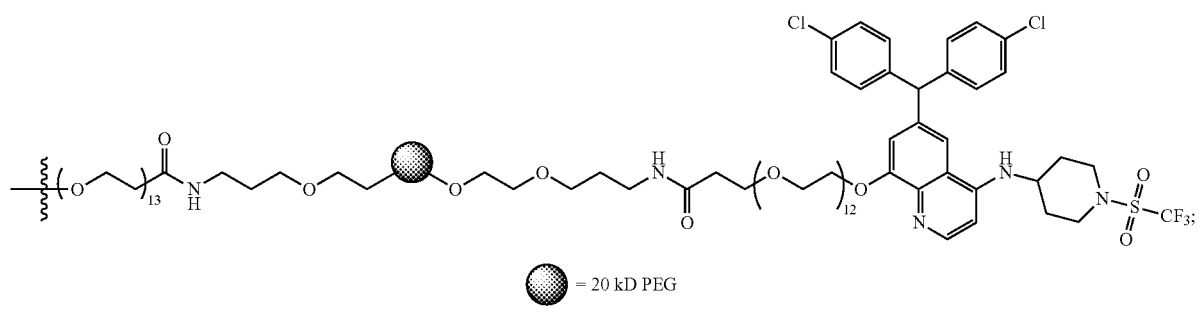

= 20 kD PEG and vi)

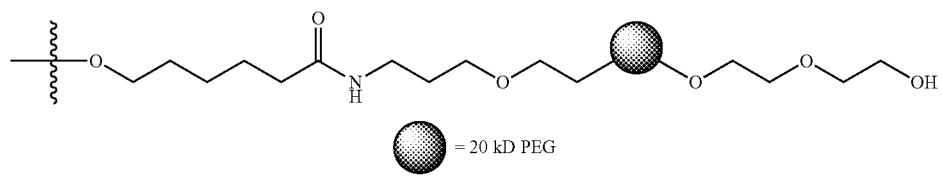

= 20 kD PEG c) $R_3$ is a substituent selected from the group consisting of methyl, carboxyethyl, aminoethyl, hydrogen, 4-hydroxymethylphenyl, or a substituent selected from the group consisting of

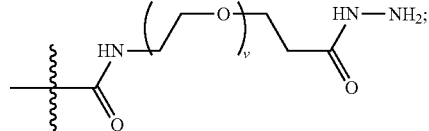

3a

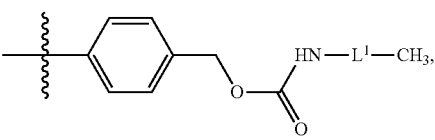

3b wherein $L^1$ is

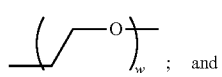

; and

3d d) $R_3$ is a substituent selected from the group consisting of hydrogen, methyl, t-butoxycarbonylamino-ethyl, t-butoxycarbonyl-ethyl, aminoethyl, carboxyethyl, 4-hydroxymethylphenyl, or a substituent selected from the group consisting of 3a 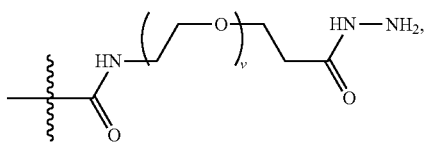

wherein v is 9 or 12;

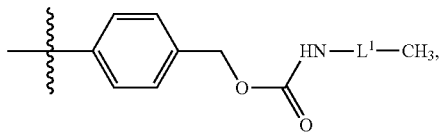

wherein $L^1$ is

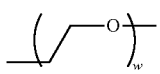

and w is 12;

3c 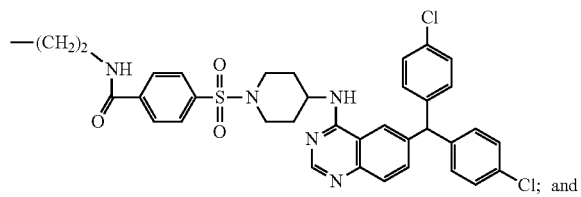

ii)

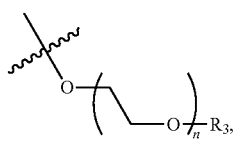

iii)

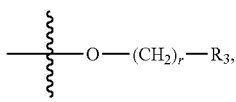

3d 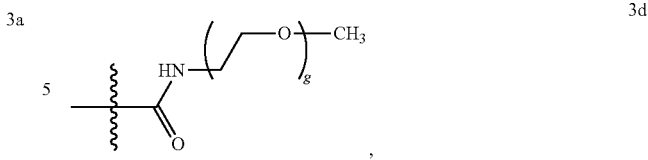

wherein g is 12;
e) n is an integer from 3 to 12;
f) v is an integer from 5 to 12;
g) r is an integer from 5 to 7;
and any combination of embodiments a) through g) above, provided that it is understood that combinations in which different embodiments of the same substituent would be combined are excluded;
or an enantiomer, diastereomer, or pharmaceutically acceptable salt form thereof.

An embodiment of the present invention includes a compound of Formula (I)

Formula (I)

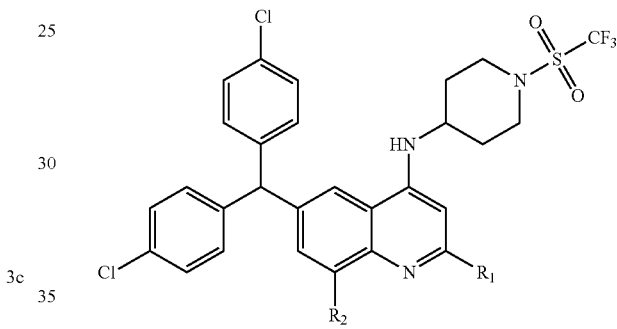

wherein
$R_1$ and $R_2$ are selected from the group consisting of
i) hydrogen, iv)

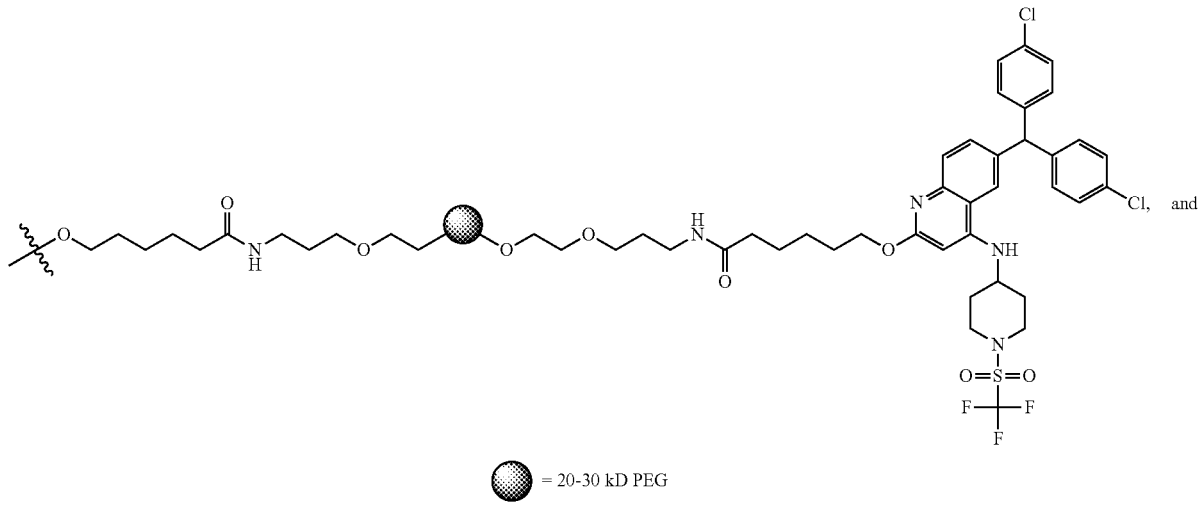

= 20-30 kD PEG v)

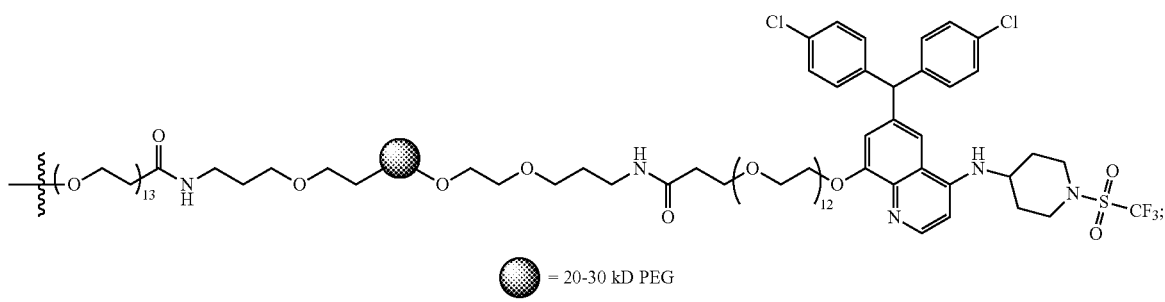

= 20-30 kD PEG such that one of $R_1$ and $R_2$ is hydrogen in every instance;

$R_3$ is a substituent selected from the group consisting of methyl, carboxyethyl, aminoethyl, hydrogen, 4-hydroxymethylphenyl, or a substituent selected from the group consisting of

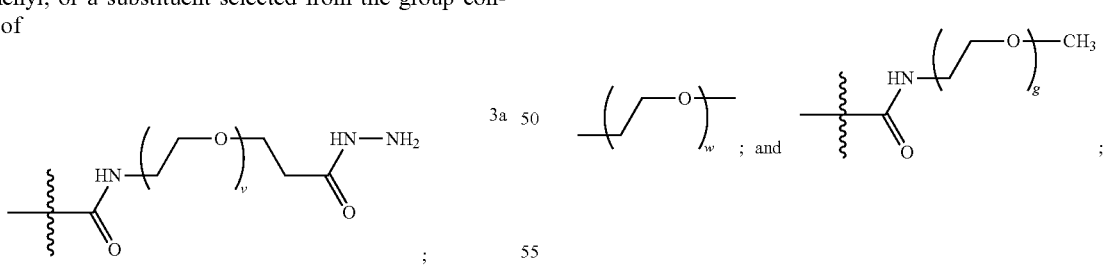

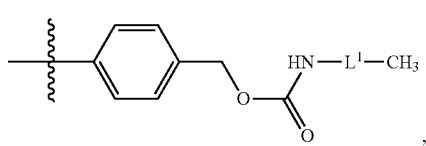

wherein $L^1$ is n is an integer from 3 to 12;
v is an integer from 5 to 12;
r is an integer from 2 to 5;
w is an integer from 1 to 12;
g is an integer from 1 to 12;
or an enantiomer, diastereomer, or pharmaceutically acceptable salt form thereof.

A further embodiment of the present invention includes a compound of Formula (I)

Formula (I)
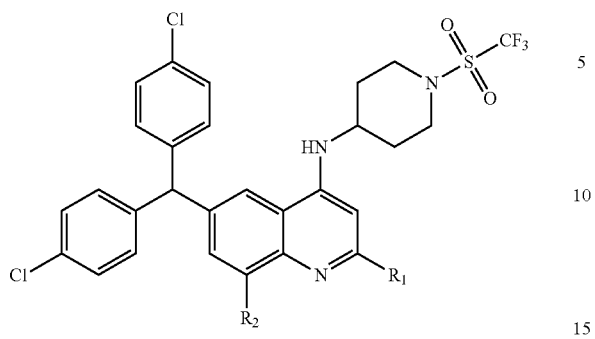
wherein
R$_1$ and R$_2$ are selected from the group consisting of
i) hydrogen,
ii)
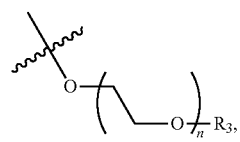
iii)
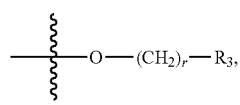
iv)
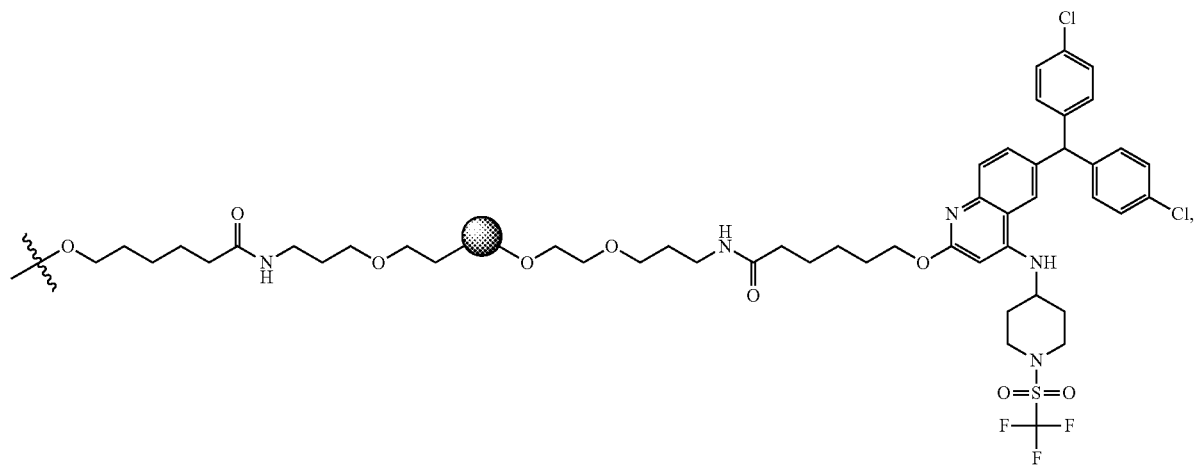
= 20 or 30 kD PEG
v)
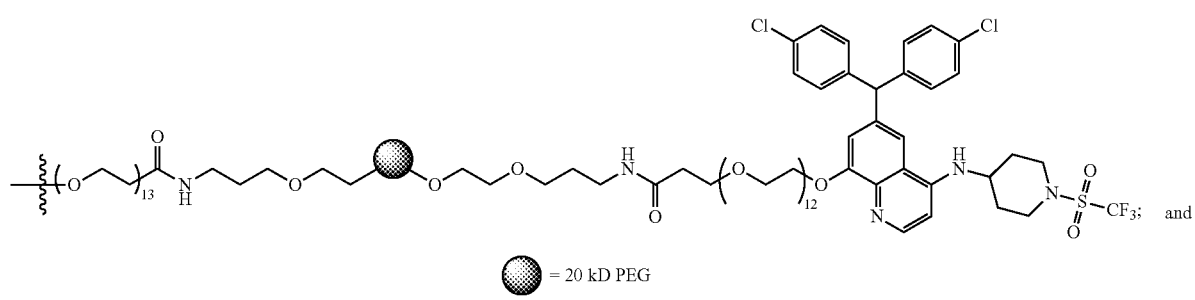
= 20 kD PEG vi)

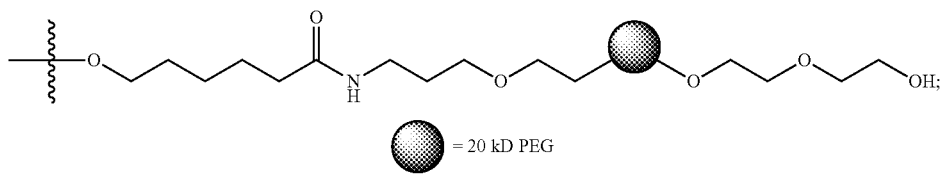

R₃ is a substituent selected from the group consisting of hydrogen, methyl, t-butoxycarbonylamino-ethyl, t-butoxycarbonyl-ethyl, aminoethyl, carboxyethyl, 4-hydroxymethylphenyl, and a substituent selected from the group consisting of

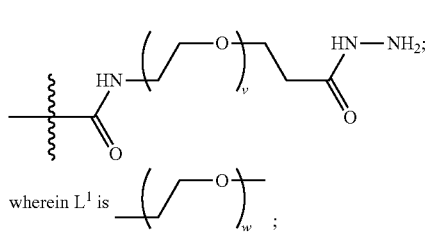

3a

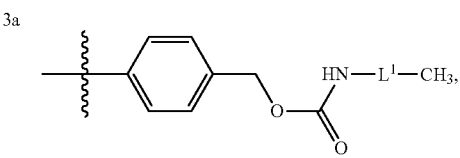

3b

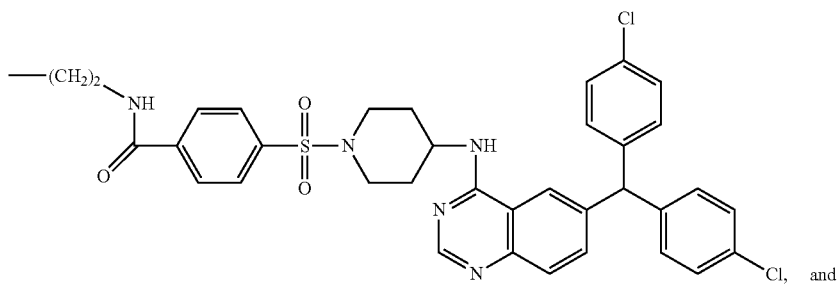

3c

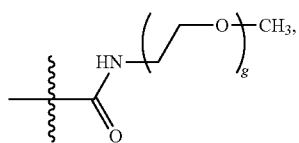

3d n is an integer selected from the group consisting of 3, 4, 6, 7, and 11;
v is 9 or 12;
r is 5;
w is 12;
g is 12;
or an enantiomer, diastereomer, or pharmaceutically acceptable salt form thereof.

Additional embodiments of the present invention include compounds of Formula (I) as herein defined, or an enantiomer, diastereomer, solvate, or a pharmaceutically acceptable salt form thereof, wherein the substituents selected from one or more of the variables defined herein (e.g. $R_1$, $R_2$, $R_3$, $L^1$, n, r, v, w, and g) are independently selected to be any individual substituent or any subset of substituents from those exemplified in the listing in Table 1, below.

TABLE 1
Compounds of Formula (I)
Formula (I)
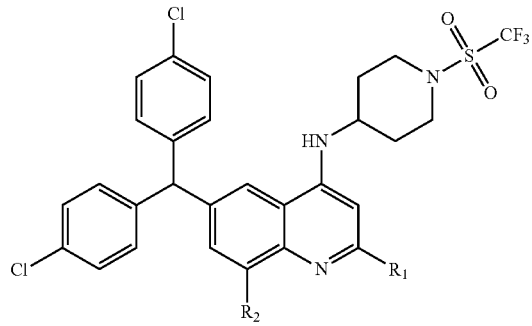
| Cpd No. | R₁ | R₂ | R₃ | n or v |
|---|---|---|---|---|
| 1 | —O—(CH₂CH₂O)ₙ—R₃ | H | methyl | n = 4 |
| 2 | —O—(CH₂CH₂O)ₙ—R₃ | H | methyl | n = 7 |
| 3 | —O—(CH₂CH₂O)ₙ—R₃ | H | t-butoxy carbonylamino-ethyl | n = 11 |
| 4 | —O—(CH₂CH₂O)ₙ—R₃ | H | aminoethyl | n = 11 |
| 5 | —O—(CH₂CH₂O)ₙ—R₃ | H | 3c | n = 11 |
| 6 | —O—(CH₂)ᵣ—R₃ <br> r = 5 | H | 3d <br> g is 12 | — |
| 7 | —O—(CH₂)ᵣ—R₃ <br> r = 5 | H | 3a | v = 9 |

TABLE 1-continued

Compounds of Formula (I)

Formula (I)

| Cpd No. | R₁ | R₂ | R₃ | n or v |
|---|---|---|---|---|
| 8 | –O–(CH₂CH₂O)ₙ–R₃ | H | H | n = 3 |
| 9 | –O–(CH₂CH₂O)ₙ–R₃ | H | H | n = 6 |
| 10 | iv) wherein ● = 20 kD PEG | H | — | — |
| 11 | –O–(CH₂CH₂O)ₙ–R₃ | H | 4-hydroxymethyl phenyl | n = 6 |
| 12 | –O–(CH₂CH₂O)ₙ–R₃ | H | 3a | n = 3, v = 12 |
| 13 | –O–(CH₂CH₂O)ₙ–R₃ | H | 3b | n = 6 |

TABLE 1-continued

Compounds of Formula (I)

Formula (I)

[Structure: quinoline core with bis(4-chlorophenyl)methyl substituent, an HN-linked piperidine bearing N-SO₂CF₃, and R₁, R₂ substituents on the quinoline]

| Cpd No. | R₁ | R₂ | R₃ | n or v |
|---|---|---|---|---|
| | | | $L^1$ is $-\!\!\left(\!\!\diagup\!\!-\!\!O\!\right)_{\!w}\!\!-$ ; w is 12 | |
| 14 | iv) wherein ● = 30 kD PEG | H | — | — |
| 15 | H | [structure: —O—(CH₂CH₂O)ₙ—R₃] | H | n = 10 |
| 16 | H | [structure: —O—(CH₂CH₂O)ₙ—R₃] | t-butoxy carbonyl-ethyl | n = 12 |
| 17 | H | [structure: —O—(CH₂CH₂O)ₙ—R₃] | carboxyethyl | n = 12 |
| 18 | H | iv) wherein ● = 20 kD PEG | — | — |
| 19 | vi) | H | — | — |

Embodiments of the present invention also include a compound of Formula (II)

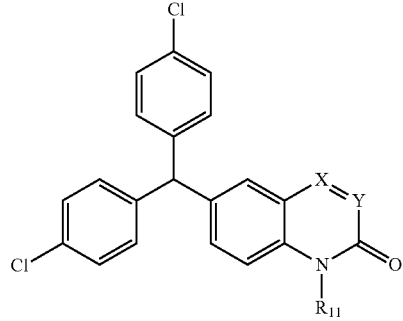

Formula (II)

wherein
a) the group "X=Y" is

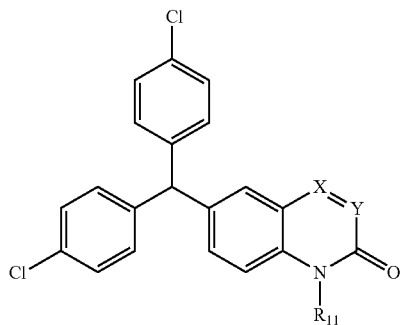

Formula (II)

wherein
the group "X=Y" is

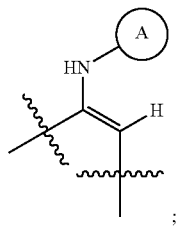

;

ring A is

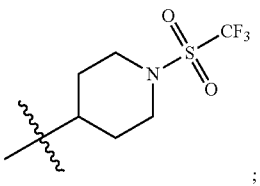 [SMILES: *C1CCN(S(=O)(=O)C(F)(F)F)CC1]

;

$R_{11}$ is

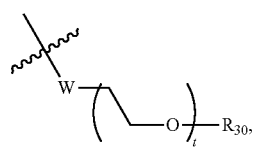

wherein W is absent;
$R_{30}$ is a substituent selected from the group consisting of methyl and $C_{1-4}$alkoxycarbonylamino-ethyl;
t is an integer from 2 to 11;
or an enantiomer, diastereomer, or pharmaceutically acceptable salt form thereof.

Additional embodiments of the present invention include compounds of Formula (II) as herein defined, or an enantiomer, diastereomer, solvate, or a pharmaceutically acceptable salt form thereof, wherein the substituents selected from one or more of the variables defined herein (e.g. X=Y, A, $R_{10}$, $R_{11}$, $R_{30}$, and t) are independently selected to be any individual substituent or any subset of substituents from those exemplified in the listing in Table 2, below.

b) ring A is

;

c) $R_{30}$ is a substituent selected from the group consisting of methyl and $C_{1-4}$alkoxycarbonylamino-ethyl;
d) t is an integer from 2 to 11;

and any combination of embodiments a) through d) above, provided that it is understood that combinations in which different embodiments of the same substituent would be combined are excluded; or an enantiomer, diastereomer, or pharmaceutically acceptable salt form thereof.

Further embodiments of the present invention include a compound of Formula (II)

TABLE 2

Compounds of Formula (II)

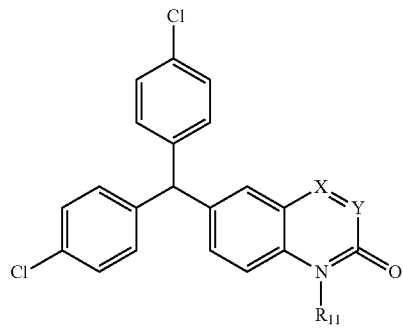

Formula (II)

| Cpd No. | X = Y | A | R₁₀ | R₁₁ | R₃₀ | t |
|---|---|---|---|---|---|---|
| 20 | HN-A (vinyl linkage) | phenyl-R₁₀ | W-(CH₂CH₂O)ₜ-R₃₀, W=O | H | methyl | 2 |
| 21 | HN-A (vinyl linkage) | piperidine-N-SO₂CF₃ | — | W-(CH₂CH₂O)ₜ-R₃₀, W=absent | — | methyl | 4 |
| 22 | HN-A (vinyl linkage) | piperidine-N-SO₂CF₃ | — | W-(CH₂CH₂O)ₜ-R₃₀, W=absent | — | methyl | 7 |
| 23 | HN-A (vinyl linkage) | piperidine-N-SO₂CF₃ | — | W-(CH₂CH₂O)ₜ-R₃₀, W=absent | — | t-butoxycarbonyl-aminoethyl | 11 |
| 24 | N-phenylpiperazinyl vinyl | — | — | W-(CH₂CH₂O)ₜ-R₃₀, W=absent | — | methyl | 4 |

For use in medicine, salts of compounds of Formula (I) and Formula (II) refer to non-toxic "pharmaceutically acceptable salts." Other salts may, however, be useful in the preparation of compounds of Formula (I) and Formula (II) or of their pharmaceutically acceptable salt forms thereof. Suitable pharmaceutically acceptable salts of compounds of Formula (I) and Formula (II) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I) and Formula (II). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I) and Formula (II).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) or Formula (II) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) or Formula (II) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) or Formula (II) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) and Formula (II) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) and Formula (II) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) and Formula (II) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or Formula (II) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 5 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) or Formula (II) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I) or Formula (II).

Advantageously, a compound of Formula (I) may be administered in a single daily dose, or the total daily dosage may be administered in divided doses of two, three and four times daily.

Optimal dosages of a compound of Formula (I) or Formula (II) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) or Formula (II) may be administered in any of the foregoing compositions and dosage regimens or by means of those compositions and dosage regimens established in the art whenever use of a compound of Formula (I) or Formula (II) is required for a subject in need thereof.

As CB-1 inverse agonists, the compounds of Formula (I) and Formula (II) are useful in methods for treating or preventing a disease, a syndrome, a condition or a disorder in a subject, including an animal, a mammal and a human in which the disease, the syndrome, the condition or the disorder is affected by the modulation, including inverse agonism, of the CB-1 receptor. Such methods comprise, consist of and/or consist essentially of administering to a subject, including an animal, a mammal, and a human, in need of such treatment or prevention, a therapeutically effective amount of a compound, salt or solvate of Formula (I) or Formula (II).

In another embodiment, the present invention is directed to a compound of Formula (I) or Formula (II) for use in the treatment of a disorder affected by the inverse agonism of CB-1 receptor selected from the group consisting of obesity, Type II diabetes mellitus, and Syndrome X; preferably, Type II diabetes mellitus.

The compounds of Table 3, exemplified hereinbelow, were prepared according to the schemes and examples provided herein.

TABLE 3

| Cpd No. | Structure |
|---|---|
| 1 | 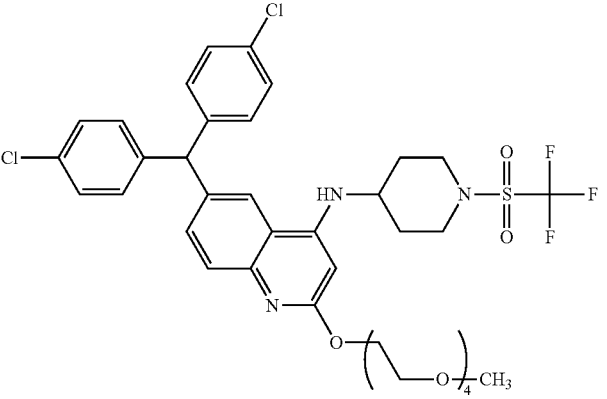 |
| 2 | 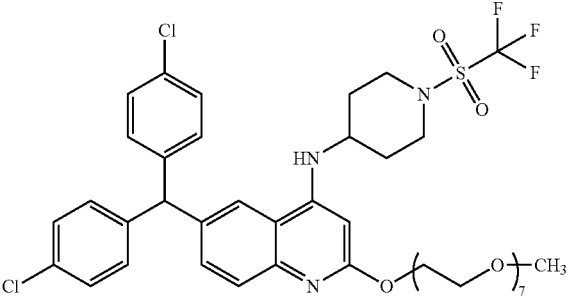 |
| 3 | 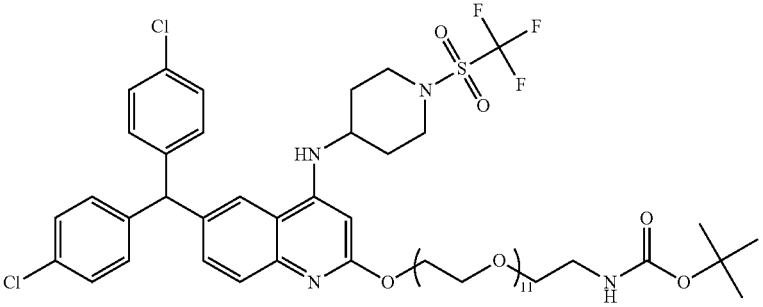 |

TABLE 3-continued

| Cpd No. | Structure |
|---|---|
| 4 | 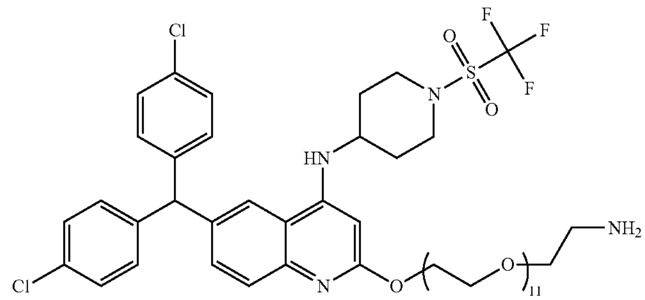 |
| 5 | 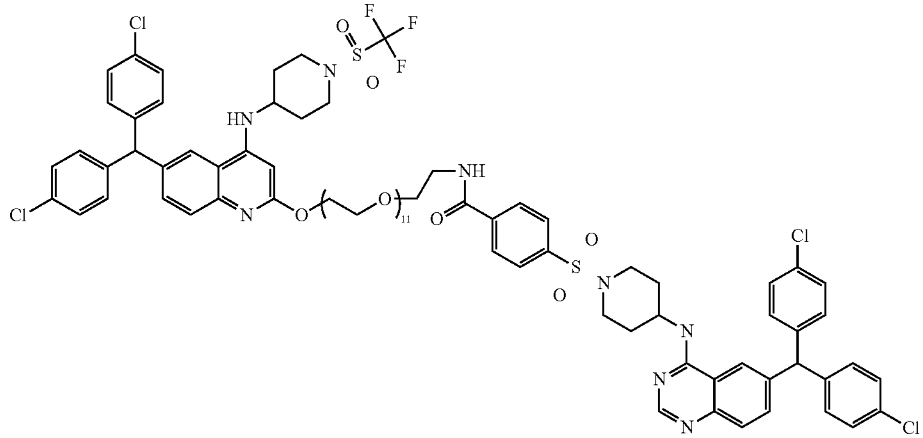 |
| 6 | 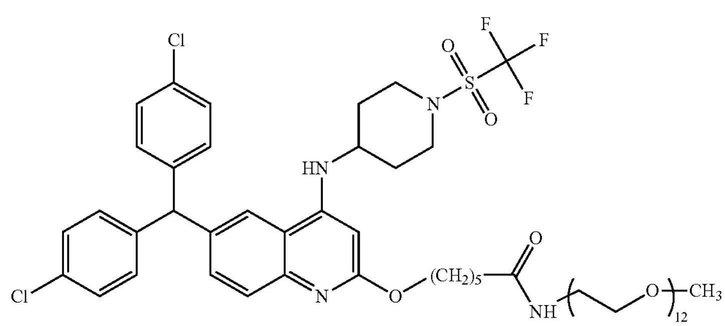 |
| 7 | 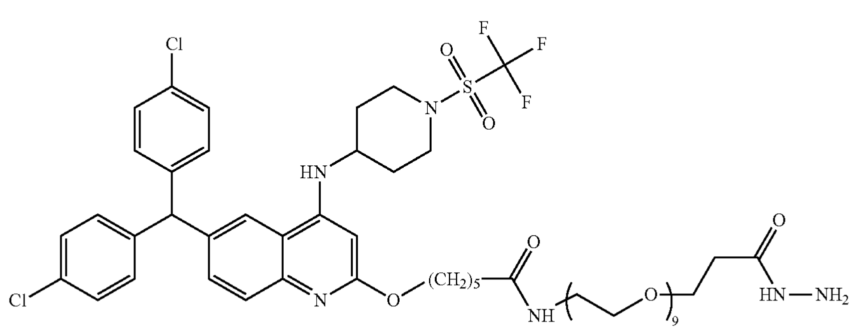 |

TABLE 3-continued

| Cpd No. | Structure |
|---|---|
| 8 | (chemical structure: 6-(bis(4-chlorophenyl)methyl)quinoline with 4-NH-(1-(trifluoromethylsulfonyl)piperidin-4-yl) and 2-O-(triethylene glycol)-OH) |
| 9 | (chemical structure: 6-(bis(4-chlorophenyl)methyl)quinoline with 4-NH-(1-(trifluoromethylsulfonyl)piperidin-4-yl) and 2-O-(hexaethylene glycol)-OH) |
| 10 | (chemical structure: dimeric quinoline compound linked via amide-PEG-20 kD PEG-PEG-amide linker)<br><br>● = 20 kD PEG |
| 11 | (chemical structure: 6-(bis(4-chlorophenyl)methyl)quinoline with 4-NH-(1-(trifluoromethylsulfonyl)piperidin-4-yl) and 2-O-(pentaethylene glycol)-O-(4-hydroxymethyl)phenyl) |
| 12 | (chemical structure: 6-(bis(4-chlorophenyl)methyl)quinoline with 4-NH-(1-(trifluoromethylsulfonyl)piperidin-4-yl) and 2-O-(CH$_2$CH$_2$O)$_3$-C(O)-NH-(CH$_2$CH$_2$O)$_{12}$-C(O)-NH-NH$_2$ hydrazide) |

TABLE 3-continued

| Cpd No. | Structure |
|---|---|
| 13 | 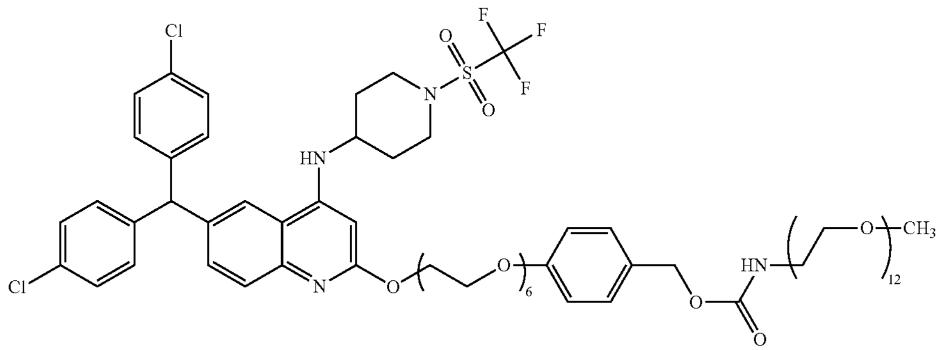 |
| 14 | ● = 30 kD PEG |
| 15 | 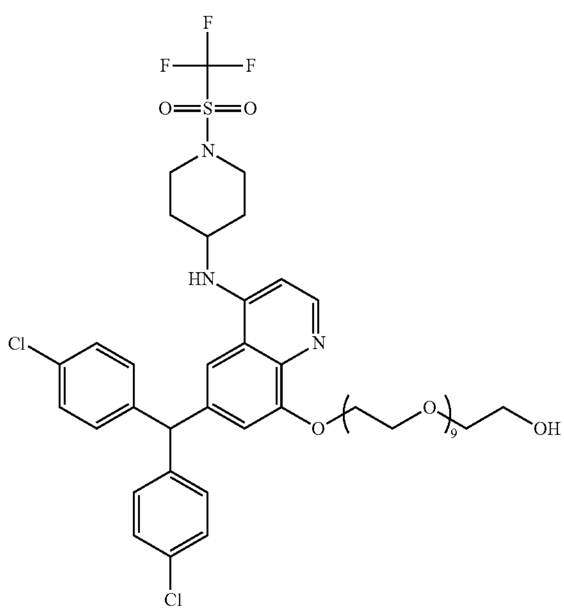 |

TABLE 3-continued
| Cpd No. | Structure |
| --- | --- |
| 16 | 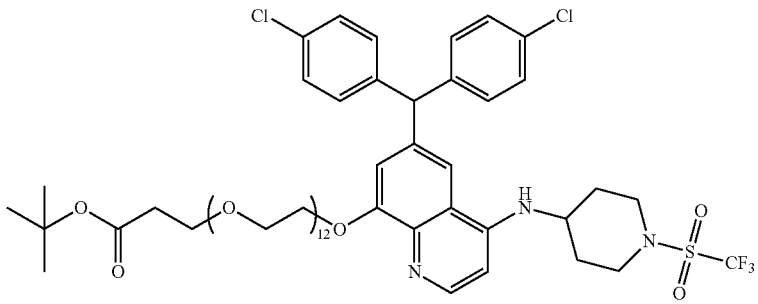 |
| 17 | 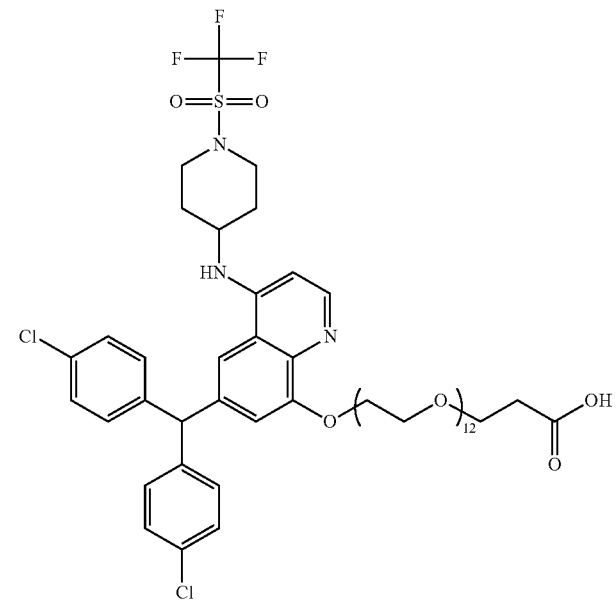 |
| 18 | 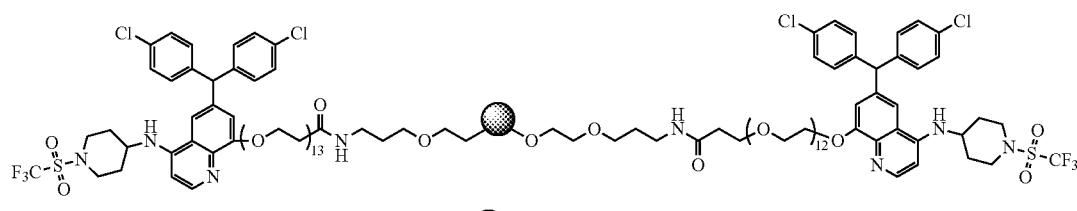 |

TABLE 3-continued

| Cpd No. | Structure |
|---------|-----------|
| 19 | [Chemical structure with ● = 20 kD PEG] |
| 20 | [Chemical structure] |
| 21 | [Chemical structure] |

TABLE 3-continued
| Cpd No. | Structure |
|---|---|
| 22 | 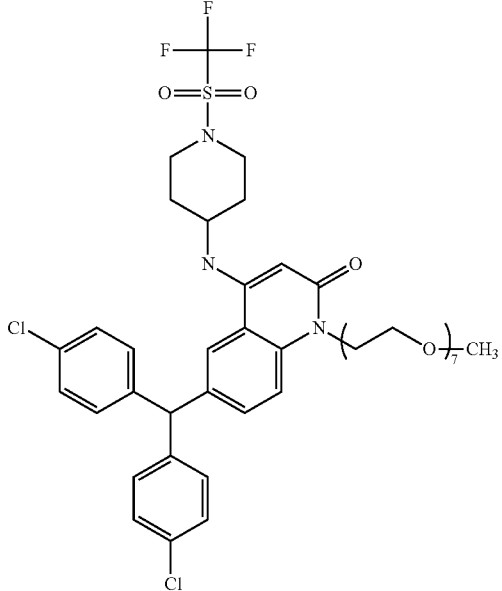 |
| 23 | 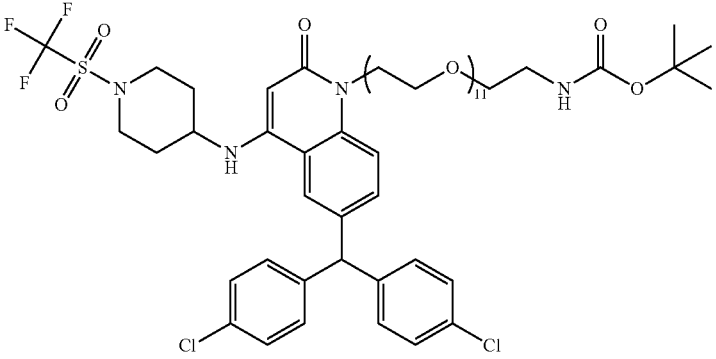 |
| 24 | 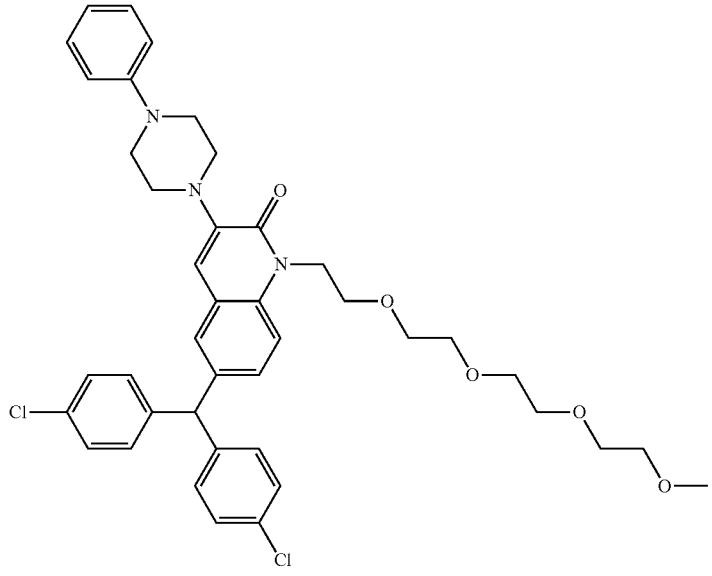 [SMILES: COCCOCCOCCOCCn1c(=O)c(N2CCN(c3ccccc3)CC2)cc2cc(C(c3ccc(Cl)cc3)c3ccc(Cl)cc3)ccc21] |

GENERAL SYNTHETIC METHODS

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. The various starting materials used in the schemes and examples are commercially available or may be prepared by methods well within the skill of persons versed in the art. The variables are as defined herein.

Abbreviations used in the instant specification, particularly the schemes and examples, are as follows:
ACN acetonitrile
aq. aqueous
Bn or Bzl benzyl
Boc tert-butyloxycarbonyl
conc. concentrated
DCE 1,2-dichloroethane
DCM dichloromethane
DIPEA or DIEA diisopropyl-ethyl amine
DMA dimethylaniline
DMAP 4-dimethylaminopyridine
DME dimethoxyethane
DMF N,N-dimethylformamide
DMSO dimethylsulfoxide
EA ethyl acetate
ESI electrospray ionization
EtOAc or EA ethyl acetate
EtOH ethanol
h or hr(s) hour or hours
HPLC high performance liquid chromatography
MeOH methanol
MHz megahertz
min minute or minutes
MS mass spectrometry
Ms methanesulfonyl
NMR nuclear magnetic resonance
RP reverse-phase
rt or RT room temperature
$R_t$ retention time
Sec second or seconds
TEA or $Et_3N$ triethylamine
TFA trifluoroacetic acid
THF tetrahydrofuran
TLC thin layer chromatography
TMS tetramethylsilane
Ts 4-toluenesulfonyl General Schemes Scheme A illustrates the preparation of certain compounds of the present invention.

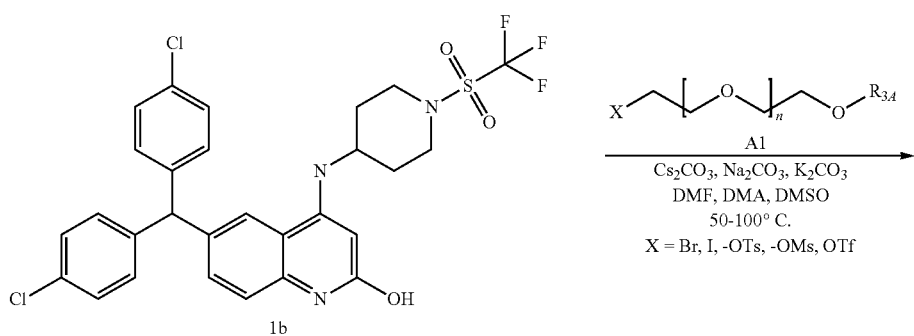

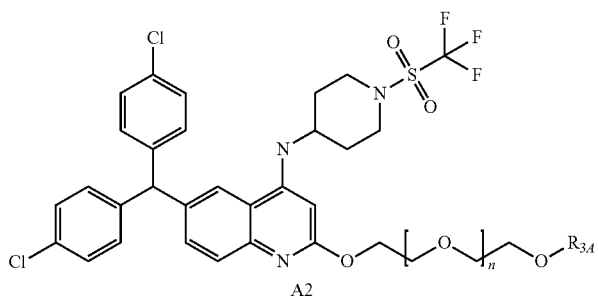

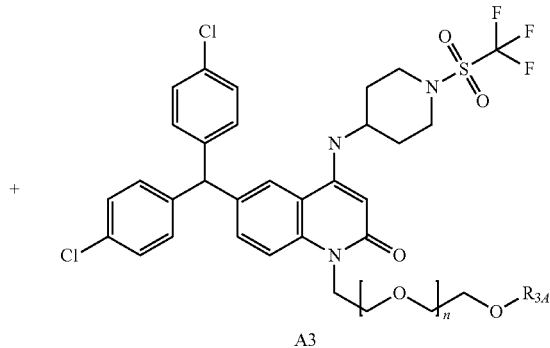

Compound 1b may be treated with an activated PEG methyl ether of formula A1 (wherein X may be bromo, iodo, tosylate, mesylate, or the like; and n is an integer of 1 to 24; and $R_{3A}$ is selected from hydrogen, methyl, $C_{1-4}$alkoxycarbonylamino-ethyl, or $C_{1-4}$alkoxycarbonyl-ethyl) in the presence of a base such as potassium carbonate, sodium carbonate, cesium carbonate, DIEA, and the like, at a temperature of from about 50° C. to about 100° C. to afford a mixture of PEGylated compounds of formula A2 and A3 of the present invention.

Scheme B illustrates the preparation of certain compounds of Formula (I) of the present invention.

Scheme B

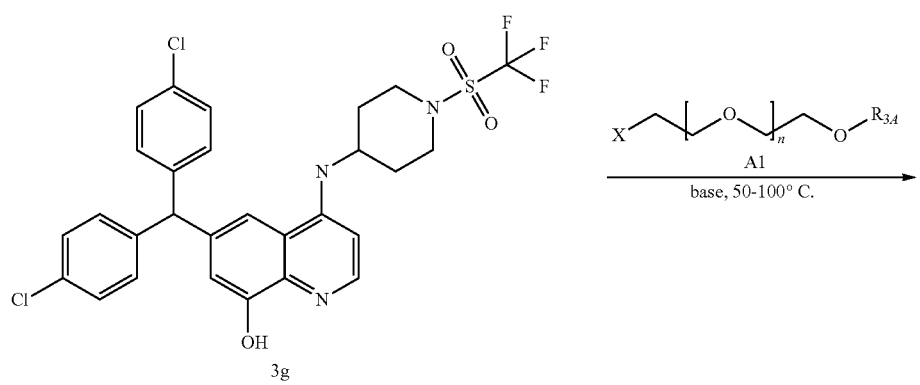

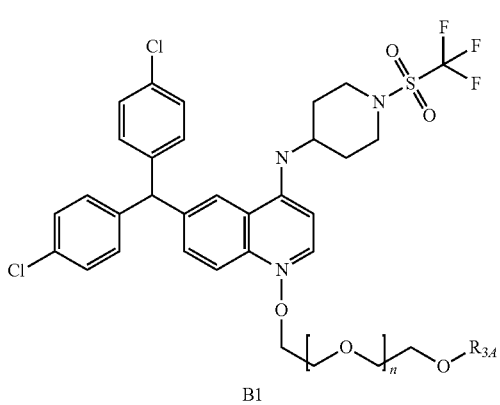

Compound 3g may be treated with the activated PEG reagent of formula A1 in the presence of a base such as potassium carbonate, sodium carbonate, cesium carbonate, DMF, DMA, DMSO, and the like, at a temperature of from about 50° C. to about 100° C. to afford a PEGylated compound of formula B1.

Scheme C illustrates the preparation of certain compounds of Formula (I) of the present invention.

Scheme C

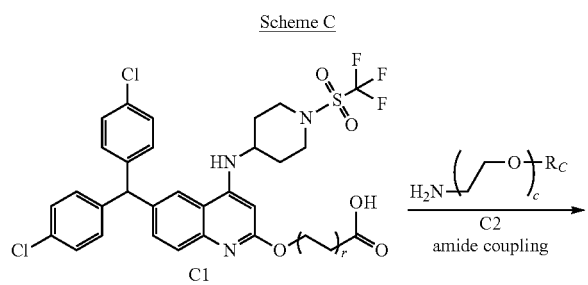

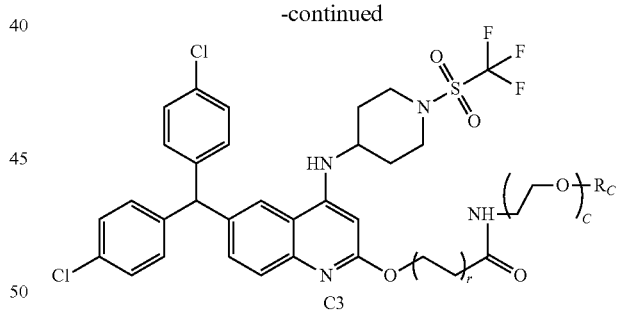

-continued

A compound of formula C1 may be coupled, using conventional coupling conditions for amide formation, with an amine of formula C2 (wherein C may be an integer from 1 to 24, and $R_C$ is methyl or an amino-protected —$(CH_2)_2C(O)NHNH_2$ substituent); in the presence of a base such as triethylamine, diisopropylethylamine, potassium carbonate, sodium carbonate, cesium carbonate, in a suitable solvent such as DMF, DMA, DMSO, a mixture of DMF and dichloromethane, and the like, at a temperature of from about room temperature to about 100° C. to afford a PEGylated compound of formula C3.

Scheme D illustrates the preparation for certain compounds of Formula (I) of the present invention.

Scheme D

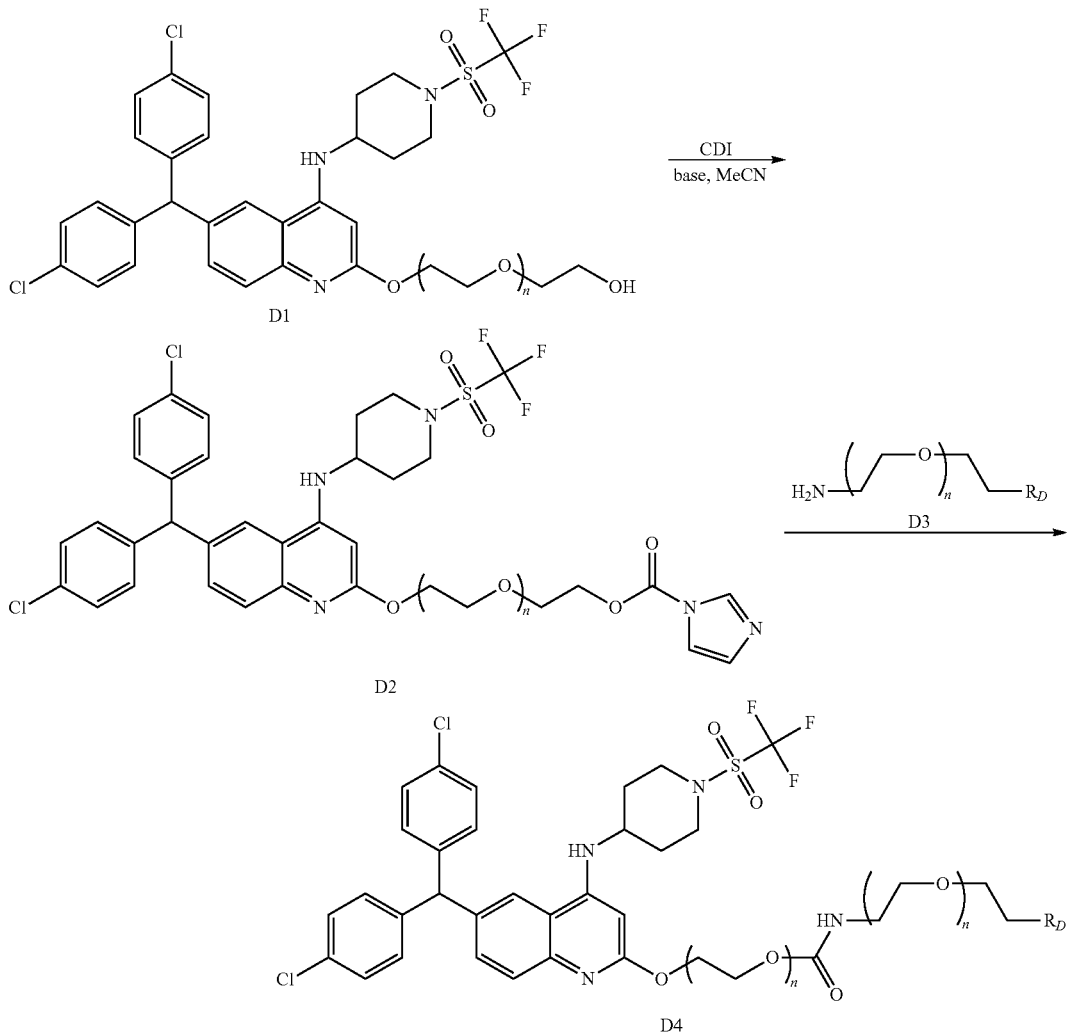

A compound of formula D1 may be treated with a coupling agent such as CDI or the like, in the presence of an organic base such as DIEA or TEA, in an organic solvent such as THF, dioxane, acetonitrile, or the like, to afford a compound of formula D2. A compound of formula D2 may be reacted with an amine of formula D3 (wherein $R_D$ is an $R_3$ terminus, such as methoxy or an amino-protected —C(O)NHNH$_2$ substituent) in a solvent such as acetonitrile, THF, dioxane, DCM, or the like, to afford a compound of formula D4.

Scheme E illustrates the preparation for certain compounds of Formula (I) of the present invention wherein one of $R_1$ and $R_2$ is selected from (iv) and (v).

Scheme E

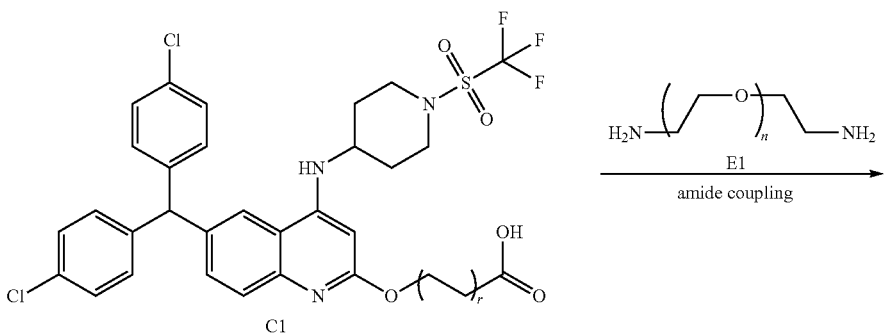

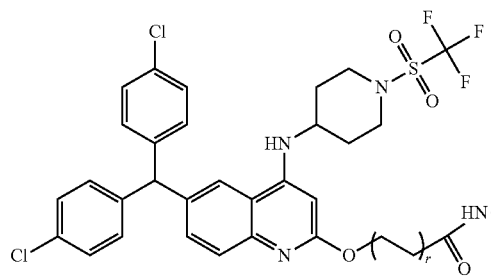
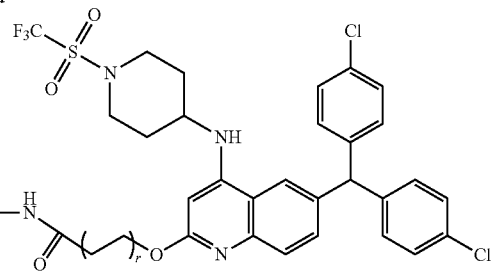

E2

A compound of formula C1 may be coupled, using conventional coupling conditions for amide formation, with a diamine of formula E1 (wherein n may be an integer from 1 to 24); in the presence of a base such as triethylamine, diisopropylethylamine, potassium carbonate, sodium carbonate, cesium carbonate, in a suitable solvent such as DMF, DMA, DMSO, a mixture of DMF and dichloromethane, and the like, at a temperature of from about room temperature to about 100° C. to afford a dimeric PEGylated compound of formula E2.

SPECIFIC EXAMPLES

The following Examples are set forth to aid in the understanding of the invention, and are not intended and should not be construed to limit in any way the invention set forth in the claims which follow thereafter.

In the specific examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example A: Synthesis of Intermediate (4-bromo-2-(tert-butoxy)quinolin-6-yl)(4-chlorophenyl)methanone, 1a

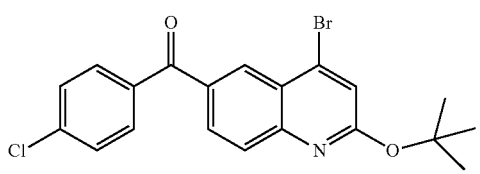

1a

Step 1: Synthesis of (4-chlorophenyl)(4-nitrophenyl)methanone

A 2-L 4-neck flask equipped with a thermocouple controller, a mechanical stirrer, a condenser, and a nitrogen inlet/outlet adapter was charged with DCE (480.8 mL), chlorobenzene (1) (90.4 mL, 888.5 mmol) and 4-nitrobenzoylchloride (111.4 g, 600.3 mmol), and the resulting mixture stirred and warmed to 40° C. Aluminum trichloride (97.0 g, 720.4 mmol) was added portionwise over 1 h and then the reaction was heated to 60° C. and stirred for 10 h.

The reaction was cooled to 20° C., poured into ice-water (2 L) and stirred for 10 min. The resulting aqueous mixture was extracted with DCM (600 mL×2). The combined organic extracts were washed with deionized water (1 L×3). The solvent was concentrated at 40° C. to remove DCM and then at 66° C. to yield a pale to slight yellowish solid, which was dissolved in hot EtOH (500 mL) at 76° C., stirred for 30 min, and then gradually cooled to 4° C. over the course of 1 h. The resulting solid was collected by filtration to yield (4-chlorophenyl)(4-nitrophenyl)methanone as a slightly yellowish crystalline solid. (ES, m/z) 262 (M+H)$^+$, 284, 286 (M+Na)$^+$.

Step 2. Synthesis of (4-aminophenyl)(4-chlorophenyl)methanone

A 3-L 3-neck flask equipped with a thermocouple controller, a mechanical stirrer, a condenser, and a nitrogen inlet/outlet adapter was charged with (4-chlorophenyl)(4-nitrophenyl)methanone (132.0 g, 504.5 mmol), concentrated aqueous HCl (693.3 mL, 8.1 mol), and SnCl$_2$ (313.3 g, 1.62 mol). The yellowish suspension was carefully heated to 36° C. with fast agitation (1000 rmp). The electric power to the heating mantle was turned off at 36° C. A moderate exotherm was observed, which gradually increased to 77° C. over the course of 1 h with gas evolution to form a foamy suspension. The electric power was turned on at 77° C. again and gradually heated to 100° C. over the duration of 30 min and refluxed for 2 h. The reaction was cooled to 10° C., slowly poured into a mixture of ice (1 L) and 33% NaOH (1 L, 8.25 M) with fast stirring in an ice-water bath. The resulting yellowish slurry (pH=2-3) was adjusted to pH=9-10 with 50% NaOH. The resulting solid was collected by filtration and washed with deionized water (100 mL). The filtration cake was dried under air-suction at 20° C. overnight and then in a vacuum oven at 60° C. for 24 h to yield a yellowish solid. The yellowish solid (322 g) was suspended in deionized water (2 L) and extracted with EtOAc (2 L×3). The combined organic phases were washed with brine (1 L/each). The solvent was concentrated at 60° C. to yield (4-aminophenyl)(4-chlorophenyl)methanone as a slightly yellowish crystalline solid. (ES, m/z) 232, 234 (M+H)$^+$ Step 3: Synthesis of ethyl 3-((4-(4-chlorobenzoyl) phenyl)amino)-3-oxopropanoate A 5-L 4-neck flask equipped with a thermocouple controller, a mechanical stirrer, a condenser, and a nitrogen inlet/outlet adapter was charged with (4-aminophenyl)(4-chlorophenyl)methanone (86.6 g, 370.1 mmol), DCM (2.61

L), and Et₃N (70.3 mL, 499.6 mmol). After the solution was cooled to 5° C. in an ice-bath, ethyl 3-chloro-3-oxopropanoate (64.5 mL, 407.1 mmol) was added dropwise over 60 min. The resulting mixture was stirred at 0° C. for 1 h. Additional ethyl 3-chloro-3-oxopropanoate (12.9 mL) was added dropwise and the mixture was stirred at 0° C. for an additional 2 h. The reaction was cooled to 0° C. and ice-water (2 L) was added, followed by solid K₂CO₃ (60 g) until the solution was basic (pH=9-10). After phase separation, the organic layer was concentrated at 40° C. (to remove DCM) and then at 60° C. (to remove ex Et₃N) to yield ethyl 3-((4-(4-chlorobenzoyl)phenyl)amino)-3-oxopropanoate as a slightly yellowish solid, which was used in the next step without further purification. (ES, m/z) 346, 348 (M+H)⁺

Step 4: 3-((4-(4-chlorobenzoyl)phenyl)amino)-3-oxopropanoic acid

A 3-L 4-neck flask equipped with a thermocouple controller, a mechanical stirrer, a dropping funnel, and a nitrogen inlet/outlet adapter was charged with ethyl 3-((4-(4-chlorobenzoyl)phenyl)amino)-3-oxopropanoate (128.0 g, 370.2 mmol), EtOH (1.29 L), and KOH (27.7 g, 1444.2 mmol). The resulting mixture was stirred at 20° C. for 24 h. Additional KOH (1.12 g, 0.04 eq.) was added and the reaction was stirred for an additional 6 h. The resulting yellowish thick slurry was dissolved in deionized water (1.2 L) and then poured into a 12-L 4-neck flask equipped with an overhead stirrer that contained ice-water (6 L) in an ice-water bath. The aqueous pH was adjusted to pH 2-3 using 2 N aqueous HCl solution with fast stirring at 8-10° C. for 20 min. The solid in the resulting milky slurry was collected by filtration, washed with deionized water (100 mL), dried under air-suction for 20 h and then in a vacuum oven at 60° C. under hi-vacuum (20 mmHg) for 72 h to yield 3-((4-(4-chlorobenzoyl)phenyl)amino)-3-oxopropanoic acid as a yellowish solid, which was used in the next step without further purification. (ES, m/z) 318, 320 (M+H)⁺

Step 5: 6-(4-chlorobenzoyl)-4-hydroxyquinolin-2(1H)-one

A 2-L 4-neck flask equipped with a thermocouple controller, a mechanical stirrer, and a nitrogen inlet/outlet adapter was charged with CH₃SO₂OH (236.0 mL, 3.60 mol), P₂O₅ (34.6 g, 241.1 mmol) was added and the mixture was vigorously stirred at 80° C. for 90 min. Solid 3-((4-(4-chlorobenzoyl)phenyl)amino)-3-oxopropanoic acid (111.0 g, 321.4 mmol) was added portionwise over 3 min at 80° C., and the resulting mixture was stirred at 80° C. for 2 h. The hot mixture was poured slowly into ice-water (5 L) and vigorously agitated for 1 h. The resulting solid was collected by filtration, washed with deionized water (2 L×2), and dried by air-suction for 20 h to yield a slightly yellowish solid. The solid was suspended in acetone (990 mL) at 53° C. and sonicated for 30 min. The resulting yellowish slurry was stirred at 20° C. for 10 min. The solid was collected by filtration, washed with acetone (50 mL), dried by air-suction for 1 h and then under high vacuum (22 mmHg) at 60° C. for 20 h to yield 6-(4-chlorobenzoyl)-4-hydroxyquinolin-2 (1H)-one as a light beige-yellowish solid. Elemental analysis: Calculated for C₁₆H₁₀ClNO₅+0.1H₂O+0.21 CH₃COCH₃; MW=313.72. Theoretical: C, 63.67; H, 3.68; Cl, 11.30; N, 4.46; % H₂O, 0.60; Measured: C, 63.58; H, 3.23; Cl, 11.53; N, 4.64; % H₂O, 0.53

Step 6: (4-chlorophenyl)(2,4-dibromoquinolin-6-yl)methanone

To a suspension of 6-(4-chlorobenzoyl)-4-hydroxyquinolin-2(1H)-one (7 g) in toluene (120 mL) was added phosphorus oxybromide (3 eq., 20 g) and the resulting mixture was refluxed until LCMS indicated consumption of starting material. After cooling in an ice bath, the reaction mixture was carefully hydrolyzed by addition of ice/water (200 mL) and neutralized using 6 N solution of NaOH. The precipitates were collected by filtration, washed with water (3×100 ml) and dried under vacuum to yield (4-chlorophenyl)(2,4-dibromoquinolin-6-yl)methanone. (ES, m/z) 426, 428 (M+H)⁺

Step 7: (4-bromo-2-(tert-butoxy)quinolin-6-yl)(4-chlorophenyl)methanone, 1a

A mixture of (4-chlorophenyl)(2,4-dibromoquinolin-6-yl)methanone (5 g) and KOBuᵗ (1.1 eq. 12.93 mmol) in dry toluene (60 mL) was heated at 70° C. for 2 hr. and then cooled to room temperature. The reaction was diluted with EtOAc and water. The aqueous layer was extracted with ethyl acetate. The organics were combined and then washed with water, concentrated and subjected to chromatography (5-15% EtOAc/hexanes silica column) to yield (4-bromo-2-(tert-butoxy)quinolin-6-yl)(4-chlorophenyl)methanone. ¹H NMR (DMSO-d₆) δ: 8.35 (s, 1H), 8.07 (d, J=8.8 Hz, 1H), 7.92 (d, J=8.6 Hz, 1H), 7.79-7.88 (m, J=8.3 Hz, 2H), 7.63-7.74 (m, J=8.1 Hz, 2H), 7.45 (s, 1H), 1.69 (s, 9H).

Example 1

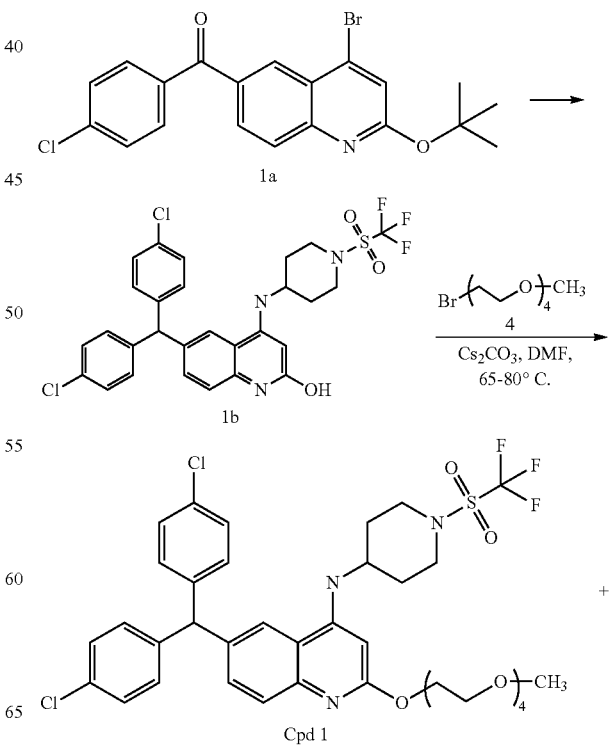

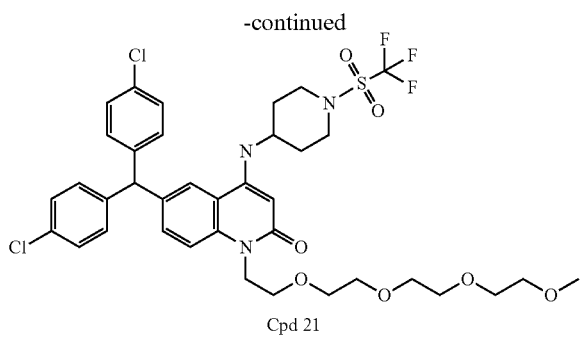

Cpd 21

Step 1. 6-[bis(4-chlorophenyl)methyl]-4-[[1-(trifluoromethane)sulfonylpiperidin-4-yl]amino]quinolin-2-ol, 1b

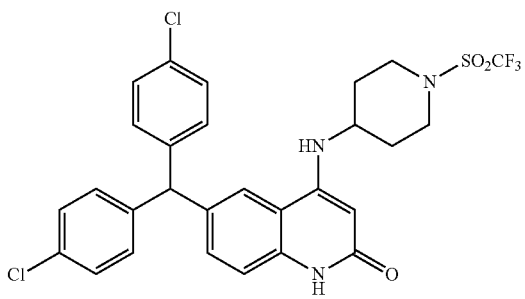

1b

A. (4-Bromo-2-tert-butoxyquinolin-6-yl)bis(4-chlorophenyl)methanol

Into a 250-mL 3-necked round-bottom flask purged and maintained with an inert atmosphere of nitrogen, was placed a solution of (4-bromo-2-tert-butoxyquinolin-6-yl)(4-chlorophenyl)methanone, 1a (4 g, 9.55 mmol, 1.00 equip) in tetrahydrofuran (65 mL). To the resulting mixture was then added (4-chlorophenyl)magnesium bromide (8.2 mL, 1.30 equip, 1 M) dropwise with stirring at 0° C. The resulting solution was stirred for 2 h at 0° C. The reaction was then quenched by the addition of water. The resulting solution was extracted with ethyl acetate (3×150 mL) and the organic layers combined. The resulting mixture was washed with water (2×100 mL) of water and brine (1×100 mL). The resulting mixture was dried over anhydrous sodium sulfate. The residue was applied onto a silica gel column with ethyl acetate:petroleum ether (1:4) to yield (4-bromo-2-tert-butoxyquinolin-6-yl)bis(4-chlorophenyl)methanol as white solid. (ES, m/z): [M+H]+ 532

Step B. 4-bromo-6-((4-chlorophenyl)(thiazol-2-yl)methyl)quinolin-2-ol

Into a 100-mL round-bottom flask, was placed a solution of [4-bromo-2-(tert-butoxy)quinolin-6-yl]bis(4-chlorophenyl)methanol (1.5 g, 2.82 mmol, 1.00 equip) in dichloromethane (55 mL), Et$_3$SiH (1.3 g, 4.00 equip), and trifluoroacetic acid (8 g, 70.77 mmol, 25.00 equip). The resulting solution was stirred overnight at room temperature. The pH value of the solution was adjusted to 7-8 with sodium bicarbonate. The resulting solution was extracted with DCM (3×50 ml) and the organic layers combined. The resulting mixture was washed with water (2×50 mL). The resulting mixture was washed with brine (1×50 mL). The resulting mixture was dried over anhydrous sodium sulfate and concentrated to yield 6-[bis(4-chlorophenyl)methyl]-4-bromoquinolin-2-ol as a white solid. (ES, m/z): [M+H]+ 433

Step C. 6-(bis(4-chlorophenyl)methyl)-4-(1-(trifluoromethylsulfonyl) piperidin-4-ylamino)quinolin-2-ol Into a 100-mL round bottom flask purged and maintained with an inert atmosphere of nitrogen, was placed 6-[bis(4-chlorophenyl)methyl]-4-bromoquinolin-2-ol (3.4 g, 7.40 mmol, 1.00 equip), 1-(trifluoromethane)sulfonylpiperidin-4-amine hydrochloride (3.4 g, 12.65 mmol, 1.70 equip), Pd(dba)$_3$ (680 mg, 0.10 equip), dppf (1.44 g, 2.60 mmol, 0.35 equip), Cs$_2$CO$_3$ (6.05 g, 2.50 equip), KOt-Bu (1.5 g, 1.80 equip), and 1,4-dioxane (35 mL). The resulting solution was stirred overnight at 100° C. The reaction was then quenched by the addition of water (100 mL). The resulting solution was extracted with ethyl acetate (3×150 mL) and the organic layers combined. The resulting mixture was washed with water (2×100 mL) and brine (1×100 mL). The resulting mixture was dried over anhydrous sodium sulfate and concentrated under vacuum. The residue was applied onto a silica gel column with dichloromethane/methanol (10:1). The resulting residue was purified by recrystallization from CH$_3$CN to yield 6-[bis(4-chlorophenyl)methyl]-4-[[1-(trifluoromethane)sulfonylpiperidin-4-yl]amino]quinolin-2-ol, compound 1b. (ES, m/z): [M+H]+ 610; $^1$H-NMR (300 MHz, DMSO-d$_6$) δ 10.786 (s, 1H), 7.930 (s, 1H), 7.390-7.418 (m, 4H), 7.128-7.222 (m, 6H), 6.542 (d, J=7.8 Hz, 1H), 5.629 (s, 1H), 5.490 (s, 1H), 3.872 (d, J=13.2 Hz, 2H), 3.373 (br, 1H), 3.411-3.452 (m, 2H), 2.069-2.107 (m, 2H), 1.556-1.663 (m, 2H).

Step 2. Synthesis of Compound 1 and Compound 21

To a solution of 6-(bis(4-chlorophenyl)methyl)-4-((1-((trifluoromethyl)sulfonyl)piperidin-4-yl)amino)quinolin-2-ol, cpd 1b, (66.67 mg, 0.109 mmol) in DMF (2 mL) was added Cs$_2$CO$_3$ (71.2 mg, 0.218 mmol) followed by 13-bromo-2,5,8,11-tetraoxatridecane (35.5 mg, 0.13 mmol). The mixture was heated at 75° C. for 36 h. The reaction was partitioned between EtOAc and water. The aqueous layer was extracted with EtOAc. The combined organic extracts were concentrated and purified by column chromatography on silica gel. Elution with 55% EtOAc/heptane gave 25 mg of compound 1, followed by elution with 5% MeOH/EtOAc to give 35 mg of compound 21.

Compound 1: $^1$H NMR (CHLOROFORM-d) δ: 7.67 (d, J=9.1 Hz, 1H), 7.23-7.30 (m, 6H), 7.03 (d, J=8.6 Hz, 4H), 5.98 (s, 1H), 5.63 (s, 1H), 4.57-4.62 (m, 2H), 4.47 (d, J=7.1 Hz, 1H), 3.99 (br d, J=12.6 Hz, 2H), 3.85-3.90 (m, 2H), 3.59-3.74 (m, 10H), 3.51-3.59 (m, 2H), 3.37 (s, 3H), 3.17-3.35 (m, 2H), 2.26 (br d, J=11.1 Hz, 2H), 1.58-1.70 (m, 2H); (ES, m/z): 800.1, 802.2[M+H]+.

Compound 21: $^1$H NMR (CHLOROFORM-d) δ: 7.51 (d, J=8.6 Hz, 1H), 7.24-7.30 (m, 4H), 7.12-7.24 (m, 2H), 7.01 (d, J=8.6 Hz, 4H), 5.70 (s, 1H), 5.57 (s, 1H), 4.53 (brd, J=7.1 Hz, 1H), 4.41 (t, J=6.3 Hz, 2H), 3.97 (br d, J=13.1 Hz, 2H), 3.75 (t, J=6.1 Hz, 2H), 3.56-3.71 (m, 10H), 3.51-3.54 (m, 2H), 3.36 (s, 3H), 3.21 (br t, J=11.1 Hz, 2H), 2.24 (br d, J=11.6 Hz, 2H), 1.50-1.69 (m, 2H); (ES, m/z): 800.1[M+H]+; 824.1 [M+Na]+.

Following the procedures described in Example 1 above, and substituting suitably selected reagents, starting materials and conditions as would be readily apparent to those skilled in the art, the following representative compounds of the present invention were prepared.

| Cpd No. | Structure | Analytical data |
|---|---|---|
| 2 | 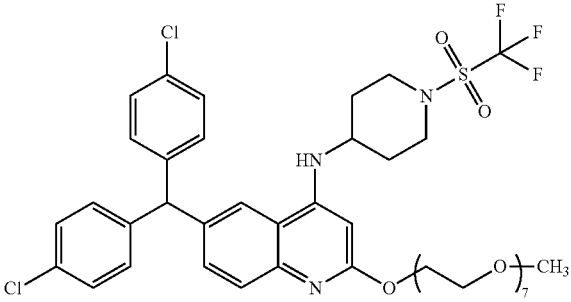 | (ES, m/z): 932.3, 934.2 [M + H]+; |
| 3 | 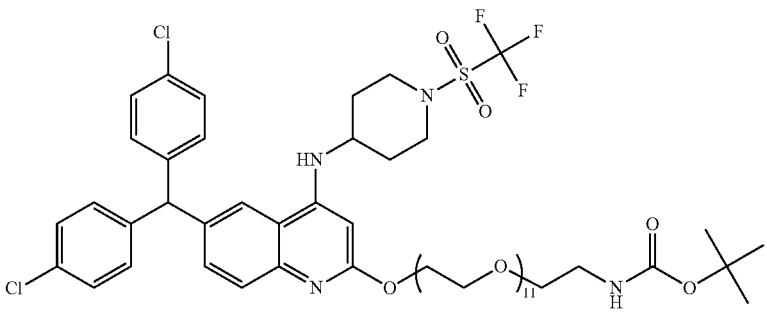 | (ES, m/z): 1239.4 [M + H]+; 1261.3, 1264.4 [M + Na]+ |
| 4 | 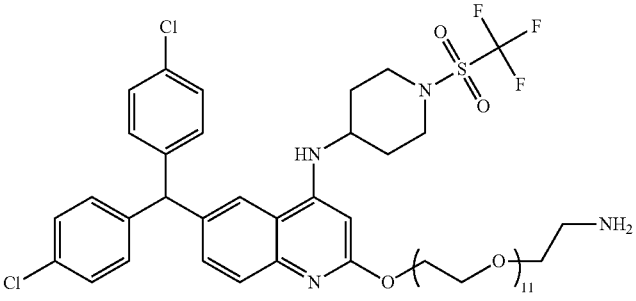 | (ES, m/z): 1130.3, 1133.2 [M + H]+; |
| 8 | 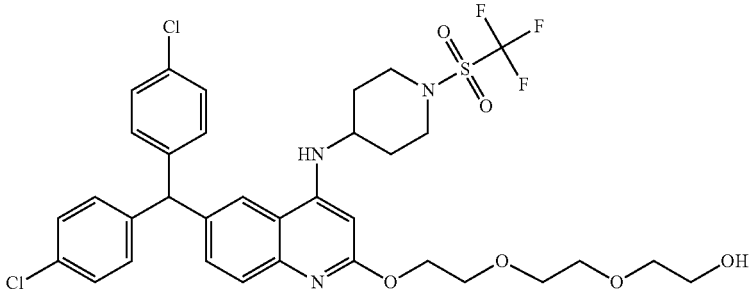 [SMILES: O=S(=O)(N1CCC(Nc2cc(OCCOCCOCCO)nc3ccc(C(c4ccc(Cl)cc4)c4ccc(Cl)cc4)cc23)CC1)C(F)(F)F] | $^1$H NMR (CHLOROFORM-d) δ: 7.67 (d, J = 8.6 Hz, 1H), 7.20-7.34 (m, 6H), 7.03 (d, J = 8.6 Hz, 4H), 5.99 (s, 1H), 5.63 (s, 1H), 4.57-4.64 (m, 2H), 4.52 (d, J = 7.1 Hz, 1H), 3.93-3.99 (m, 2H), 3.83-3.92 (m, 2H), 3.71-3.74 (m, 6H), 3.57-3.60 (m, 2H), 3.13-3.33 (m, 2H), 2.60 (br s, 1H), 2.24 (br d, J = 11.1 Hz, 2H), 1.52-1.68 (m, 2H); (ES, m/z): 742.1, 742.2 [M + H]+ |
| 9 | 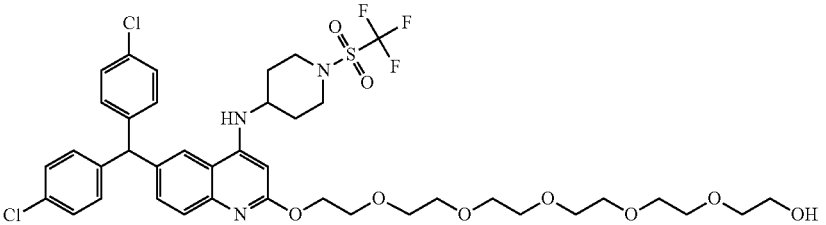 [SMILES: O=S(=O)(N1CCC(Nc2cc(OCCOCCOCCOCCOCCOCCO)nc3ccc(C(c4ccc(Cl)cc4)c4ccc(Cl)cc4)cc23)CC1)C(F)(F)F] | (ES, m/z): 874.2, 876.2 [M + H]+; |

| Cpd No. | Structure | Analytical data |
|---|---|---|
| 23 | 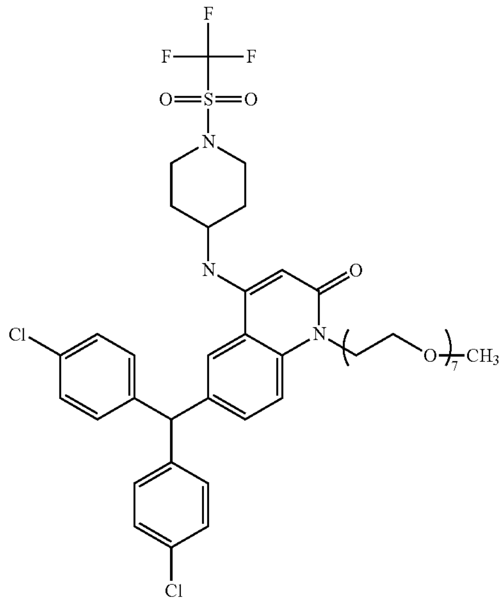 | (ES, m/z): 932.3, 935.3 [M + H]+; 954.2, 956.3 [M + Na]+ |
| 24 | 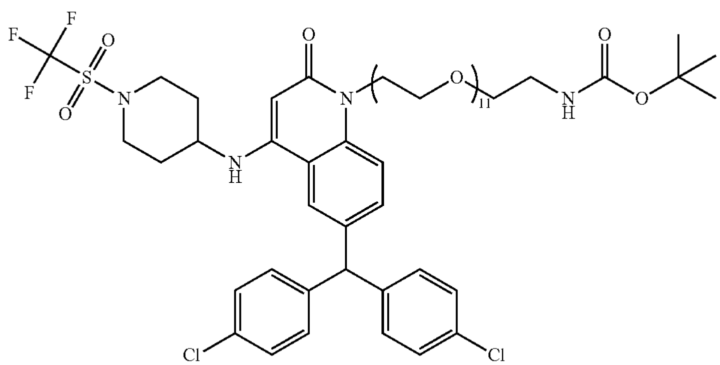 | (ES, m/z): 1238.3, 1240.3 [M + H]+; |
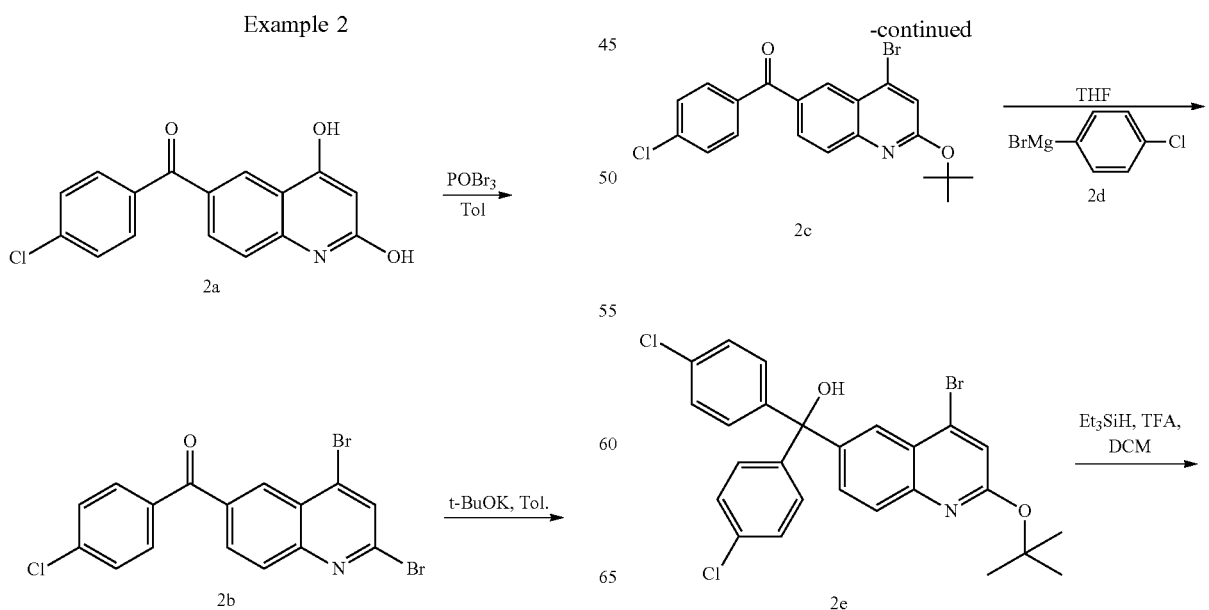
Example 2

69

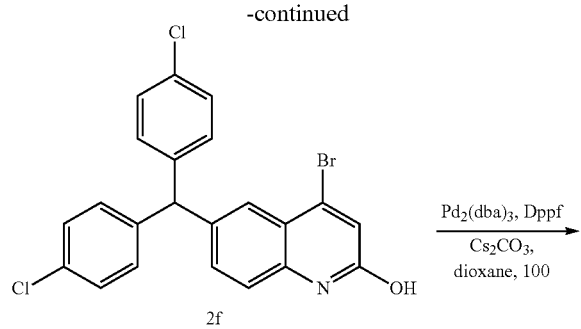

Step 1. Synthesis of 2,4-dibromo-6-[(4-chlorophenyl)carbonyl]quinoline, 2b

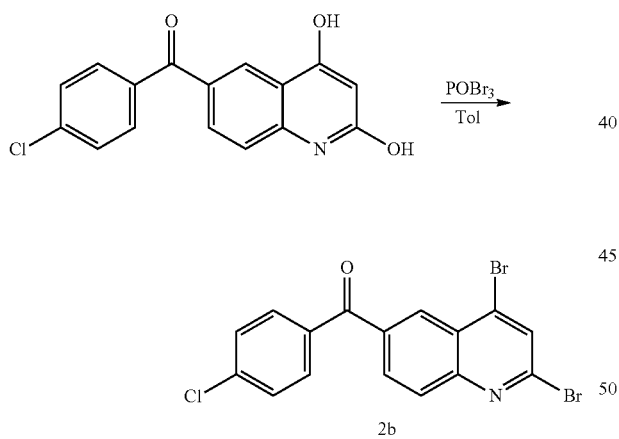

Into a 1-L round-bottom flask, was placed a solution of 6-[(4-chlorophenyl)carbonyl]quinoline-2,4-diol (Example A, Step 5) (35 g, 116.78 mmol, 1.00 equiv) in toluene (600 mL), POBr₃ (100 g, 3.00 equiv). The resulting solution was stirred for 5 h at 115° C. The reaction mixture was cooled with a water/ice bath. The reaction was then quenched by the addition of 500 mL of water/ice. The pH value of the solution was adjusted to 7 with sodium hydroxide (6 mol/L). The solids were collected by filtration. The solid was dried in an oven under reduced pressure. This resulted in 38 g (76%) of 2,4-dibromo-6-[(4-chlorophenyl)carbonyl]quinoline, compound 2b, as a yellow solid. LC-MS: (ES, m/z): 426 [M+H]⁺.

70

Step 2. Synthesis of 4-bromo-2-(tert-butoxy)-6-[(4-chlorophenyl)carbonyl]quinoline, 2c

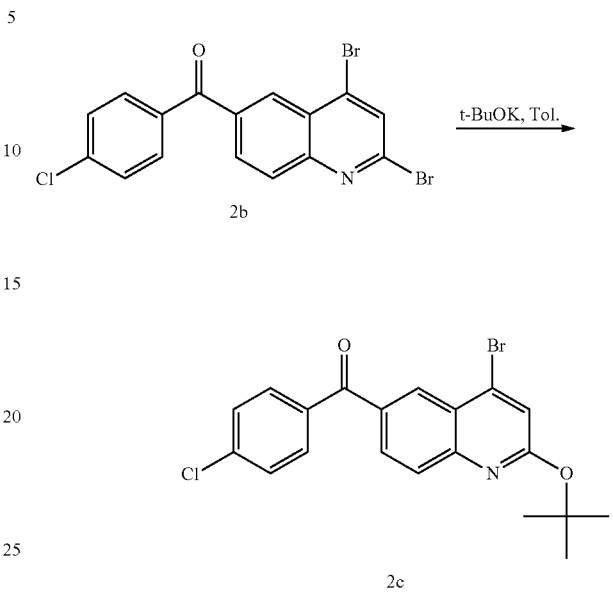

Into a 250-mL 3-necked round-bottom flask purged and maintained with an inert atmosphere of nitrogen, was placed compound 2b (9 g, 20.73 mmol, 1.00 equiv, 98%), toluene (90 mL), and t-BuOK (23.3 mL, 1.10 equiv). The resulting solution was stirred for 1 h at 70° C. in an oil bath. The reaction was then quenched by the addition of 50 mL of water. The resulting solution was extracted with 3×50 mL of ethyl acetate and the organic layers combined. The resulting mixture was washed with 1×50 mL of water and 1×50 mL of brine. The mixture was dried over anhydrous sodium sulfate. The solids were removed by filtration. The resulting mixture was concentrated under reduced pressure. The residue was applied to a silica gel column with ethyl acetate/petroleum ether (1:5) as eluent. This resulted in 3 g (35%) of 4-bromo-2-(tert-butoxy)-6-[(4-chlorophenyl)carbonyl]quinoline, compound 2c, as a white solid. LC-MS: (ES, m/z): 420 [M+H]⁺.

Step 3. Synthesis of [4-bromo-2-(tert-butoxy)quinolin-6-yl]bis(4-chlorophenyl)methanol, 2e

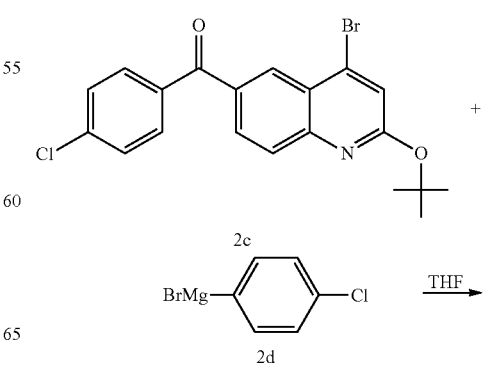

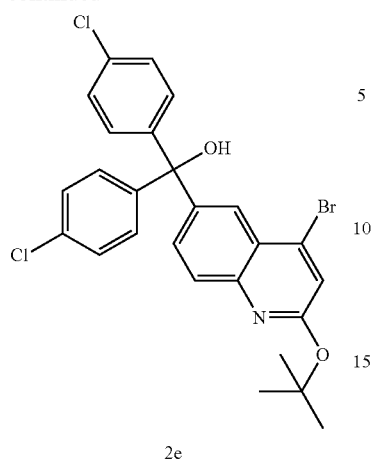

2e

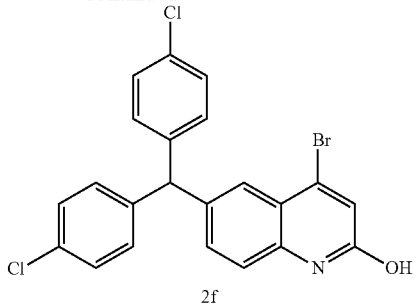

2f

Into a 100-mL round-bottom flask, was placed compound 2e (3.5 g, 6.61 mmol, 1.00 equiv, 98%), Et₃SiH (3.06 g, 25.79 mmol, 4.00 equiv), trifluoroacetic acid (17.78 g, 154.14 mmol, 25.00 equiv, 98%), dichloromethane (50 mL). The resulting solution was stirred for 2 h at room temperature. The resulting mixture was concentrated under reduced pressure. The crude product was purified by recrystallization from EA. This resulted in 2.5 g (82%) of 6-[bis(4-chlorophenyl)methyl]-4-bromoquinolin-2-ol, compound 2f, as a white solid. LC-MS: (ES, m/z): 460 [M+H]⁺.

Step 5. Synthesis of 6-[bis(4-chlorophenyl)methyl]-4-([4-[2-(2-methoxyethoxy) ethoxy]phenyl]amino) quinolin-2-ol, Cpd 20

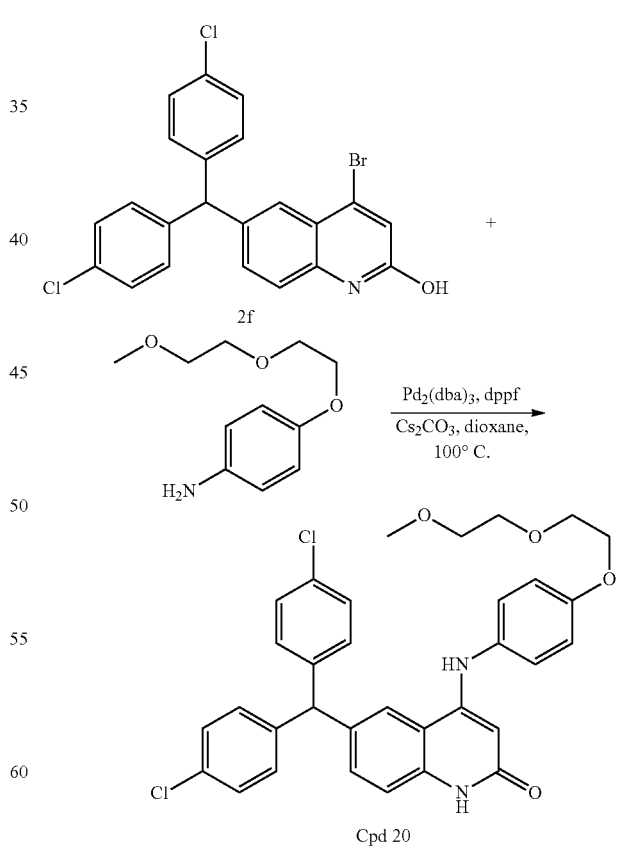

Into a 100-mL round-bottom flask purged and maintained with an inert atmosphere of nitrogen, was placed compound 2c (2.8 g, 6.55 mmol, 1.00 equiv, 98%), tetrahydrofuran (40 mL). This was followed by the addition of bromo(4-chlorophenyl)magnesium (13.4 mL, 2.00 equiv, cpd 2d) dropwise with stirring at 0° C. The resulting solution was stirred overnight at room temperature. The reaction was then quenched by the addition of 50 mL of water. The resulting solution was extracted with 3×50 mL of ethyl acetate and the organic layers combined. The resulting mixture was washed with 1×50 mL of water and 1×50 mL of brine. The mixture was dried over anhydrous sodium sulfate. The solids were removed by filtration. The resulting mixture was concentrated under reduced pressure. The residue was applied to a silica gel column with ethyl acetate/petroleum ether (1:2) as eluent. This resulted in 3.5 g (crude) of [4-bromo-2-(trimethyl-ˆ[4]-oxidanyl)quinolin-6-yl]bis(4-chlorophenyl) methanol, compound 2e, as a light yellow solid. LC-MS: (ES, m/z): 532 [M+H]⁺.

Step 4. Synthesis of 6-[bis(4-chlorophenyl)methyl]-4-bromoquinolin-2-ol, 2f

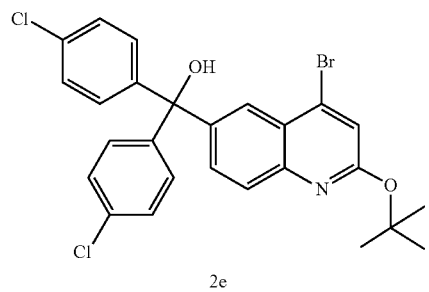

2e

Et₃SiH, TFA, DCM
→

Into an 8-mL sealed tube, purged and maintained with an inert atmosphere of nitrogen, was placed compound 2f (80 mg, 0.17 mmol, 1.00 equiv, 99%), 4-[2-(2-methoxyethoxy)

ethoxy]aniline (prepared according to Ex 4 of U.S. Patent Application US20090004753) (62.6 mg, 0.29 mmol, 1.70 equiv), Pd$_2$(dba)$_3$ (16 mg, 0.02 mmol, 0.10 equiv), dppf (33.8 mL, 0.35 equiv), Cs$_2$CO$_3$ (142 mg, 0.43 mmol, 2.50 equiv, 99%), dioxane (3 mL). The resulting solution was stirred overnight at 100° C. in an oil bath. The resulting solution was diluted with 30 mL of water. The resulting solution was extracted with 3×30 mL of ethyl acetate and the organic layers combined. The resulting mixture was washed with 1×30 mL of water and 1×30 mL of brine. The mixture was dried over anhydrous sodium sulfate. The solids were removed by filtration. The resulting mixture was concentrated under reduced pressure. The residue was applied to a silica gel column with dichloromethane/methanol (20:1) as eluent. This resulted in 30.9 mg (30%) of 6-[bis(4-chlorophenyl)methyl]-4-([4-[2-(2-methoxyethoxy)ethoxy]phenyl]amino)quinolin-2-ol, Cpd 20, as a white solid. LC-MS: (ES, m/z): 589 [M+H]$^+$; $^1$H NMR (300 MHz, D$_2$O) δ: 10.90 (s, 1H), 8.43 (s, 1H), 7.98 (s, 1H), 7.37-7.40 (m, 4H), 7.15-7.21 (m, 8H), 6.97-7.00 (m, 2H), 5.63 (s, 1H), 5.34 (s, 1H), 4.09 (t, J=4.8 Hz, 2H), 3.73 (t, J=4.8 Hz, 2H), 3.57-3.60 (m, 2H), 3.44-3.47 (m, 2H), 3.24 (s, 3H).

Example 3

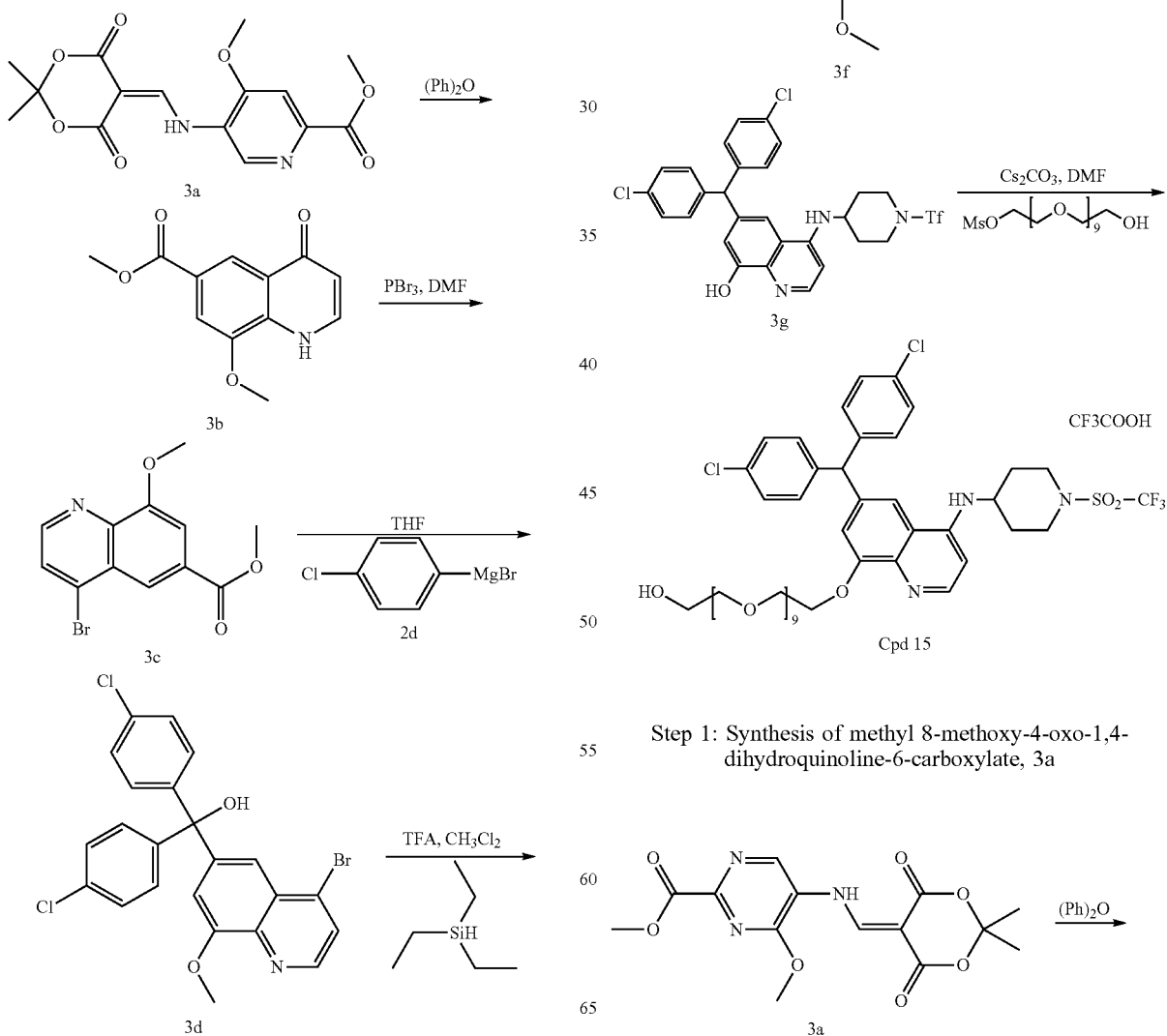

Step 1: Synthesis of methyl 8-methoxy-4-oxo-1,4-dihydroquinoline-6-carboxylate, 3a

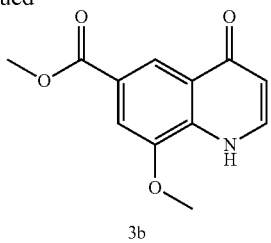

Into a 250-mL round-bottom flask, was placed methyl 5-[[(2,2-dimethyl-4,6-dioxo-1,3-dioxan-5-ylidene)methyl]amino]-4-methoxypyridine-2-carboxylate (10 g, 29.74 mmol, 1.00 equiv), (Ph)$_2$O (100 mL). The resulting solution was stirred for 1 h at 200° C. The reaction mixture was cooled using an ice water bath. The solids were collected by filtration. This resulted in 6 g (86%) of methyl 8-methoxy-4-oxo-1,4-dihydroquinoline-6-carboxylate, compound 3b, as a yellow solid. LC-MS: (ES, m/z): 234 [M+H]$^+$.

Step 2. Synthesis of bromo-8-methoxyquinoline-6-carboxylate, 3c

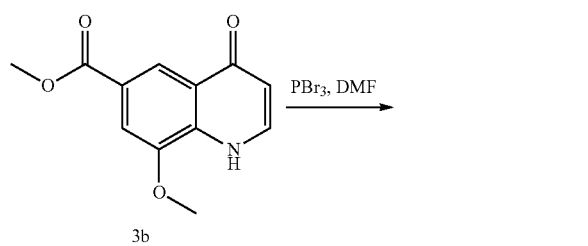

Into a 250-mL 3-necked round-bottom flask, purged and maintained with an inert atmosphere of nitrogen, was placed compound 3b (6 g, 25.73 mmol, 1.00 equiv), N,N-dimethylformamide (120 mL), followed by the dropwise addition of PBr$_3$ (7.6 g, 28.08 mmol, 1.10 equiv) with stirring. The resulting solution was stirred for 3 h at 25° C. The reaction was then quenched by the addition of 500 mL of water. The pH of the solution was adjusted to 8-9 with sodium bicarbonate. The solids were collected by filtration. This resulted in 6 g (78%) of methyl 4-bromo-8-methoxyquinoline-6-carboxylate, compound 3c, as a yellow solid. LC-MS: (ES, m/z): 296 [M+H]$^+$.

Step 3. Synthesis of (4-bromo-8-methoxyquinolin-6-yl)bis(4-chlorophenyl)methanol, 3d

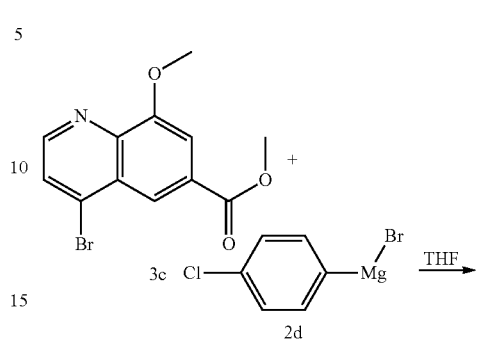

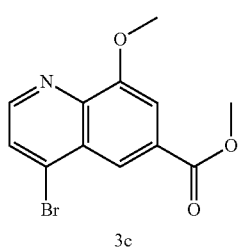

Into a 1000-mL 3-necked round-bottom flask, was placed compound 3c (6 g, 20.26 mmol, 1.00 equiv), tetrahydrofuran (500 mL), bromo(4-chlorophenyl)magnesium (60 mL, 3.00 equiv). The resulting solution was stirred for 3 h at reflux. The reaction was then quenched by the addition of 400 mL of water. The resulting solution was extracted with 3×300 mL of ethyl acetate and the organic layers were combined and dried over anhydrous sodium sulfate. The solids were removed by filtration. The resulting mixture was concentrated under reduced pressure. The residue was applied to a silica gel column with ethyl acetate/petroleum ether (2:1) as eluent. This resulted in 6 g (60%) of (4-bromo-8-methoxyquinolin-6-yl)bis(4-chlorophenyl)methanol, compound 3d, as a yellow solid. LC-MS: (ES, m/z): 489 [M+H]$^+$.

Step 4. Synthesis of 6-[bis(4-chlorophenyl)methyl]-4-bromo-8-methoxyquinoline, 3e

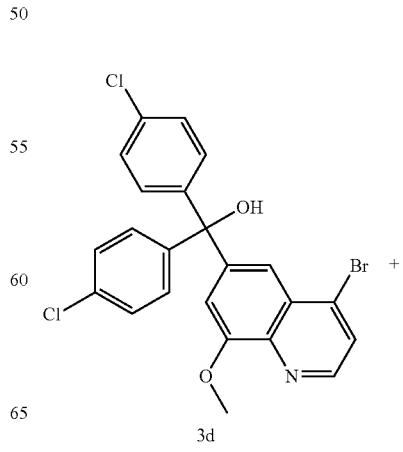

-continued

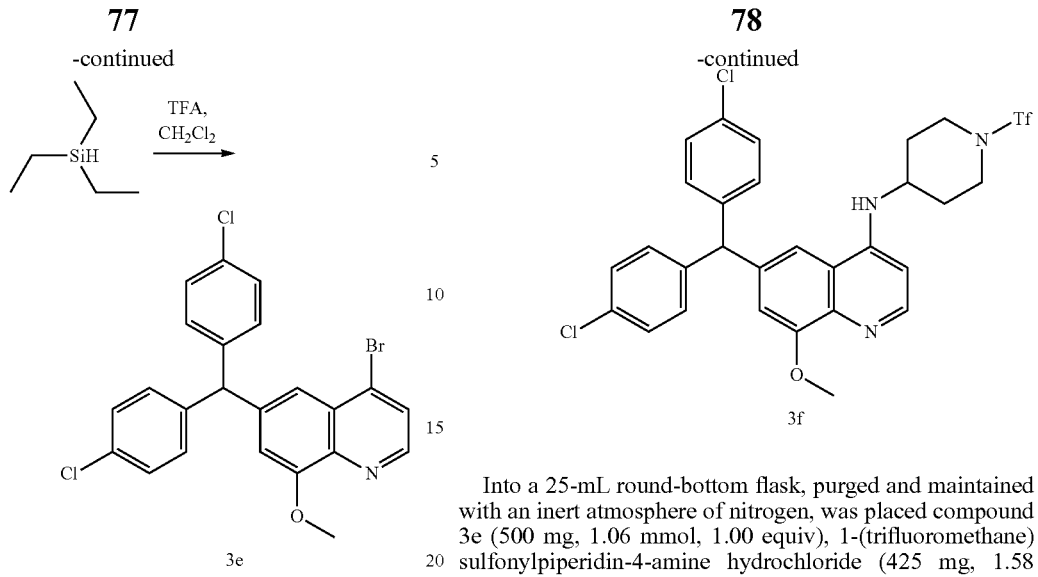

3e

Into a 500-mL 3-necked round-bottom flask, was placed compound 3d (6 g, 12.27 mmol, 1.00 equiv), dichloromethane (200 mL), triethylsilane (8 mL), trifluoroacetic acid (24 mL). The resulting solution was stirred overnight at 25° C. The resulting solution was diluted with 100 mL of dichloromethane. The resulting mixture was washed with 3×100 mL of sodium bicarbonate (aq). The mixture was dried over anhydrous sodium sulfate. The solids were removed by filtration. The resulting mixture was concentrated under reduced pressure. This resulted in 4 g (68%) of 6-[bis(4-chlorophenyl)methyl]-4-bromo-8-methoxyquinoline, compound 3e, as a yellow solid. LC-MS: (ES, m/z): 474 [M+H]$^+$.

Step 5. Synthesis of 6-[bis(4-chlorophenyl)methyl]-8-methoxy-N-[1-(trifluoromethane)sulfonylpiperidin-4-yl]quinolin-4-amine, 3f

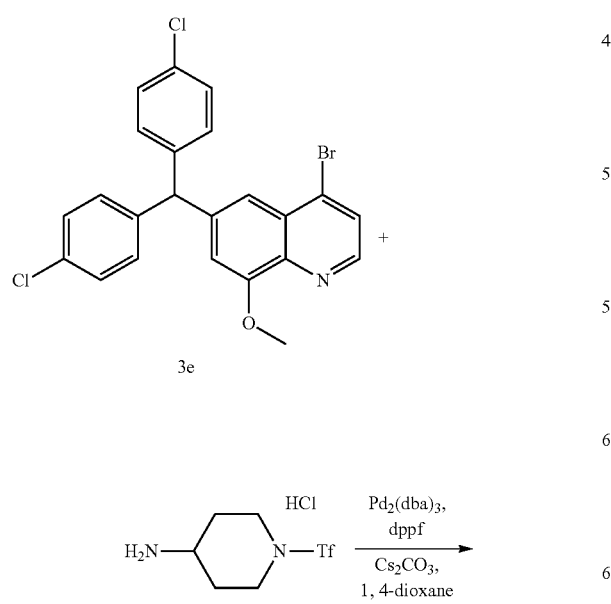

-continued

3f

Into a 25-mL round-bottom flask, purged and maintained with an inert atmosphere of nitrogen, was placed compound 3e (500 mg, 1.06 mmol, 1.00 equiv), 1-(trifluoromethane)sulfonylpiperidin-4-amine hydrochloride (425 mg, 1.58 mmol, 1.50 equiv), Pd$_2$(dba)$_3$ (55 mg, 0.05 mmol, 0.05 equiv), dppf (100 mg, 0.18 mmol, 0.17 equiv), Cs$_2$CO$_3$ (1000 mg, 3.07 mmol, 3.00 equiv), 1,4-dioxane (10 mL). The resulting solution was stirred overnight at 80° C. The resulting solution was diluted with 100 mL of ethyl acetate. The resulting mixture was washed with 3×50 mL of water. The mixture was dried over anhydrous sodium sulfate. The solids were removed by filtration. The resulting mixture was concentrated under reduced pressure. The residue was applied to a silica gel column with dichloromethane/methanol (5:1) as eluent. This resulted in 300 mg (45%) of 6-[bis(4-chlorophenyl)methyl]-8-methoxy-N-[1-(trifluoromethane)sulfonylpiperidin-4-yl]quinolin-4-amine, compound 3f, as a yellow solid. LC-MS: (ES, m/z): 625 [M+H]$^+$.

Step 6. Synthesis of 6-[bis(4-chlorophenyl)methyl]-4-[[1-(trifluoromethane)sulfonylpiperidin-4-yl]amino]quinolin-8-ol, 3g

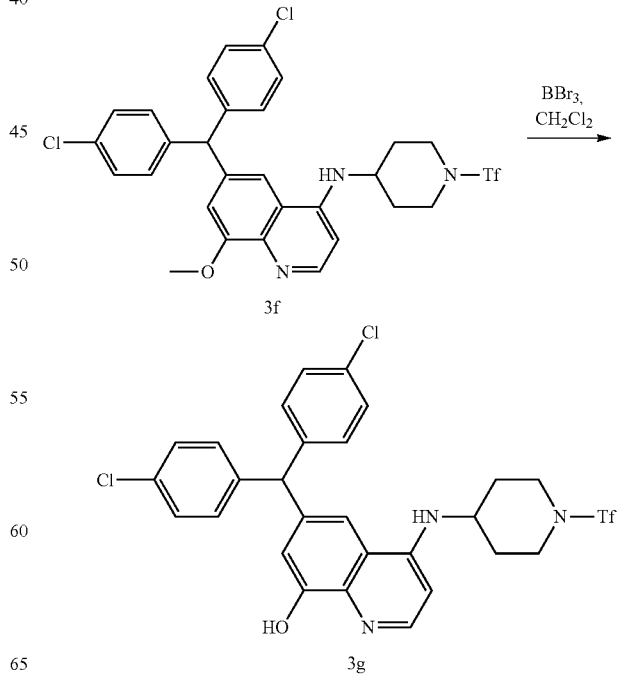

Into a 250-mL round-bottom flask, was placed compound 3f (1 g, 1.60 mmol, 1.00 equiv), dichloromethane (100 mL). This was followed by the dropwise addition of BBr$_3$ (1.6 g, 6.40 mmol, 4.00 equiv) with stirring at −78° C. The resulting solution was stirred overnight at 25° C. The reaction was then quenched by the addition of 100 mL of water. The resulting mixture was concentrated under reduced pressure. The solids were collected by filtration. The residue was applied to a silica gel column with dichloromethane:ethanol (10:1) as eluent. This resulted in 700 mg (71%) of 6-[bis(4-chlorophenyl)methyl]-4-[[1-(trifluoromethane)sulfonylpiperidin-4-yl]amino]quinolin-8-ol, compound 3g, as a yellow solid. LC-MS: (ES, m/z): 610 [M+H]$^+$.

Step 7. Synthesis of 1-[6-[bis(4-chlorophenyl)methyl]-4-[[1-(trifluoromethane)sulfonylpiperidin-4-yl]amino]quinolin-8-yl]-1,4,7,10,13,16,19,22,25,28-decaoxatriacontan-30-ol trifluoroacetic acid, Cpd 15

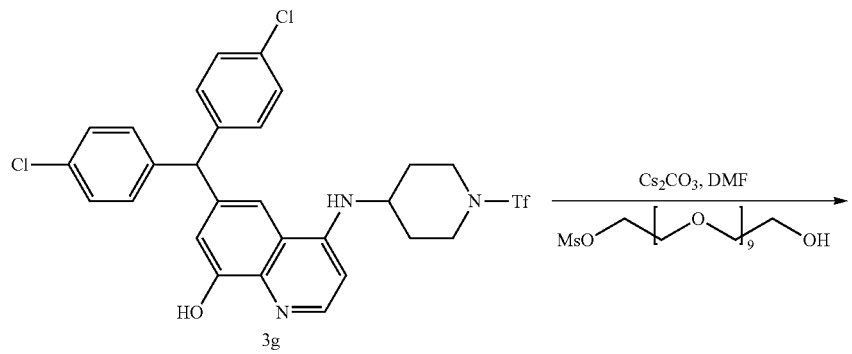

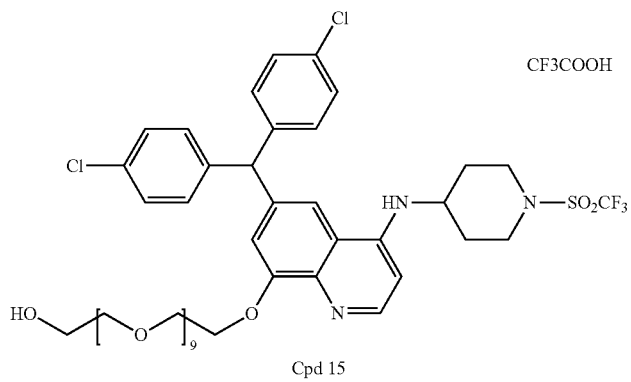

Into a 25-mL round-bottom flask was placed compound 3g (100 mg, 0.16 mmol, 1.00 equiv), N,N-dimethylformamide (10 mL), 29-hydroxy-3,6,9,12,15,18,21,24,27-nonaoxanonacosan-1-yl methanesulfonate (88 mg, 0.16 mmol, 1.00 equiv), Cs$_2$CO$_3$ (160 mg, 0.49 mmol, 3.00 equiv). The resulting solution was stirred overnight at 60° C. The solids were removed by filtration. The crude product was purified by reverse phase preparative-HPLC with the following conditions: column, SunFire Prep; mobile phase A: water with 0.05% CF$_3$COOH; Phase B: CH$_3$CN (35-70% CH$_3$CN. This resulted in 6.6 mg (4%) of N-[4-([6-[bis(4-chlorophenyl)methyl]-4-[[1-(trifluoromethane)sulfonylpiperidin-4-yl]amino]quinolin-8-yl]oxy)butyl]acetamide as its trifluoroacetic acid as a white solid.

This resulted in 9.8 mg (6%) of 1-[6-[bis(4-chlorophenyl)methyl]-4-[[1-(trifluoromethane)sulfonylpiperidin-4-yl]amino]quinolin-8-yl]-1,4,7,10,13,16,19,22,25,28-decaoxatriacontan-30-ol trifluoroacetic acid, compound 15, as light yellow oil. LC-MS: (ES, m/z): 1050 [M+H]$^+$; $^1$H NMR (300 MHz, CD$_3$OD) δ: 8.38 (m, J=6.9 Hz, 1H), 7.95 (s, 1H), 7.36-7.39 (m, 4H), 7.28 (s, 1H), 7.17-7.19 (m, 4H), 7.05-7.07 (m, 1H), 5.81 (s, 1H), 4.33-4.36 (m, 2H), 4.04-4.19 (m, 4H), 3.92-3.95 (m, 2H), 3.54-3.68 (m, 38H), 2.18-2.22 (m, 2H), 1.82-1.87 (m, 2H).

Following the procedures described in Example 3 above, and substituting suitably selected reagents, starting materials and conditions as would be readily apparent to those skilled in the art, the following representative compounds of the present invention were prepared.

| Cpd No. | Structure | Analytical data |
|---|---|---|
| 16 | 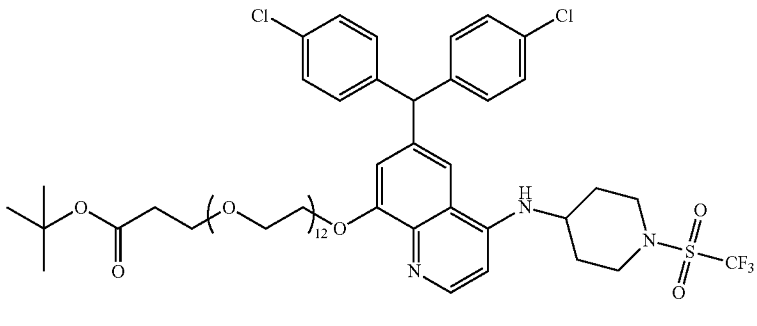 | (ES, m/z): 1267.3, 1268.4, 1269.3 [M + H]+; |
| 17 | 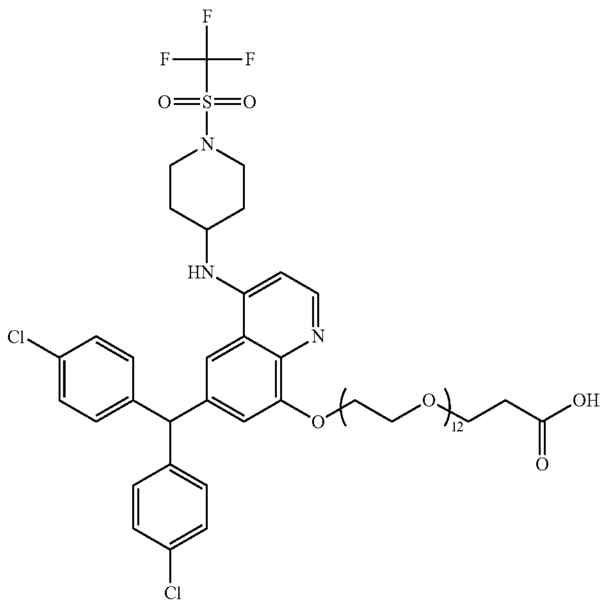 | (ES, m/z): 1212.3, 1214.3 [M + H]+; |
Example 4
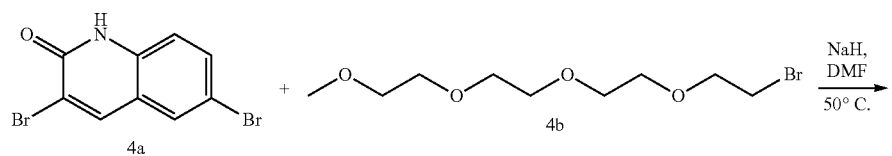
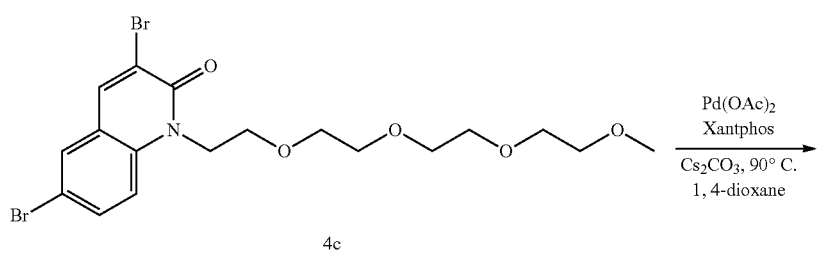

-continued
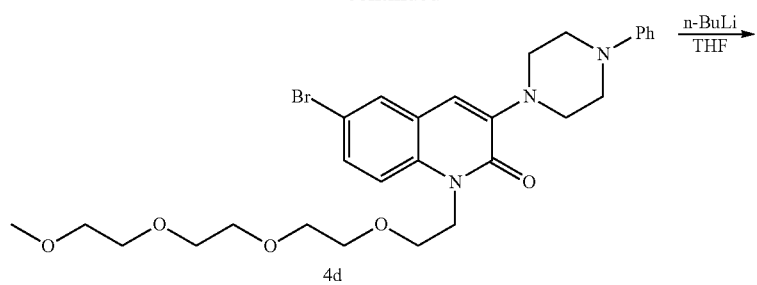
4d
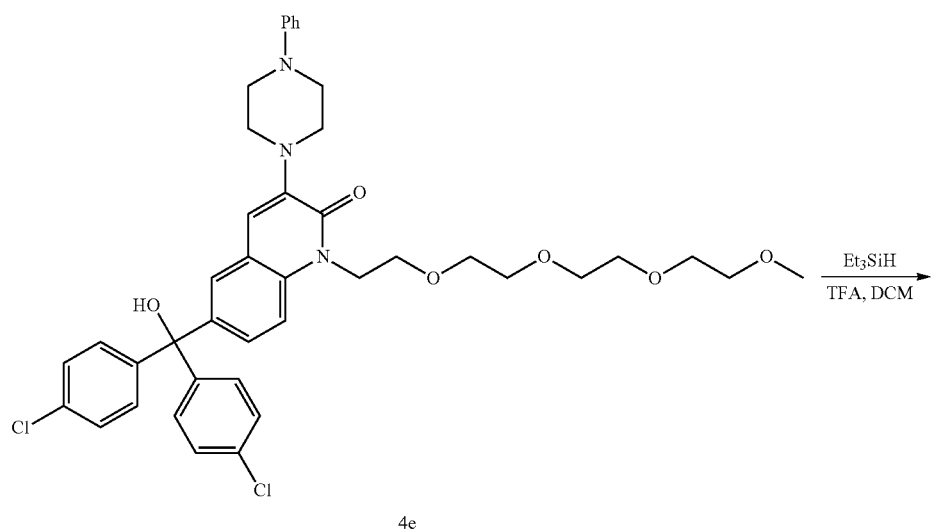
4e
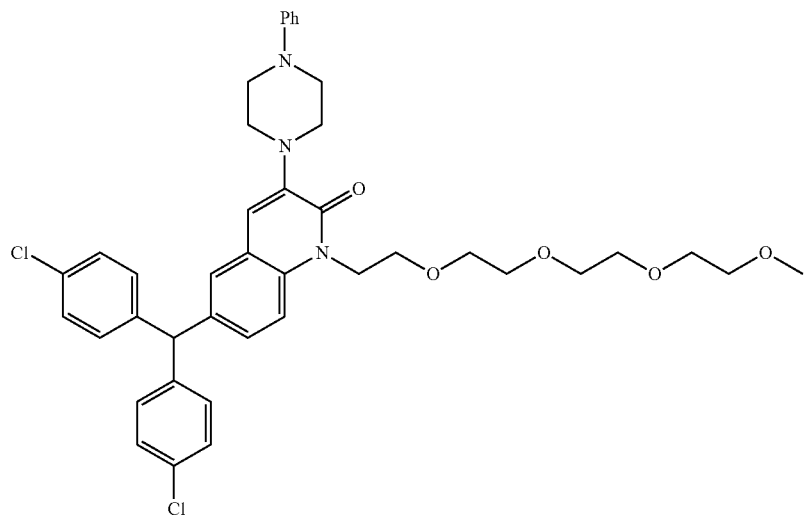
Cpd 24

Step 1. Synthesis of 3,6-dibromo-1-(2,5,8,11-tetraoxatridecan-13-yl)-1,2-dihydroquinolin-2-one, 4c

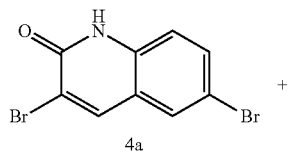

4a

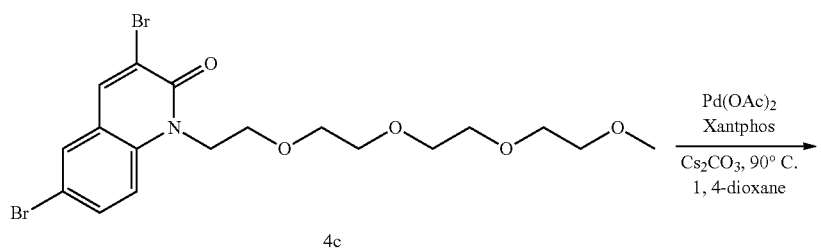

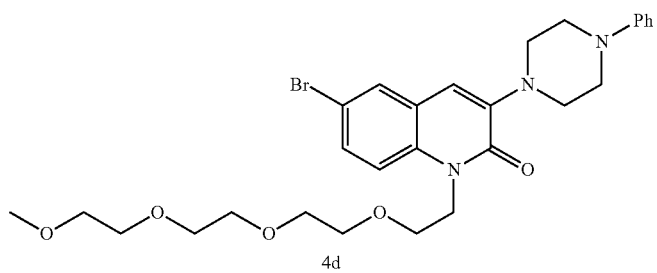

4d

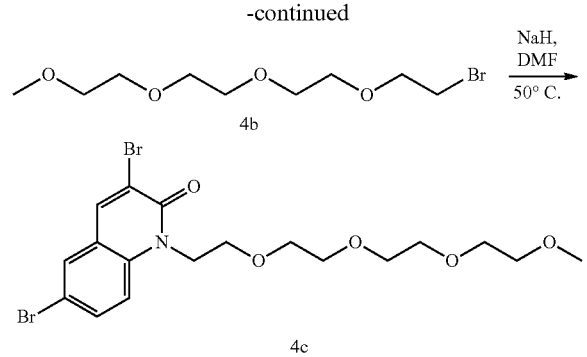

Into a 25-mL round-bottom flask, purged and maintained with an inert atmosphere of nitrogen, was placed a solution of 3,6-dibromo-1,2-dihydroquinolin-2-one (650 mg, 2.15 mmol, 1.00 equiv) in N,N-dimethylformamide (10 mL). This was followed by the addition of sodium hydride (172 mg, 7.17 mmol, 2.00 equiv), in portions. The resulting solution was stirred for 5 min at 50° C. To this was added 13-bromo-2,5,8,11-tetraoxatridecane, compound 4b (1.2 g, 4.43 mmol, 2.00 equiv) dropwise with stirring at 50° C. The resulting solution was stirred overnight at 50° C. The reaction was then quenched by the addition of 30 mL of saturated sodium bicarbonate solution. The mixture was extracted with 2×50 mL of ethyl acetate and the organic layers were combined, dried over anhydrous sodium sulfate, filtered, and concentrated under reduced pressure. The resulting residue was applied to a silica gel column with ethyl acetate/petroleum ether (80:20) as eluent. This resulted in 510 mg (48%) of 3,6-dibromo-1-(2,5,8,11-tetraoxatridecan-13-yl)-1,2-dihydroquinolin-2-one, compound 4c, as a yellow solid. LC-MS (ES, m/z): 494 [M+H]$^+$.

Step 2. Synthesis of 6-bromo-3-(4-phenylpiperazin-1-yl)-1-(2,5,8,11-tetraoxatridecan-13-yl)-1,2-dihydroquinolin-2-one, 4d Into a 25-mL round-bottom flask, purged and maintained with an inert atmosphere of nitrogen, was placed a solution of compound 4c (510 mg, 1.03 mmol, 1.00 equiv) in 1,4-dioxane (6 mL), 1-phenylpiperazine (334 mg, 2.06 mmol, 2.00 equiv), Pd(OAc)$_2$ (23 mg, 0.10 mmol, 0.10 equiv), 4,5-bis(diphenylphosphino)-9,9-dimethylxanthene (60 mg, 0.10 mmol, 0.10 equiv), Cs$_2$CO$_3$ (672 mg, 2.06 mmol, 2.00 equiv). The resulting solution was stirred overnight at 90° C., followed by dilution of the mixture with 20 mL of water. The resulting solution was extracted with 2×30 mL of ethyl acetate and the organic portions were combined, dried over anhydrous sodium sulfate, filtered, and concentrated under reduced pressure. The residue was applied to a silica gel column with ethyl acetate/petroleum ether (85:15) as eluent. This resulted in 390 mg (66%) of 6-bromo-3-(4-phenylpiperazin-1-yl)-1-(2,5,8,11-tetraoxatridecan-13-yl)-1,2-dihydroquinolin-2-one, compound 4d, as a yellow solid. LC-MS: (ES, m/z): 574 [M+H]$^+$.

Step 3. Synthesis of 6-[bis(4-chlorophenyl)(hydroxy)methyl]-3-(4-phenylpiperazin-1-yl)-1-(2,5,8,11-tetraoxatridecan-13-yl)-1,2-dihydroquinolin-2-one, 4e

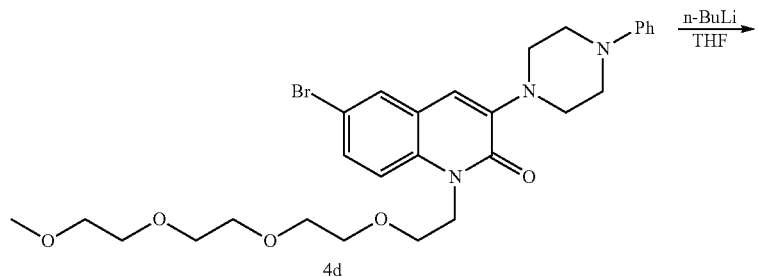

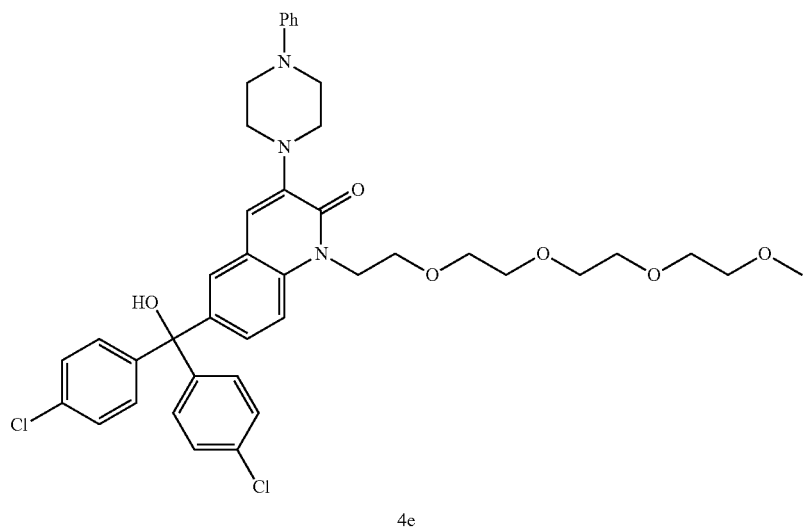

Into a 100-mL 3-necked round-bottom flask, purged and maintained with an inert atmosphere of nitrogen, was placed a solution of compound 4d (390 mg, 0.68 mmol, 1.00 equiv) in tetrahydrofuran (41 mL). A portion of n-BuLi (1.7 mL, 4.00 equiv, 1.6M) was then added dropwise with stirring at −78° C. To the reaction mixture was added bis(4-chlorophenyl)methanone (683 mg, 2.72 mmol, 4.00 equiv, dissolved in a minimum volume of THF) dropwise with stirring at −78° C. The reaction was slowly warmed to room temperature and quenched by the addition of 50 mL of saturated sodium bicarbonate solution. The resulting mixture was extracted with 2×100 mL of ethyl acetate and the organic layers were combined, dried over anhydrous sodium sulfate, filtered, and concentrated under reduced pressure. The residue was applied to a silica gel column with ethyl acetate/petroleum ether (80:20) as eluent. This resulted in 480 mg (95%) of 6-[bis(4-chlorophenyl)(hydroxy)methyl]-3-(4-phenylpiperazin-1-yl)-1-(2,5,8,11-tetraoxatridecan-13-yl)-1,2-dihydroquinolin-2-one, compound 4e, as yellow oil. LC-MS: (ES, m/z): 747 [M+H]$^+$.

Step 4. Synthesis of 6-[bis(4-chlorophenyl)methyl]-3-(4-phenylpiperazin-1-yl)-1-(2,5,8,11-tetraoxatridecan-13-yl)-1,2-dihydroquinolin-2-one, Cpd 24

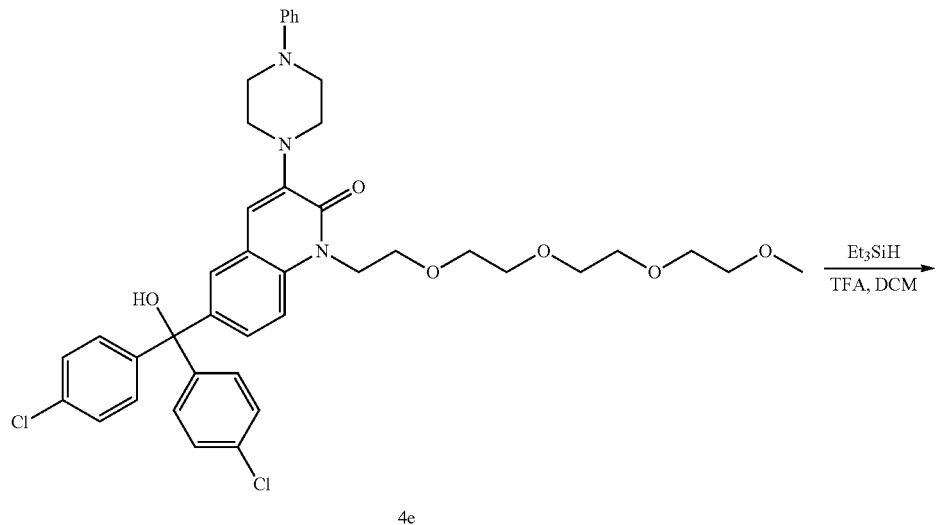

4e

Cpd 24

Into a 50-mL round-bottom flask, purged and maintained with an inert atmosphere of nitrogen, was placed a solution of compound 4e (480 mg, 0.64 mmol, 1.00 equiv) in dichloromethane (30 mL). To the solution was added Et$_3$SiH (0.408 mL, 4.00 equiv) dropwise with stirring at 0° C. Trifluoroacetic acid (1.2 mL, 25.00 equiv) was added dropwise with stirring at 0° C. The resulting solution was stirred for 3 h at room temperature. The reaction was then quenched by the addition of 100 mL of saturated sodium bicarbonate solution. The resulting solution was extracted with 2×100 mL of dichloromethane and the organic layers were combined, dried over anhydrous sodium sulfate, filtered, and the filtrate concentrated under reduced pressure. The crude product was purified by Prep-TLC with ethyl acetate as eluent. This resulted in 58.1 mg (12%) of 6-[bis(4-chlorophenyl)methyl]-3-(4-phenylpiperazin-1-yl)-1-(2,5,8,11-tetraoxatridecan-13-yl)-1,2-dihydroquinolin-2-one, compound 24, as a light yellow solid. LC-MS (ES, m/z): 730 [M+H]$^+$; $^1$H NMR (400 MHz, DMSO) δ: 7.53 (d, J=8.8 Hz, 1H), 7.39-7.41 (m, 4H), 7.32 (s, 1H), 7.22-7.26 (m, 2H), 7.14-7.17 (m, 6H), 6.99-7.01 (m, 2H), 6.81 (t, J=7.2 Hz, 1H), 5.74 (s, 1H), 4.45 (t, J=6.0 Hz, 1H), 3.67-3.69 (m, 2H), 3.53-3.55 (m, 2H), 3.27-3.49 (m, 17H), 3.20 (s, 3H).

Example 5

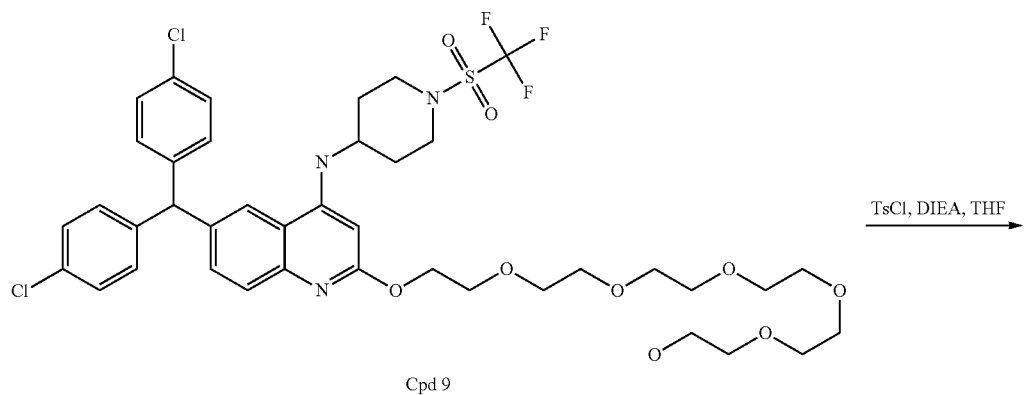

Cpd 9

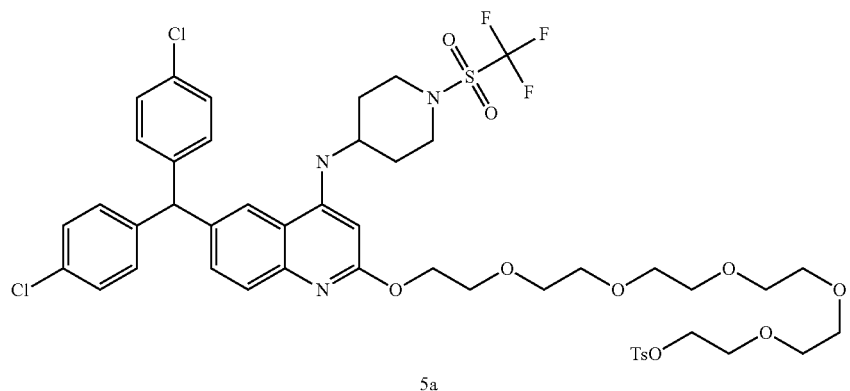

5a

Step 1. Synthesis of Compound 5a

To a solution of compound 9 prepared according to the method described from Example 1 (400 mg, 0.458 mmol) in THF (5 mL) was added TsCl (174.5 mg, 0.916 mmol) followed by DIEA (118.3 mg, 0.916 mmol). The resulting mixture was stirred at rt for 24 h. The reaction mixture was diluted with EtOAc and water. The organic portion was concentrated and purified by column chromatography on a silica gel column (80% EtOAc/heptanes) to give 260 mg of compound 5a. (ES, m/z): 1029.2, 1030.2, 1031.2 [M+H]+.

Step 2. Synthesis of Compound 11

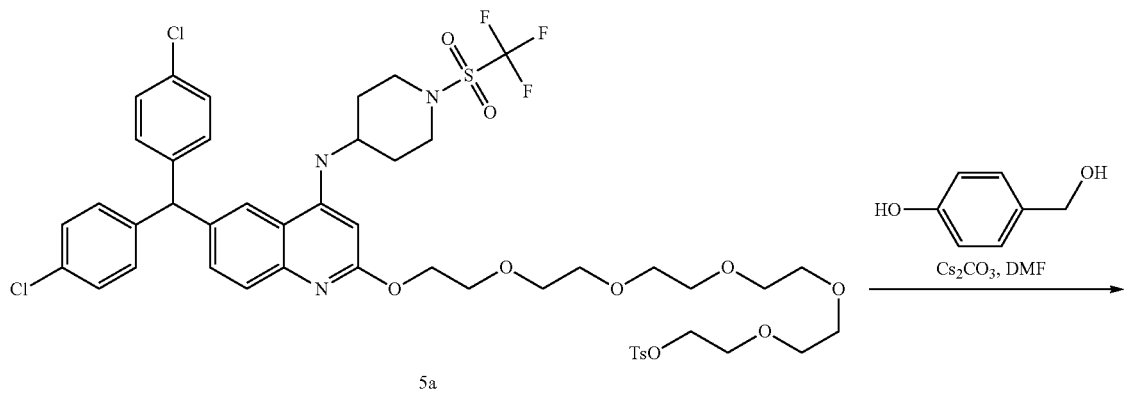

5a

-continued

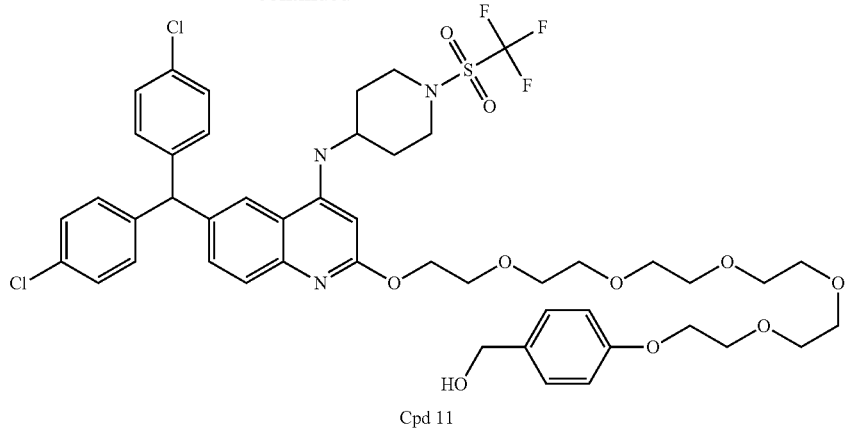

Cpd 11

A solution of compound 5a (200 mg) and 4-hydroxybenzyl alcohol (72 mg, 0.58 mmol) in the presence of $Cs_2CO_3$ (95 mg, 0.29 mmol) in DMF (1.5 mL) was heated to 90° C. overnight. The reaction was cooled to rt and diluted with EtOAc and water. The aqueous layer was extracted with EtOAc and the combined organic extracts were concentrated and purified by column chromatography on silica gel (100% EtOAc) to give 140 mg of compound 11. $^1$H NMR (CHLOROFORM-d) δ: 7.67 (d, J=8.6 Hz, 1H), 7.19-7.34 (m, 8H), 7.03 (d, J=8.6 Hz, 4H), 6.88 (d, J=8.6 Hz, 2H), 5.97 (s, 1H), 5.62 (s, 1H), 4.54-4.63 (m, 4H), 4.51 (br d, J=7.1 Hz, 1H), 4.04-4.18 (m, 2H), 3.97 (br d, J=12.6 Hz, 2H), 3.79-3.89 (m, 4H), 3.57-3.73 (m, 16H), 3.14-3.32 (m, 2H), 2.24 (br d, J=11.6 Hz, 2H), 1.83 (br t, J=5.6 Hz, 1H), 1.75 (s, 2H), 1.60 (br d, J=10.6 Hz, 2H); (ES, m/z): 981.3, 983.3 [M+H]$^+$.

Example 6

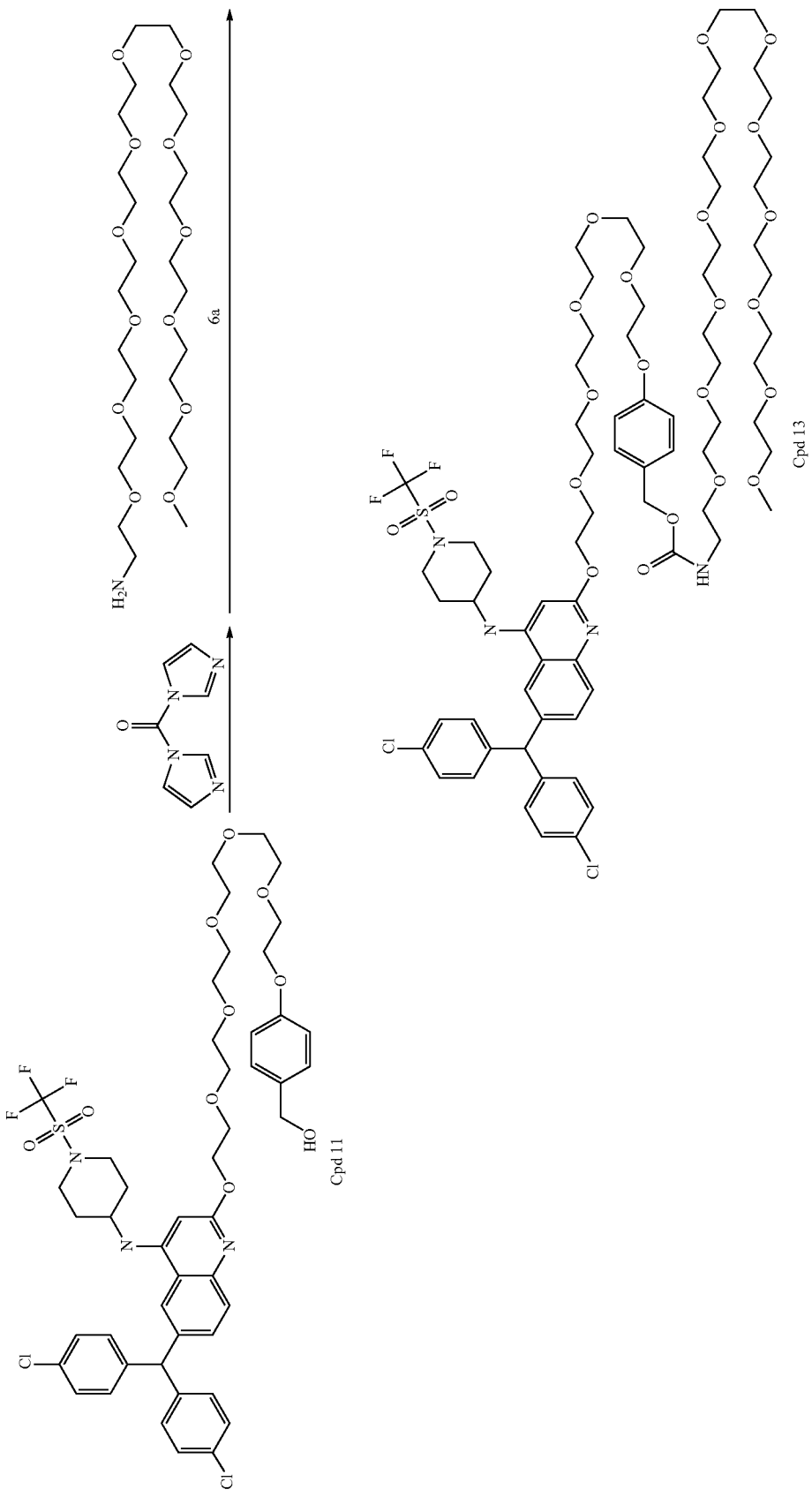

A mixture of compound 11 (39 mg, 0.0398 mmol) and di(1H-imidazol-1-yl)methanone (16 mg, 0.0994 mmol) in THF (1.5 mL) was stirred at rt for 1 h. PEG amine compound 6a (26.7 mg, 0.0477 mmol) was added to the reaction mixture followed by DIEA (0.0103 mL, 0.0596 mmol). The reaction was continuously stirred at rt for 36 h. The reaction was diluted with DCM and water. The organic layer was concentrated and purified by column chromatography on silica gel (5-8% MeOH/DCM) to give 30 mg of compound 13. $^1$H NMR (CHLOROFORM-d) δ: 7.67 (d, J=8.6 Hz, 1H), 7.21-7.31 (m, 8H), 7.03 (d, J=8.1 Hz, 4H), 6.87 (d, J=8.6 Hz, 2H), 5.98 (s, 1H), 5.63 (s, 1H), 5.36 (br s, 1H), 5.00 (s, 2H), 4.51-4.62 (m, 3H), 4.07-4.13 (m, 2H), 3.98 (br d, J=12.6 Hz, 2H), 3.85 (dt, J=12.9, 4.7 Hz, 4H), 3.46-3.73 (m, 62H), 3.35-3.38 (m, 5H), 3.16-3.29 (m, 2H), 2.25 (br d, J=11.6 Hz, 2H), 1.56-1.67 (m, 2H); (ES, m/z): 1565.4 [M+H]$^+$; 1587.5 [M+Na]$^+$.

Following the procedures described in Example 6 above, and substituting suitably selected reagents, starting materials and conditions as would be readily apparent to those skilled in the art, the following representative compound of the present invention was prepared.

| Cpd No. | Structure | Analytical data |
|---|---|---|
| 12 | 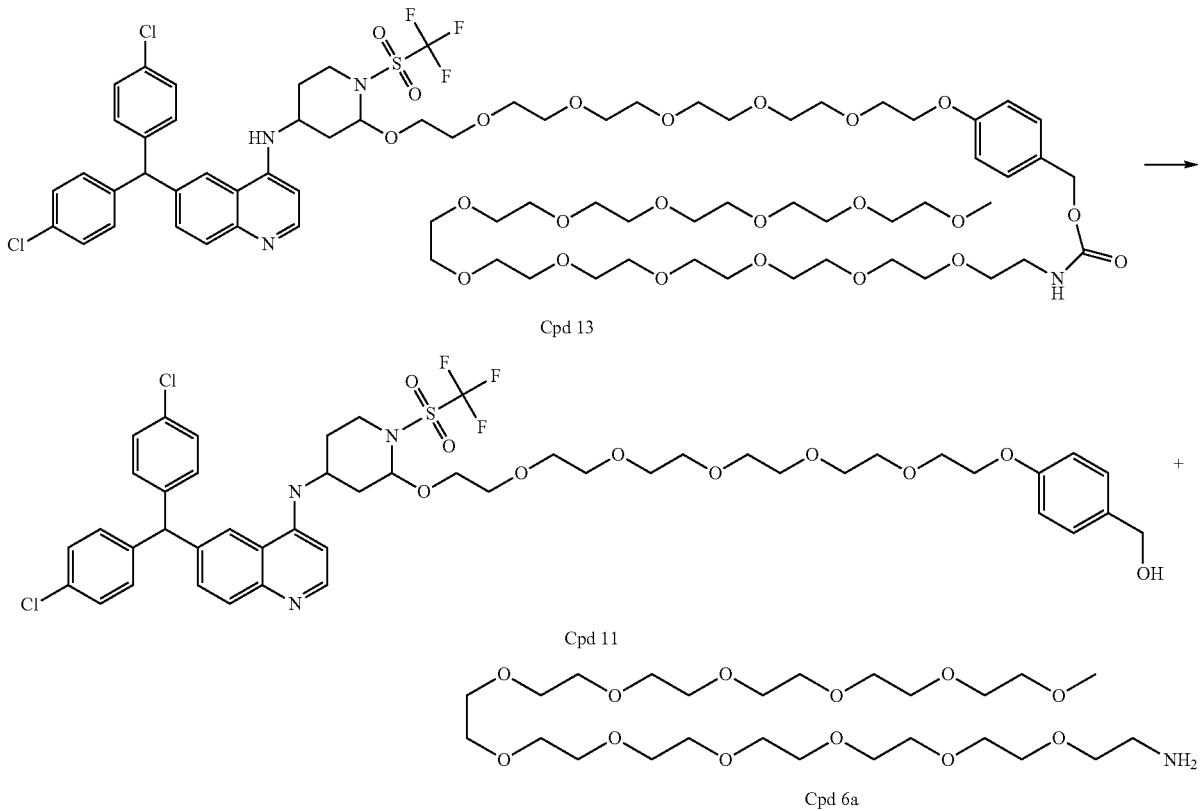 | (ES, m/z): 1422.4, 1424.5 [M + Na]$^+$; 700.3, 701.2 [M + H]$^+$/2 |

Example 7

Cleavage Reaction for Cleavable Linkers

Cpd 13

Cpd 11

Cpd 6a

Condition 1: Compound 13 (2 mg, 1.28 μmmol) was dissolved in 1 mL of MeCN and 0.35 mL of water. TFA (0.12 mL) was added to the mixture and the reaction was left at rt for 48 h. LCMS confirmed the consumption of compound 13 and formation of compound 11 and PEG amine.

Condition 2: Compound 13 (2 mg, 1.28 μmmol) was dissolved in 1 mL of MeCN and 0.35 mL of water. TFA (0.12 mL) was added to the mixture and the reaction was warmed to 45° C. for 18 h. LCMS confirmed the consumption of compound 13 and formation of compound 11 and PEG amine.

Example 8

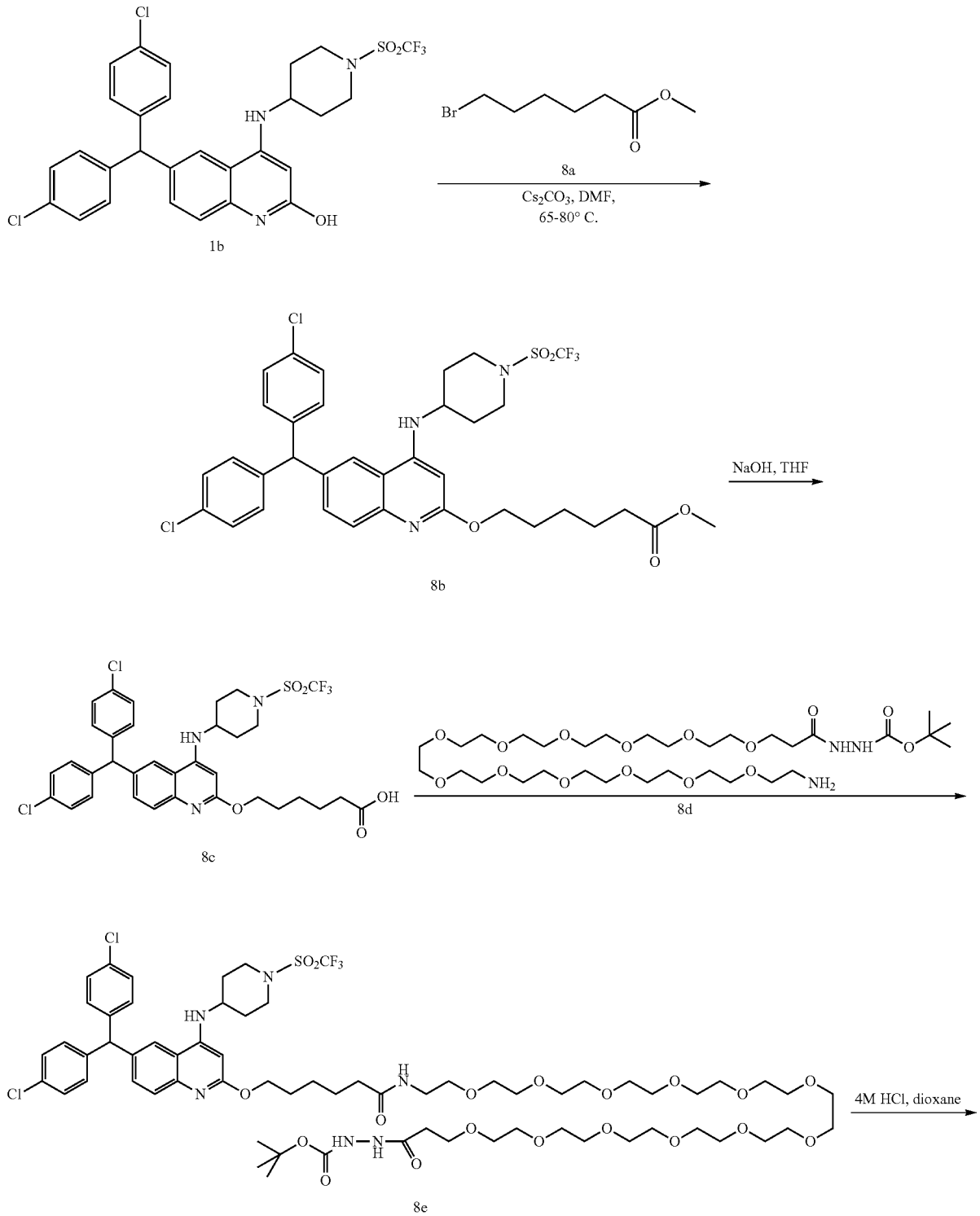

-continued

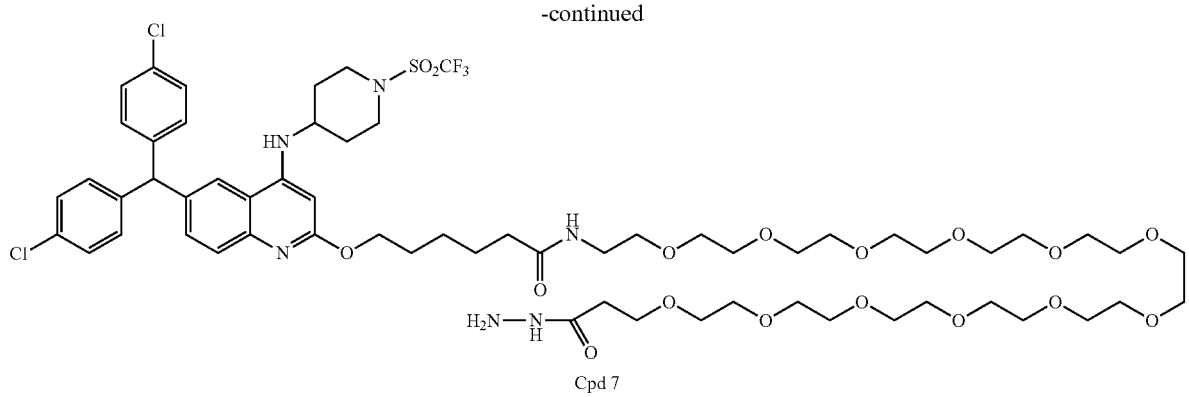
Cpd 7

Step 1. Synthesis of Compound 8b

To a solution of 6-(bis(4-chlorophenyl)methyl)-4-((1-(((trifluoromethyl)sulfonyl)piperidin-4-yl)amino)quinolin-2-ol, compound 1b, (300 mg, 0.491 mmol) in DMF (3 mL) was added $Cs_2CO_3$ (320 mg, 0.983 mmol) followed by methyl 6-bromohexanoate (8a) (154 mg, 0.737 mmol). The mixture was heated at 80° C. for 18 h. The reaction was partitioned between EtOAc and water. The aqueous layer was extracted with EtOAc. The combined organic layers were concentrated and purified by column chromatography on a silica gel column. Elution with 20% EtOAc/heptane gave 130 mg of methyl 6-((6-(bis(4-chlorophenyl)methyl)-4-((1-((trifluoromethyl)sulfonyl)piperidin-4-yl)amino)quinolin-2-yl)oxy)hexanoate, compound 8b. (ES, m/z): 738.2, 740.1 $[M+H]^+$.

Step 2. Synthesis of Compound 8c

To a solution of compound 8b (130 mg, 0.176 mmol) in THF (2 mL) was added 0.7 mL of NaOH (1N). The resulting mixture was vigorously stirred at rt for 5 h. The organic solvent was removed under reduced pressure and the residue was acidified using 1N HCl solution, followed by extraction with EtOAc. The organic portion was dried over anhydrous $Na_2SO_4$, filtered, and the filtrate concentrated to give 6-((6-(bis(4-chlorophenyl)methyl)-4-((1-((trifluoromethyl)sulfonyl)piperidin-4-yl)amino)quinolin-2-yl)oxy)hexanoic acid, compound 8c. Compound 8c was used for the next step without further purification. (ES, m/z): 724.0, 726.2. $[M+H]^+$.

Step 3. Synthesis of Compound 8e

To a solution of compound 8c (82 mg, 0.113 mmol) in DMF (0.8 mL) was added PEG amine 8d (89 mg, 0.124 mmol), HATU (55.9 mg, 0.147 mmol) and TEA (0.063 mL, 0.453 mmol). The reaction was stirred at rt for 3 h and partitioned between DCM and water. The aqueous layer was extracted with DCM. The combined organic extracts were concentrated and purified by column chromatography on silica gel (5-8% MeOH/DCM) to give tert-butyl 49-((6-(bis (4-chlorophenyl)methyl)-4-((1-(((trifluoromethyl)sulfonyl) piperidin-4-yl)amino)quinolin-2-yl)oxy)-4,44-dioxo-7,10, 13,16,19,22,25,28,31,34,37,40-dodecaoxa-2,3,43-triazanonatetracontan-1-oate, compound 8e. (ES, m/z): 1438.5, $[M+H]^+$, 1462.5 $[M+Na]^+$.

Step 4. Synthesis of Compound 7

A mixture of compound 8e (98 mg) in 0.5 mL of 4M HCl in dioxane was stirred at rt for 2 h and then concentrated. The residue was titrated with diethyl ether, the resultant solid was collected by filtration, and then dried under reduced pressure to give compound 7. $^1H$ NMR (DMSO-$d_6$) δ: 10.81-10.88 (d, J=4 Hz, 1H), 8.39 (br s, 1H), 7.88-7.92 (m, 1H), 7.68 (d, J=9.1 Hz, 1H), 7.50-7.54 (m, 1H), 7.42 (d, J=8.6 Hz, 4H), 7.14 (d, J=8.6 Hz, 4H), 6.34 (s, 1H), 5.77 (s, 1H), 4.44 (br t, J=6.1 Hz, 2H), 4.15-4.24 (m, 1H), 3.93 (br d, J=10.6 Hz, 2H), 3.63-3.68 (m, 2H), 3.47-3.51 (m, 48H), 3.16-3.33 (m, 2H), 2.65-2.68 (m, 1H), 2.44-2.48 (m, 2H), 2.31-2.33 (m, 1H), 2.07-2.14 (m, 4H), 1.69-1.85 (m, 4H), 1.54-1.62 (m, 2H), 1.39-1.48 (m, 2H); (ES, m/z): 1340.4, $[M+H]^+$; 669.3, 670.2 $[M+H]^+/2$.

Following the procedures described in Example 8 above, and substituting suitably selected reagents, starting materials and conditions as would be readily apparent to those skilled in the art, the following representative compounds of the present invention were prepared.

| Cpd No. | Structure | Analytical data |
|---|---|---|
| 6 | ![structure] | $^1H$ NMR (CHLOROFORM-d) δ: 7.67 (d, J = 8.6 Hz, 1H), 7.23-7.30 (m, 6H), 7.03 (d, J = 8.1 Hz, 4H), 6.16 (br s, 1H), 5.91 (s, 1H), 5.63 (s, 1H), 4.51 (d, J = 7.6 Hz, 1H), 4.39 (t, J = 6.8 Hz, 2H), 4.00 (br d, J = 12.6 Hz, 2H), 3.53-3.65 (m, 46H), 3.45 (q, J = 5.2 Hz, 2H), 3.38 (s, 3H), 3.28 (br t, J = 10.4 Hz, 2H), 2.19-2.31 (m, 4H), 1.59-1.84 (m, 6H), 1.46-1.55 (m, 2H); (ES, m/z): 1266.4, 1268.4, 1270., $[M + H]^+$; 634.2 $[M + H]^+/2$. |

| Cpd No. | Structure | Analytical data |
|---|---|---|
| 12 | 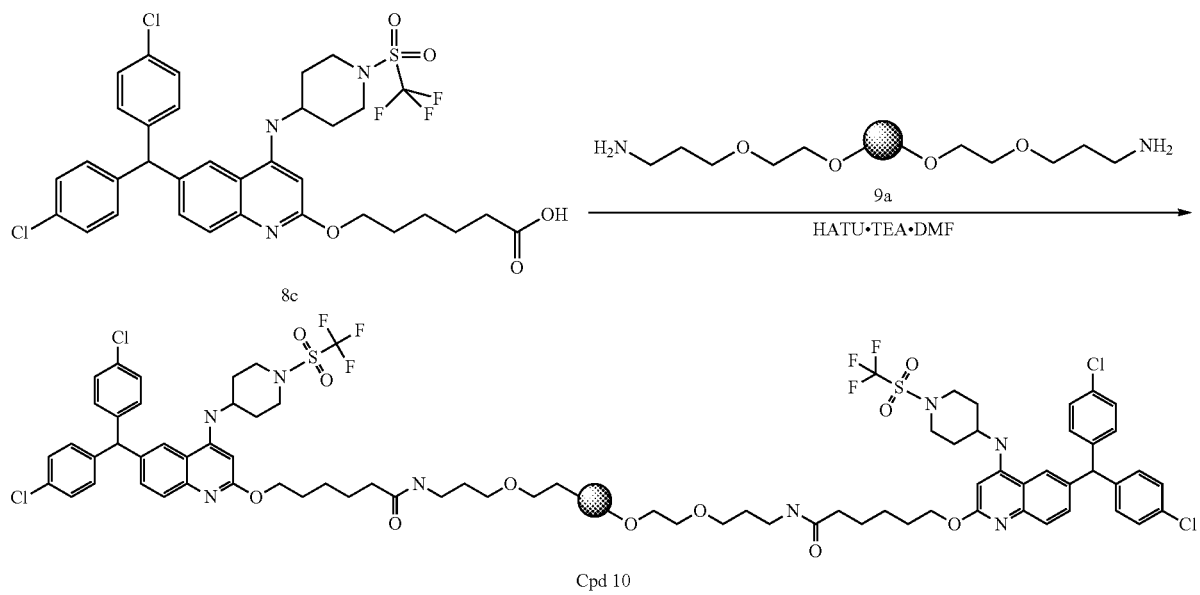 | (ES, m/z): 1422.4, 1424.5 [M + Na]+; 700.3, 701.2 [M + H]+/2 |

Example 9

To a solution of 6-(((6-(bis(4-chlorophenyl)methyl)-4-((1-((trifluoromethyl)sulfonyl)piperidin-4-yl)amino)quinolin-2-yl)oxy)hexanoic acid, cpd 8c, (50 mg, 0.069 mmol) in a mixed solvent (2 mL, DMF:DCM=1:1) was added PEG diamine 9a (Sunbright DE-200PA, 633.07 mg, 0.03 mmol) followed by HATU (28.5 mg, 0.075 mmol) and DIEA (0.021 mL, 0.12 mmol). The mixture was stirred at rt for 3 h before concentration of the reaction mixture. Purification by HPLC/ELSD on a C18 column (30-80% MeCN/H$_2$O with each solvent containing 0.1% TFA, 30 mL/min, 20 min). The product fractions were collected and combined. The organic solvent was removed and the resulting aqueous solution was neutralized by saturated aqueous NaHCO$_3$, followed by extraction three times with DCM. The combined organic extracts were dried over anhydrous Na$_2$SO$_4$, filtered, and the filtrate was concentrated to give compound 10 as a white foam. MALDI Tof, avg. mass: 22417.

Following the procedures described in Example 9 above, and substituting suitably selected reagents, starting materials and conditions as would be readily apparent to those skilled in the art, the following representative compounds of the present invention were prepared.

| Cpd No. | Structure | Analytical data |
|---|---|---|
| 14 | 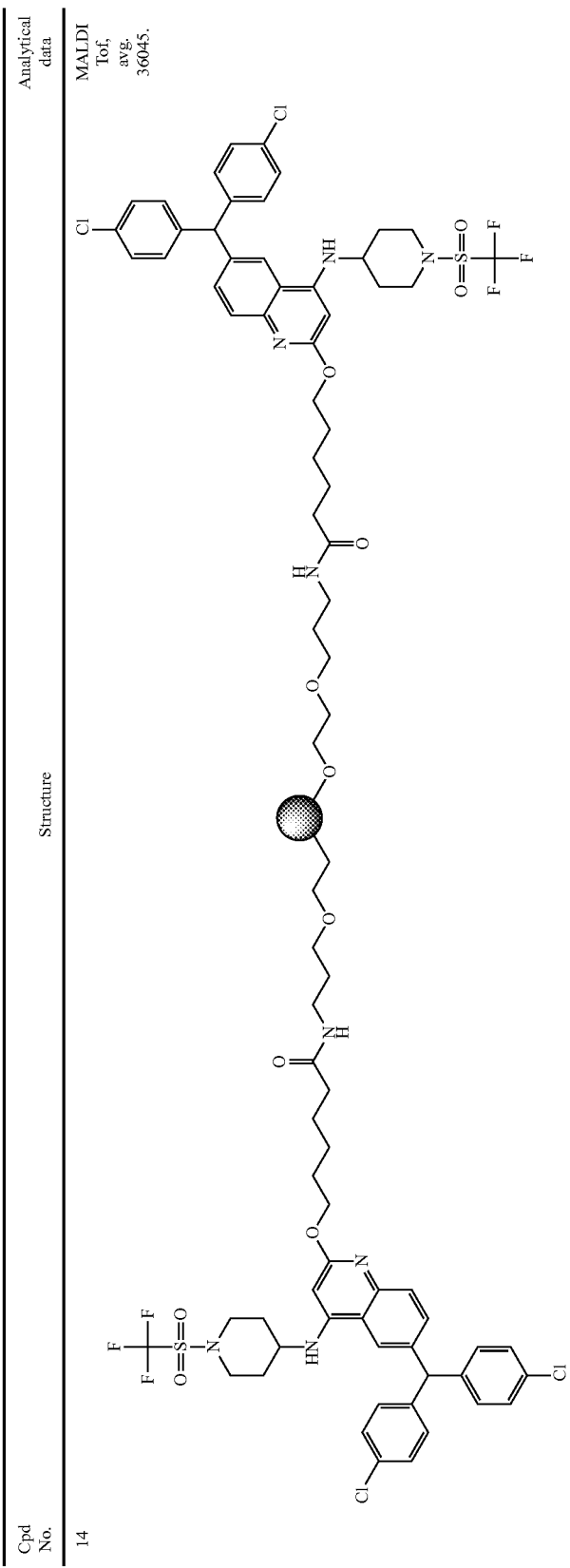 = 30 kD PEG | MALDI Tof, avg. 36045. |
| 18 | 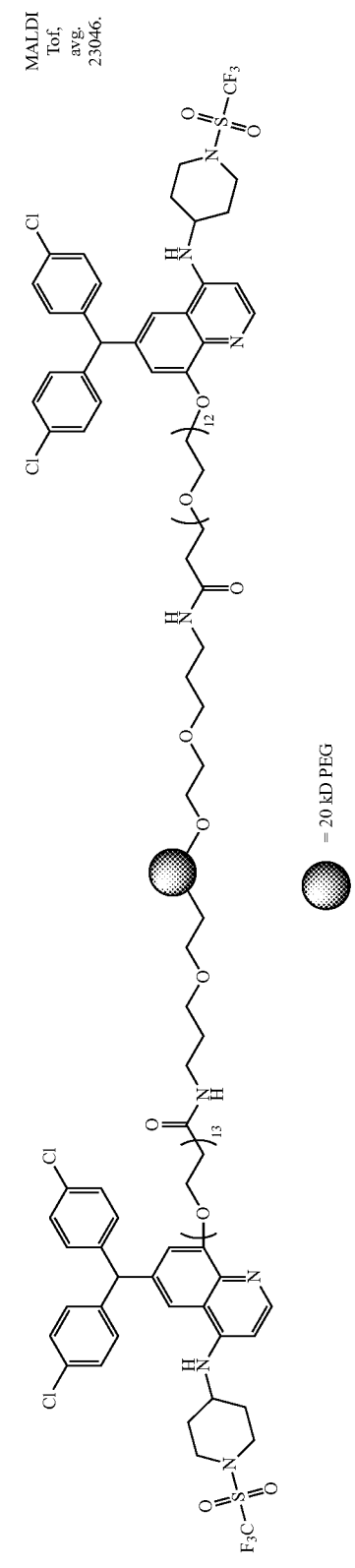 = 20 kD PEG | MALDI Tof, avg. 23046. |

-continued
| Cpd No. | Structure | Analytical data |
|---|---|---|
| 19 | 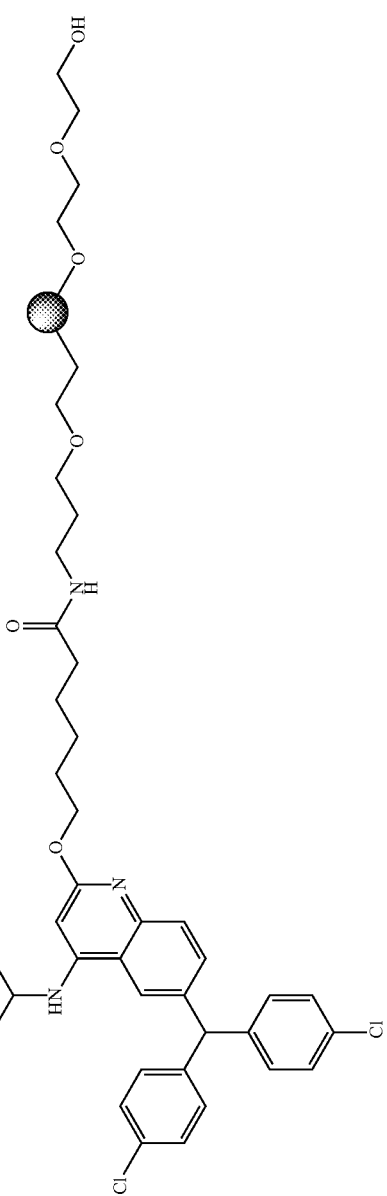  = 20 kD PEG | MALDI Tof, avg. 21204. |

Example 10

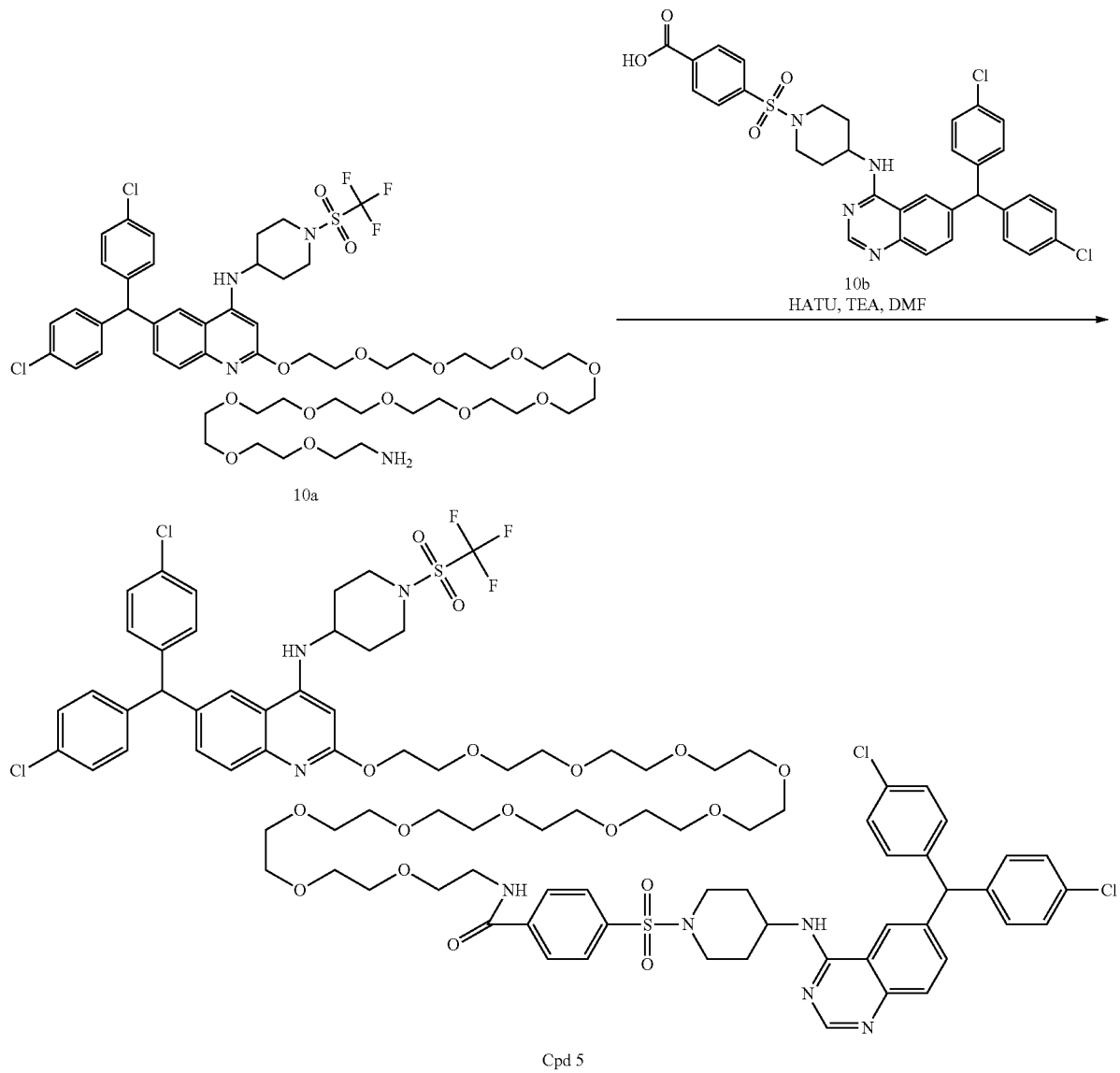

To a solution of compound 4 2-((35-amino-3,6,9,12,15,18,21,24,27,30,33-undecaoxapentatriacontyl)oxy)-6-(bis(4-chlorophenyl)methyl)-N-(1-((trifluoromethyl)sulfonyl)piperidin-4-yl)quinolin-4-amine (35 mg, 0.0298 mmol) in DMF (0.8 mL) was added 4-((4-((6-(bis(4-chlorophenyl)methyl)quinazolin-4-yl)amino)piperidin-1-yl)sulfonyl)benzoic acid, 10b, (18.4 mg, 0.0284 mmol), HATU (14.0 mg, 0.0369 mmol) and TEA (0.0197 mL, 0.142 mmol). The reaction was stirred at rt for 3 h and diluted with EtOAc and water. The aqueous layer was extracted with EtOAc. The combined organic extracts were concentrated and purified by column chromatography on silica gel (5-8% MeOH/DCM) to give 25 mg of compound 5. (ES, m/z): 883.3, 884.2 [M+H]$^+$/2; 1787.3, 1789.4, 1792.4 [M+Na]$^+$.

BIOLOGICAL EXAMPLES $CB_1$ and $CB_2$ receptors are $G_i$-coupled GPCR. Activation of $CB_1$ and $CB_2$ receptors results in a decrease in cAMP production. An inverse agonist of the $CB_1$ or $CB_2$ receptor results in the opposite effect, an increase of cAMP production. The principle of this assay is based on HTRF® technology (Homogeneous Time-Resolved Fluorescence). The method is a competitive immunoassay between native cAMP produced by cells and the cAMP labeled with the fluorophore d2. The tracer binding is quantified by a Mab anti-cAMP labeled with Eu3+TBP-NHS Cryptate (supplied as part of the assay kit). The specific signal (i.e. energy transfer) is inversely proportional to the concentration of cAMP in the standard or sample.

In Vitro Assay

Biological Example 1: CB-1 and CB-2

Preparation of Cells.
Human CB (Cannabinoid receptor 1) was stably transfected in HEK-293 cells (DiscoveRx, cat: 93-0200C1).

Human CB$_2$R (Cannabinoid receptor 2) was stably transfected in HEK-293 cells (DiscoveRx, cat: 93-0201C1). Cell cultures were maintained in media: DMEM (Invitrogen Cat#12430-054) supplemented with 10% HI FBS (Invitrogen Cat#16140-071), 1% L-glutamine (Invitrogen Cat#25030-081), 0.2 mg/mL Hygromycin B (Invitrogen Cat#10687-010), 600 μg/mL G418 (Invitrogen Cat#10131-035), and 1× Penn/Strep (Invitrogen 15140-122). After cell expansion, aliquots were cryo-stored in media containing 5% DMSO (Pierce Cat#20684).

Plating Cells from Cryostore.

One day prior to experiments media was warmed to 37° C. and the cryo-stored cells were thawed in a 37° C. water bath. The cells were then added to media (10× volume) and the mixture was centrifuged at 1000 RPM for 5 min. The supernate was removed and the cells were re-suspended in media. A sample of the cell suspension was evaluated on a Cedex XS automated cell counter (Innovatis Systems) to determine viable cells/mL. Additional media was added to the cells to achieve a final cell density of 4E5 cells/mL. The cells were then plated into 384 well PDL white solid bottom plates (Greiner, Cat#781945) at 20 μL per well using a Multidrop (Thermo Scientific). Cells were removed from Row P (location of cAMP standards). Two columns of cells were plated into a clear bottom 384 well PDL coated plate (Greiner, Cat#781944) to view confluence the day of the assay. The cell plates were lidded and stored for 15 minutes in a hood, then transferred to an incubator (37° C., 5% CO$_2$, 95% humidity) overnight.

Preparation of Compound Plates.

Test compounds were solubilized in DMSO at 10 mM or for pegylated compounds 4 or 1 mM. DMSO was added to all wells of 384 well V bottom polystyrene plate (Greiner, Cat#781280) except to columns 1 and 13, rows O and P and wells M13-M23 and N13-N23. Test compounds (60 μL, 10 mM or 4 mM or 1 mM) were added to Column 1 and 13 (A1 through N1 and A13 through L13). Test compounds were serially diluted ⅓ by transferring and mixing 20 μL sample with 40 μL DMSO. This process resulted in a plate of 26 compounds, 11 doses per compound, 10 mM to 0.17 μM (4 mM-0.07 μM or 1 mM-0.017 μM for pegylated compounds).

Preparation of Control Plate.

DMSO (40 μL) was added to wells of 384 well V bottom polystyrene plate: O2 through O11, M14 through M23, N14 through N23, and O14 through O23. AM630 (also known as [6-iodo-2-methyl-1-[2-(4-morpholinyl)ethyl]-1H-indol-3-yl](4-methoxyphenyl)-methanone, Cayman Chemical, Cat#10006974) (60 μL, 10 mM) was added to O1; and 1-(2,4-dichlorophenyl)-7-[(4-fluorophenyl)methylene]-4,5,6,7-tetrahydro-N-1-piperidinyl-1H-indazole-3-carboxamide (60 μL, 10 mM) was added to N13. The control was serially diluted ⅓ by transferring and mixing 20 μL sample with 40 μL DMSO. This process resulted 11 doses per control, 10 mM to 0.17 μM.

cAMP Assay Protocol.

Cells plated the day prior to the assay in clear bottom plates were viewed on an inverse microscope to ensure confluency in the range of 60-75%. The following mixtures and buffer solutions were prepared: (a) Buffer 1: HBSS (Mediatech Cat#21-023-CV) with 5 mM HEPES (1 mM stock, Gibco BRL Cat#15630-056) and 0.1% BSA (7.5% stock, Invitrogen Cat#15260-037); (b) Buffer 2: 0.5 mM IBMX (200 mM stock in DMSO, Sigma 15879) in Buffer 1; (c) 1 μM cAMP Standard (50 μM stock, Perkin Elmer Cat# AD0262) diluted in Buffer 2 and serially diluted in Buffer 2, 12 doses @ ½ dilutions resulting in a dose range of 1 μM to 0.5 nM; (d) d2 labelled cAMP (CisBio HTRF Detection Kit Cat #62AM4PEB reconstituted with 6 mL d-H$_2$O) diluted ½0 with lysis buffer (CisBio HTRF Detection Kit Cat #62AM4PEB); (e) anti-cAMP (CisBio HTRF Detection Kit Cat # 62AM4PEB reconstituted with 5 mL d-H$_2$O) diluted ½0 with lysis buffer (CisBio HTRF Detection Kit Cat #62AM4PEB); and (f) Forskolin (Sigma Cat# F6886, 10 mM in DMSO) diluted first in DMSO to 1 mM and then to 1.5 μM in Buffer 2.

A FLEXDROP (Perkin Elmer) was cleaned with ethanol then water, and primed with Buffer 2. A 384 well V bottom polypropylene plate containing d2 labelled cAMP and a second 384 well V bottom polypropylene plate containing anti-cAMP was prepared (50 per well). Media was "dumped" from the cell plate and 30 μL Buffer 1 was added to each well using a Multidrop. The content of the cell plate was again "dumped" and 10 Buffer 2 was added to each well using a Flexdrop. 12.5 nL test compound dilutions or control compound dilutions (10 mM to 0.17 μM-0.07 μM or 1 mM-0.017 for pegylated compounds) were added to the cell plate using an ECHO 555 (Labcyte). The cell plate was mixed (Speed 6, Lab-Line Instruments Titer Plate Shaker) and centrifuged (1000 RPMs, 1 min). Using the Flexdrop, 2 μL additions were made into the cell plate: Buffer 2 was added to Column 24; and, 1.5 μM Forskolin was added to columns 1 through 23. Final volume of the cell plate was 12 μL with 250 nM Forskolin in all wells except column 12, and serial dilutions of test compound or control ranging from 10 μM to 0.17 nM or 4 μM to 0.07 nM or 1 μM to 0.017 nM for pegylated compounds. The cell plate was again mixed (speed 6) and centrifuged (1000 RPMs, 1 min). The cell plate was incubated for 30 minutes at room temperature (~27° C.). The contents of row P were removed and the cAMP standard dilutions were added in duplicate to Row P (P1-12 and P13-24). After incubation, 6 μL d2 labelled cAMP and 6 μL of Anti-cAMP were added to all wells of the cell plate using a BioMek FX (Beckman Coulter). The cell plate was again mixed (speed 6) and centrifuged (1000 RPMs, 1 min) and was incubated for 60 min in the dark at room temp (~27° C.).

After this final incubation, the cell plate was read in HTRF mode (fluorescence at 665 nm and 620 nm) on an Envision plate Reader (Perkin Elmer). The Envision reader outputs a ratio of channel 1/channel 2 fluorescence×10,000 (Normalized signal (NS)). Amount of cAMP in nM was calculated for each well (based on NS) from a cAMP standard curve located on each plate (at P1-12 and P13-24). EC$_{50}$ values were determined from a 4-point fit (Hill equation) of a single 11-point compound dosing. Hill slope was fixed at 1.0. The bottom of the dose response curve was fixed because it was always the same as that of the control wells containing vehicle (DMSO) instead of compound. The top of the dose response curve was floated unless a plateau was not reached.

Representative compounds of Formula (I) and Formula (II) of the present invention were tested for activity against the CB-1 and CB-2 receptors, according to assay protocol as outlined in Biological Example 1, with EC$_{50}$ results (in micromolar) as listed in Table BIO-1, below. Where a compound was tested more than once, the result presented below represents a mean of the individual measurements.

TABLE BIO-1

CB-1 and CB-2 Biological Activity
of Compounds of Formula (XX)

| Cpd No. | CB1 EC$_{50}$ (μM) | CB2 EC$_{50}$ (μM) |
|---|---|---|
| 1 | 0.056 | 7.4 |
| 2 | 0.48 | 5.57 |
| 3 | 1.8 | >10 |
| 4 | 0.036 | 4.3 |
| 5 | 2.08 | >10 |
| 6 | 0.019 | 3 |
| 7 | 0.033 | 1.26 |
| 8 | 0.052 | >10 |
| 9 | 0.15 | >10 |
| 10 | 0.075 | 3.6 |
| 11 | 0.061 | 3.11 |
| 12 | 0.094 | 5.4 |
| 13 | 0.24 | 4.06 |
| 14 | 0.069 | 0.71 |
| 15 | 0.068 | 1.9 |
| 16 | 0.46 | 2.25 |
| 17 | 0.077 | 0.74 |
| 18 | 0.5 | >4 |
| 19 | 0.24 | >4 |
| 20 | 0.047 | 3.3 |
| 21 | 0.39 | >10 |
| 22 | 4.91 | >10 |
| 23 | 10 | >10 |
| 24 | 0.35 | 5.51 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of Formula (I)

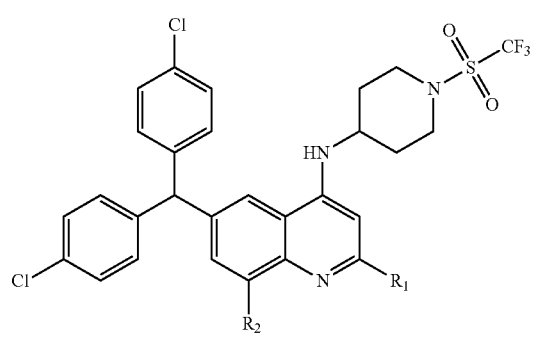

Formula (I)

wherein

R$_1$ and R$_2$ are selected from the group consisting of i) hydrogen, ii)

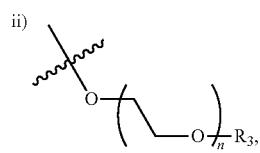

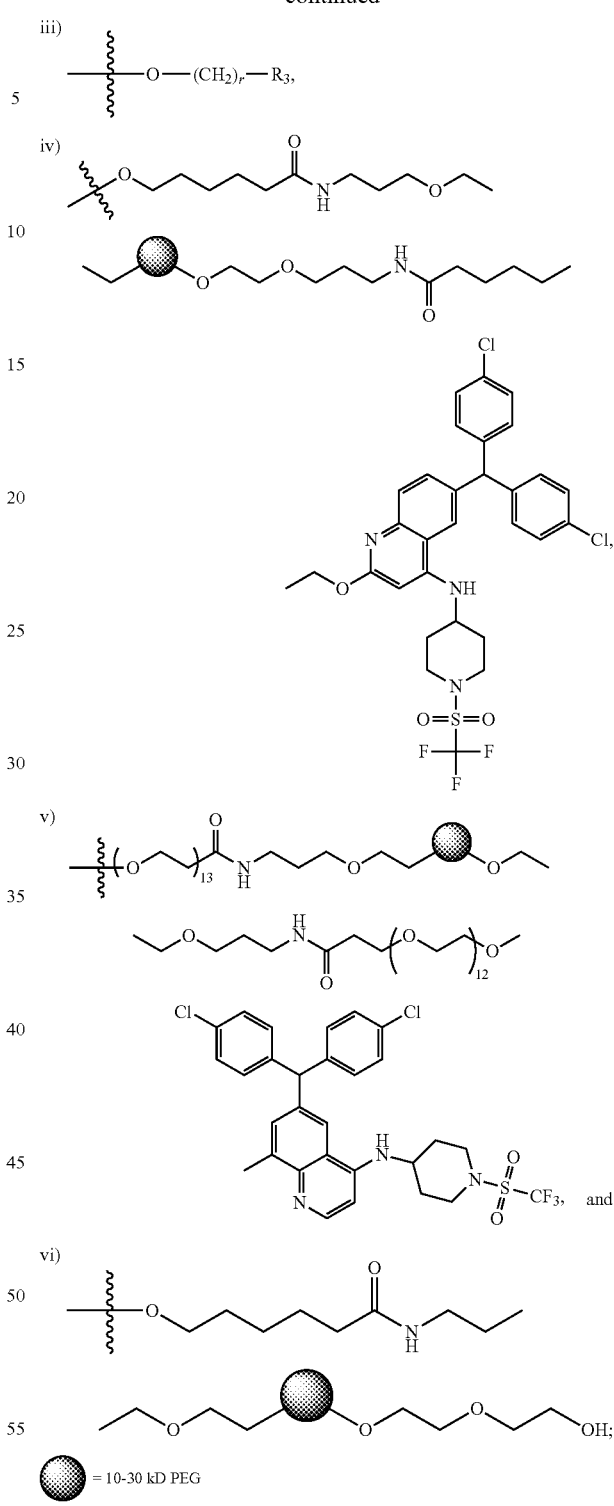

= 10-30 kD PEG such that one of R$_1$ and R$_2$ is hydrogen in every instance;

R$_3$ is a substituent selected from the group consisting of methyl, C$_{1-4}$alkoxycarbonylamino-ethyl, C$_{1-4}$alkoxycarbonyl-ethyl, carboxyethyl, aminoethyl, hydrogen, 4-hydroxymethylphenyl, or a substituent selected from the group consisting of 3a

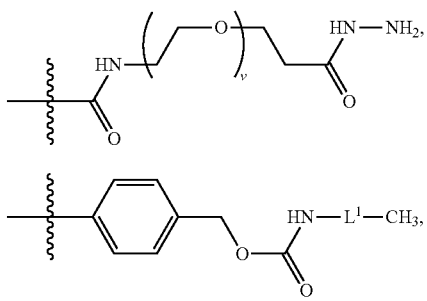

3b wherein L¹ is selected from

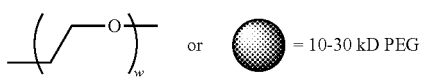

3c

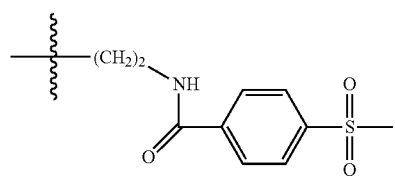

-continued
and

3d

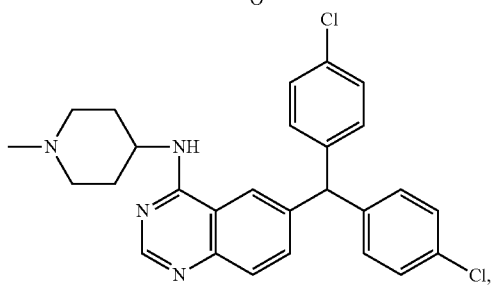

n is an integer from 2 to 36;
v is an integer from 1 to 12;
r is an integer from 2 to 7;
w is an integer from 1 to 24;
g is an integer from 1 to 24;
or an enantiomer, diastereomer, or pharmaceutically acceptable salt form thereof.

2. The compound of claim 1 wherein $R_1$ and $R_2$ are selected from the group consisting of
i) hydrogen,
ii)

iii)

r is an integer from 2 to 5;

iv)

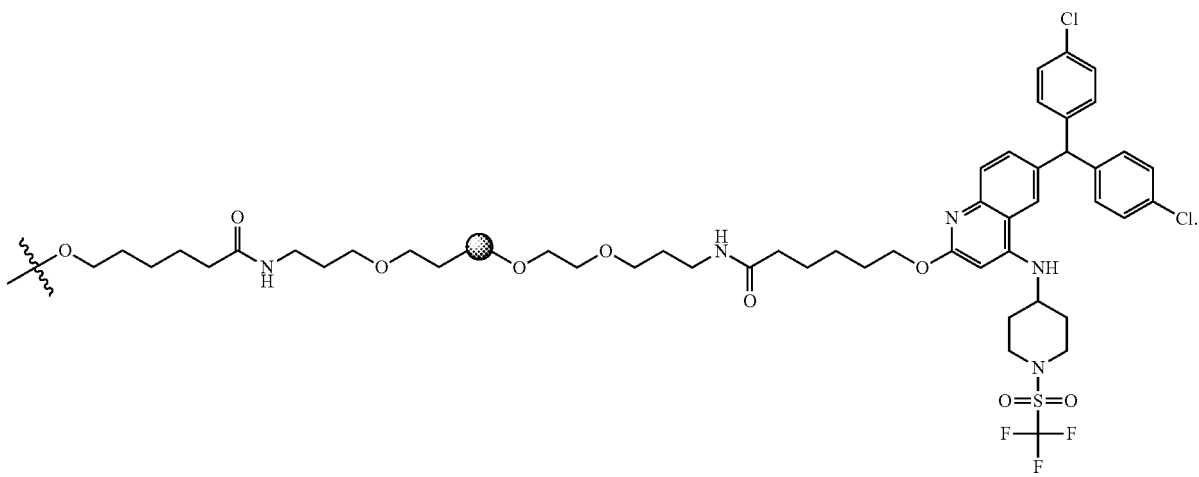

And
v)
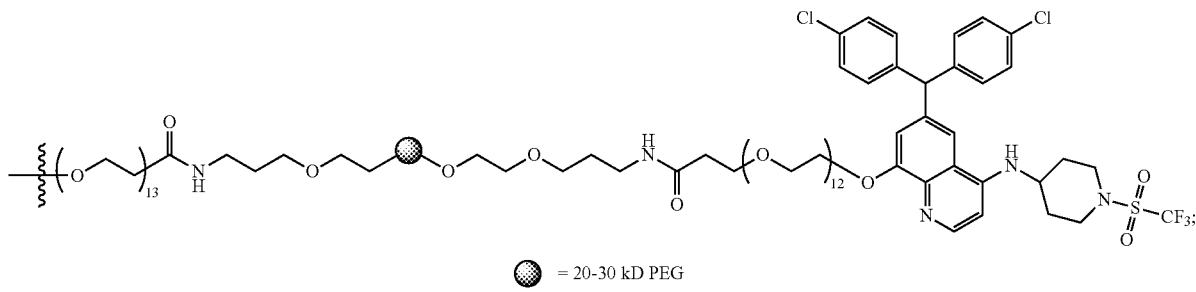
● = 20-30 kD PEG
such that one of $R_1$ and $R_2$ is hydrogen in every instance.
3. The compound of claim 2 wherein r is an integer from 5 to 7.
4. The compound of claim 1 wherein $R_1$ and $R_2$ are selected from the group consisting of
i) hydrogen,
ii)
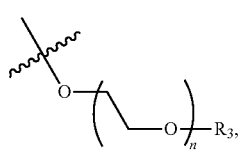
wherein n is an integer selected from the group consisting of
ii) 3, 4, 6, 7, and 11;
iii)
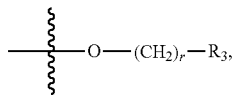
wherein r is 5;
iv)
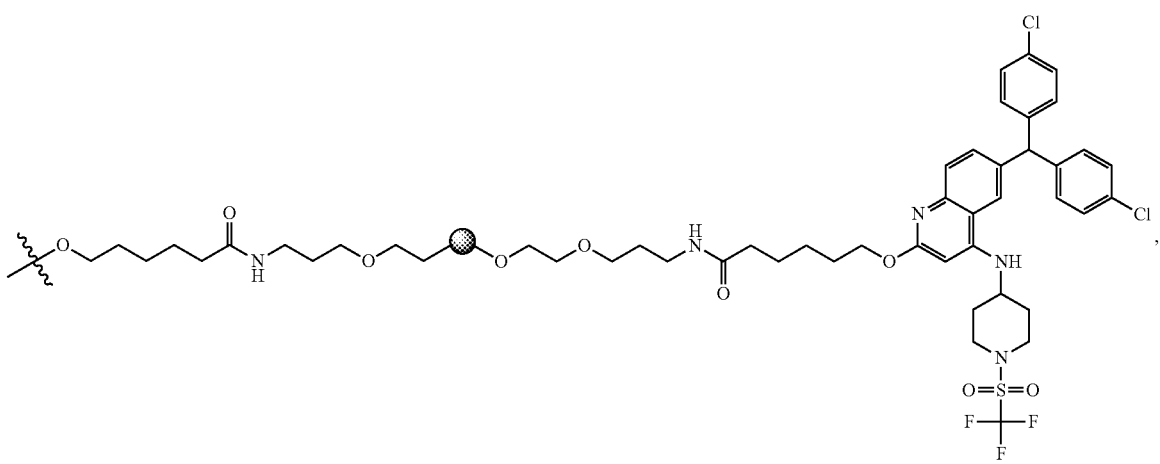
● = 20-30 kD PEG v)
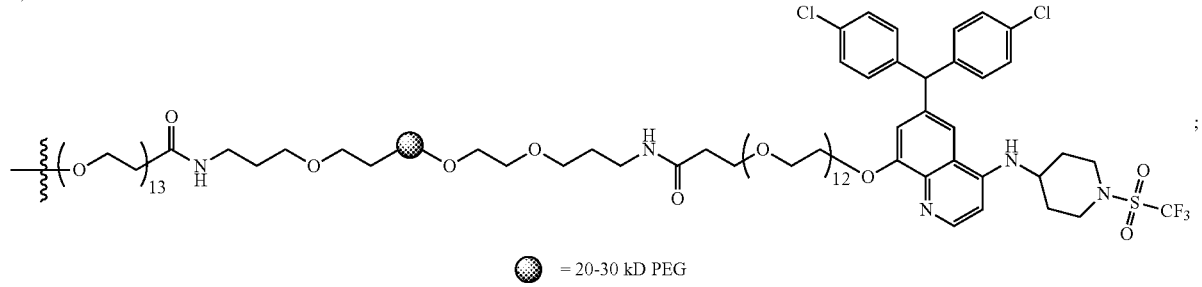
= 20-30 kD PEG
and
vi)
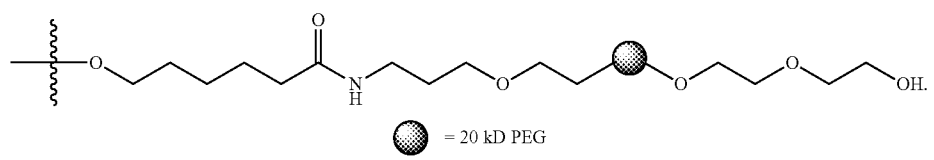
= 20 kD PEG
5. The compound of claim 1 wherein $R_3$ is a substituent selected from the group consisting of hydrogen, methyl, t-butoxycarbonylamino-ethyl, t-butoxycarbonyl-ethyl, aminoethyl, carboxyethyl, 4-hydroxymethylphenyl, or a substituent selected from the group consisting of
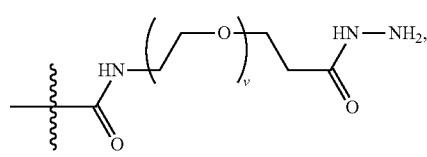
wherein v is 9 or 12;
3a
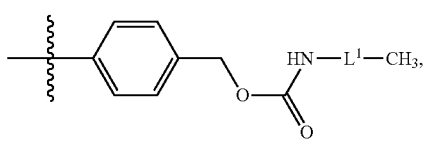
wherein $L^1$ is
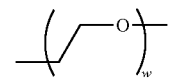
and w is 12;
3b
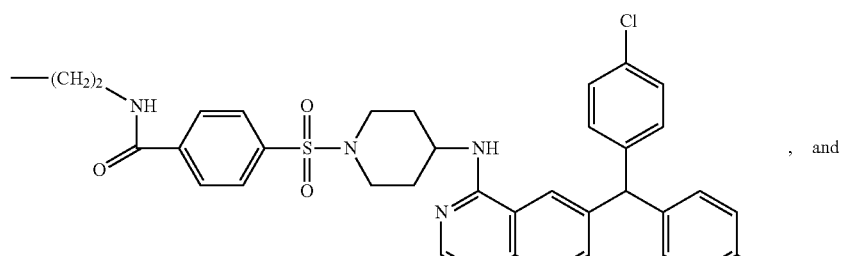
, and
3c
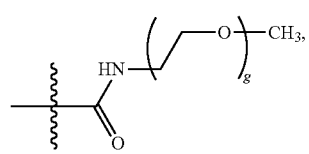
wherein g is 12.
3d 6. The compound of claim 1 wherein R₃ is a substituent selected from the group consisting of hydrogen, methyl, t-butoxycarbonylamino-ethyl, t-butoxycarbonyl-ethyl, aminoethyl, carboxyethyl, 4-hydroxymethylphenyl, or a substituent selected from the group consisting of

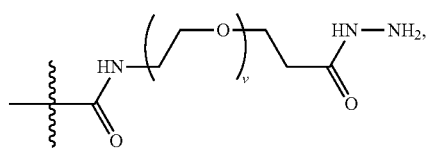

wherein v is 9 or 12;

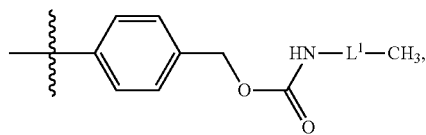

wherein L¹ is

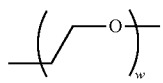

and w is 12;

7. The compound of claim 1 wherein n is an integer from 3 to 12.

8. The compound of claim 6 wherein v is an integer from 5 to 12.

9. A compound of Formula (I)

Formula (I)

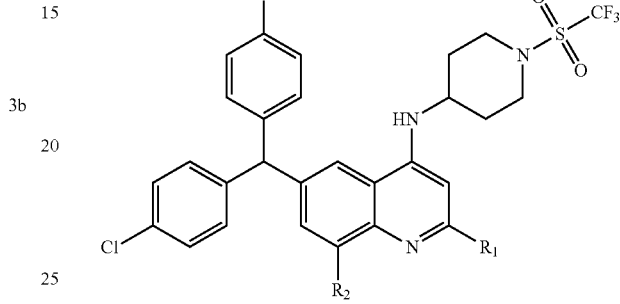

and

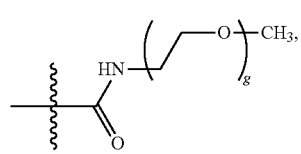

wherein g is 12.

wherein
R₁ and R₂ are selected from the group consisting of
i) hydrogen,
ii)
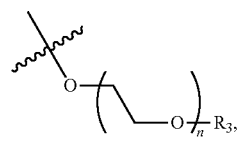
iii)
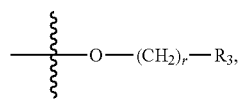
iv)
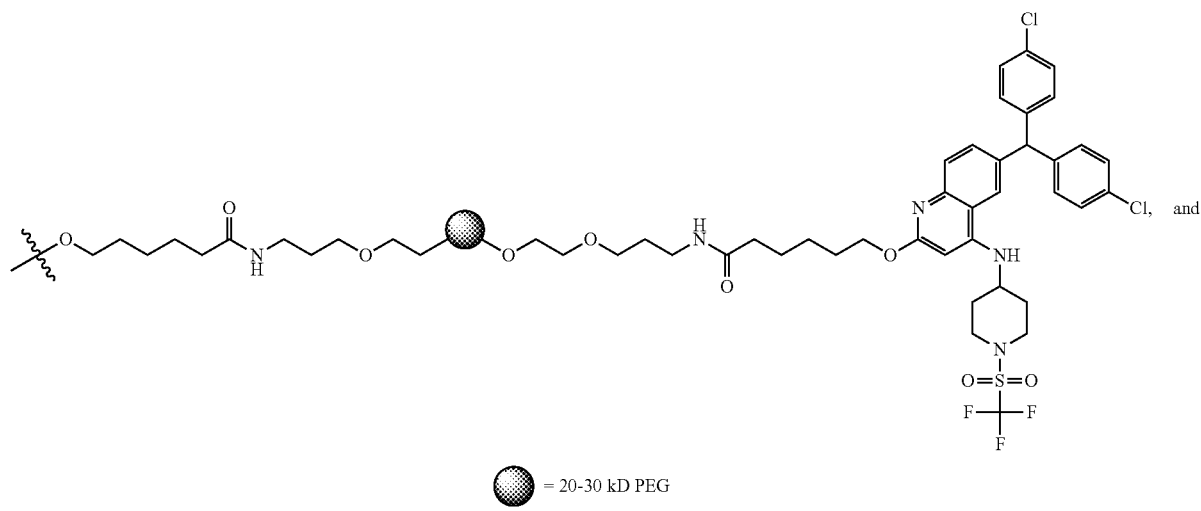
= 20-30 kD PEG
v)
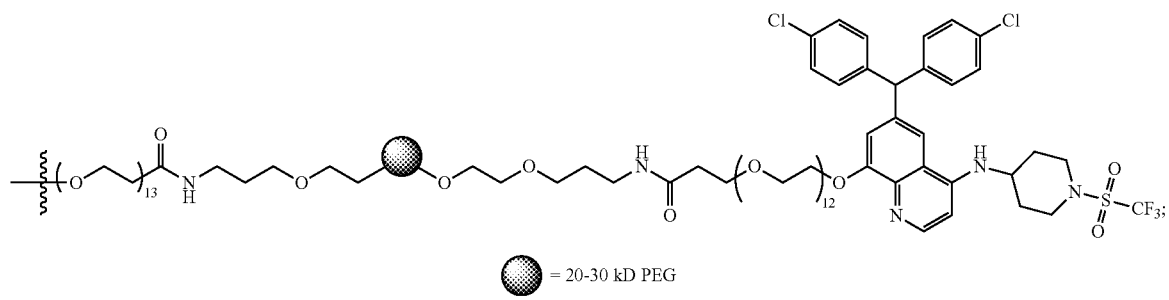
= 20-30 kD PEG
such that one of R₁ and R₂ is hydrogen in every instance;
R₃ is a substituent selected from the group consisting of methyl, carboxyethyl, aminoethyl, hydrogen, 4-hydroxymethylphenyl, or a substituent selected from the group consisting of
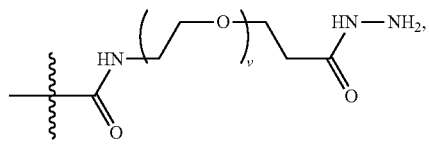  3a
-continued
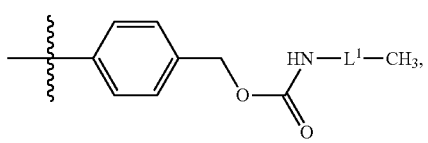  3b
wherein L¹ is
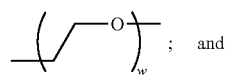  ; and -continued
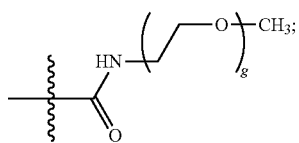
and
n is an integer from 3 to 12;
v is an integer from 5 to 12;
r is an integer from 2 to 5;
w is an integer from 1 to 12;
g is an integer from 1 to 12;
or an enantiomer, diastereomer, or pharmaceutically acceptable salt form thereof.
ii)
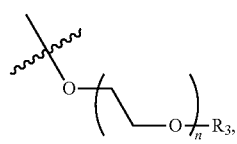
iii)
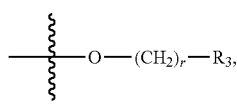
iv)
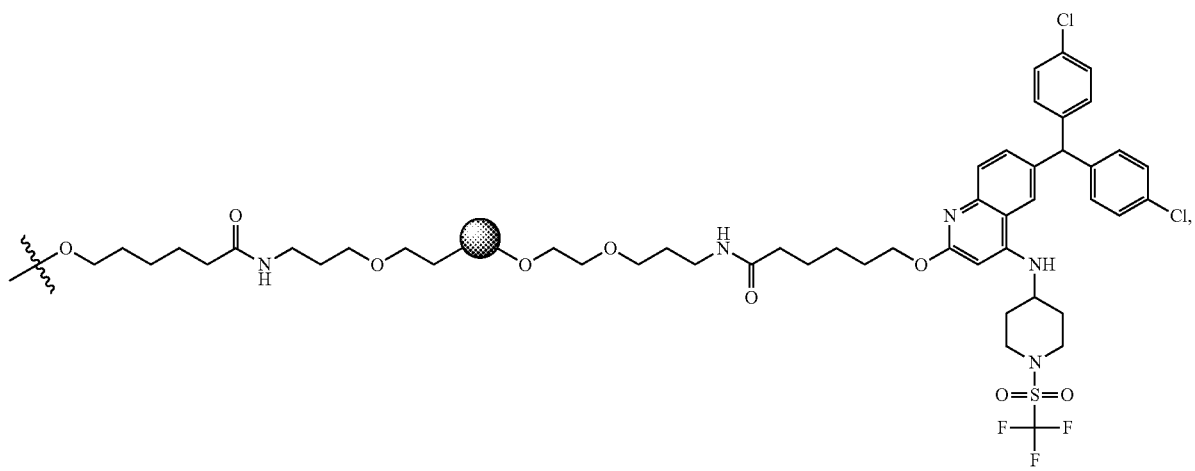
= 20 or 30 kD PEG
v)
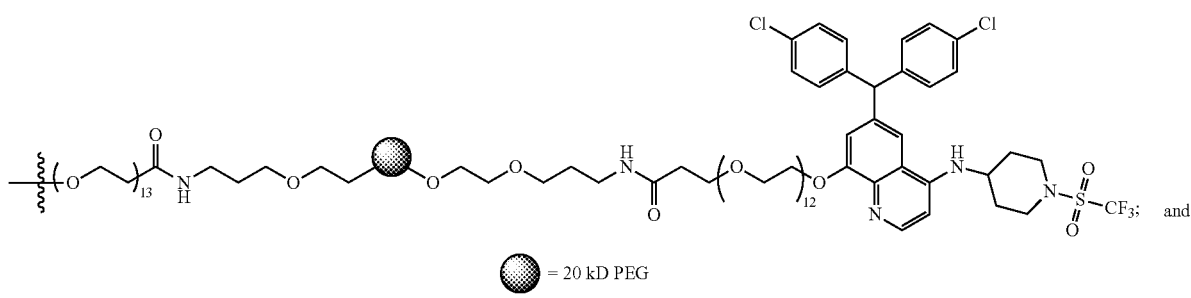
= 20 kD PEG
10. A compound of Formula (I)
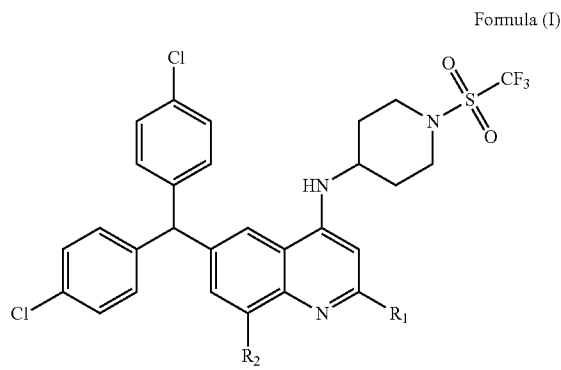
Formula (I)
wherein
$R_1$ and $R_2$ are selected from the group consisting of
i) hydrogen, vi)

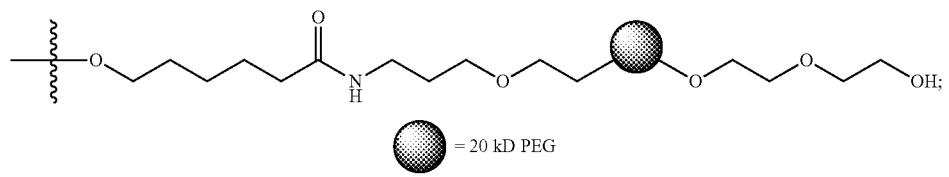

= 20 kD PEG $R_3$ is a substituent selected from the group consisting of hydrogen, methyl, t-butoxycarbonylamino-ethyl, t-butoxycarbonyl-ethyl, aminoethyl, carboxyethyl, 4-hydroxymethylphenyl, and a substituent selected from the group consisting of 3a
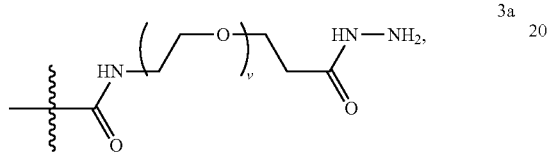

3b
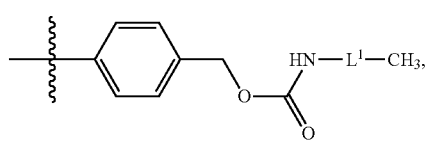

wherein $L^1$ is

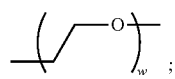

n is an integer selected from the group consisting of 3, 4, 6, 7, and 11;
v is 9 or 12;
r is 5;
w is 12;
g is 12;
or an enantiomer, diastereomer, or pharmaceutically acceptable salt form thereof.

11. A compound of Formula (II)

Formula (II)

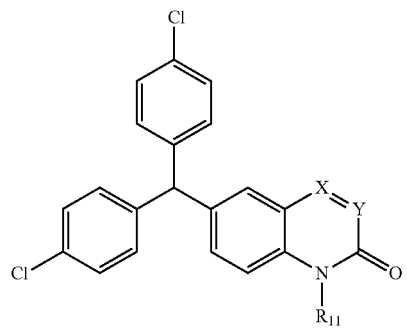

3c

[structure with (CH2)2-NH, benzamide, sulfonyl piperidine, quinazoline, bis(4-chlorophenyl)methyl]

Cl, and

3d

[structure HN-amide-(O-CH2CH2)g-CH3]

wherein
the group "X=Y" is

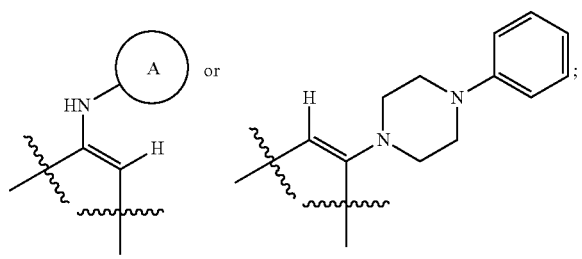

such that when X=Y is

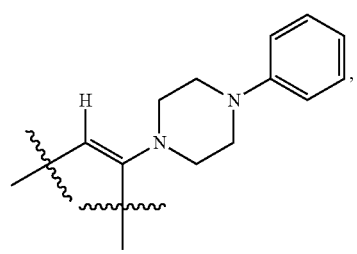 [SMILES: */C=C(\*)N1CCN(c2ccccc2)CC1]

$R_{11}$ is

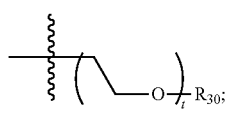

ring A is selected from

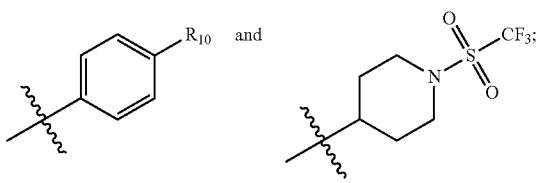

$R_{10}$ and $R_{11}$ are selected from the group consisting of hydrogen or

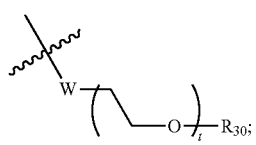

wherein W is O or absent; such that one of $R_{10}$ and $R_{11}$ is hydrogen in every instance where both $R_{10}$ and $R_{11}$ are present;
$R_{30}$ is a substituent selected from the group consisting of hydrogen, methyl, $C_{1-4}$alkoxycarbonylamino-ethyl, $C_{1-4}$alkoxycarbonyl-ethyl, carboxyethyl, aminoethyl, and 4-hydroxymethylphenyl;
t is an integer from 2 to 14;
or an enantiomer, diastereomer, or pharmaceutically acceptable salt form thereof.

12. The compound of claim 11 wherein the group "X=Y" is

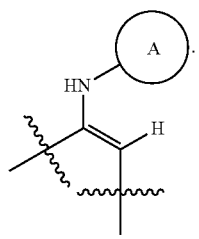

13. The compound of claim 11 wherein ring A is

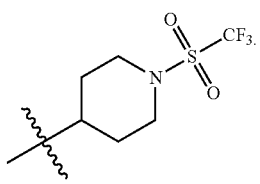 [SMILES: *C1CCN(S(=O)(=O)C(F)(F)F)CC1]

14. The compound of claim 13 wherein $R_{30}$ is a substituent selected from the group consisting of methyl and $C_{1-4}$alkoxycarbonylamino-ethyl.

15. The compound of claim 11 wherein t is an integer from 2 to 11.

16. A compound of Formula (II)

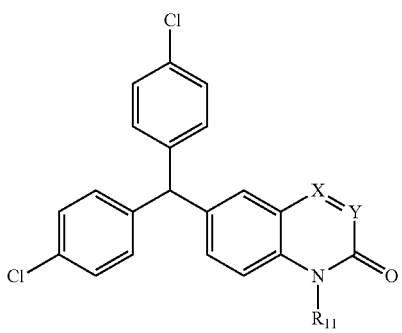

Formula (II)

wherein
the group "X=Y" is

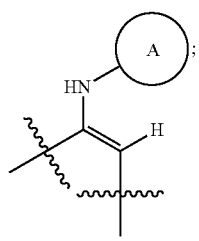

ring A is

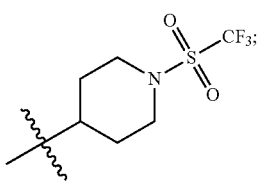 [SMILES: *C1CCN(S(=O)(=O)C(F)(F)F)CC1]

$R_{11}$ is
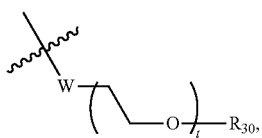
wherein W is absent;
$R_{30}$ is a substituent selected from the group consisting of methyl and $C_{1-4}$alkoxycarbonylamino-ethyl;
t is an integer from 2 to 11;
or an enantiomer, diastereomer, or pharmaceutically acceptable salt form thereof.
17. A compound selected from the group consisting of
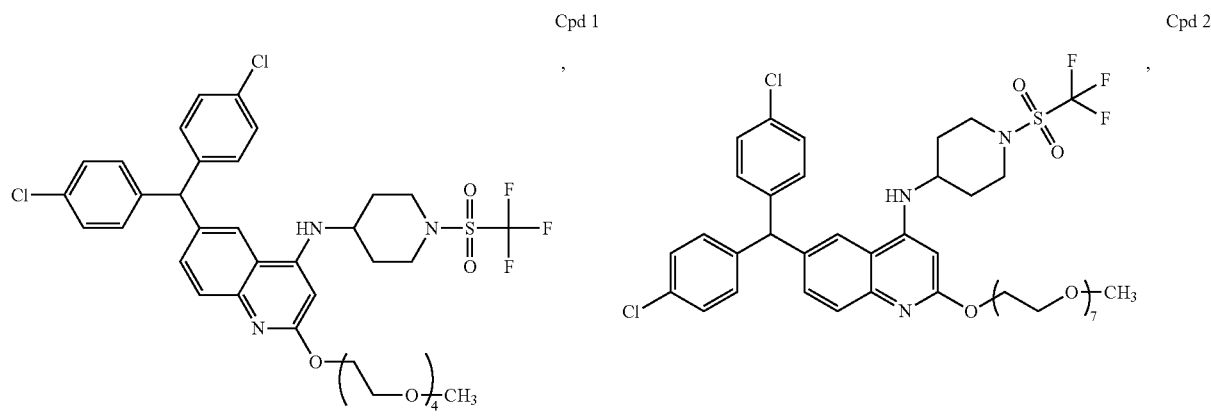
Cpd 1
Cpd 2
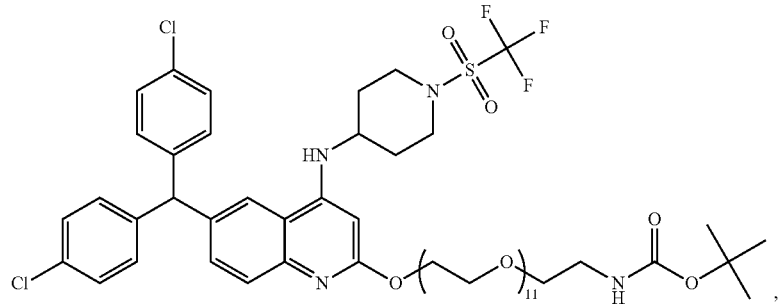
Cpd 3
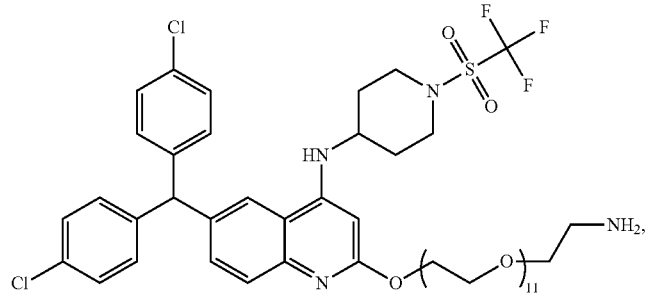
Cpd 4

-continued
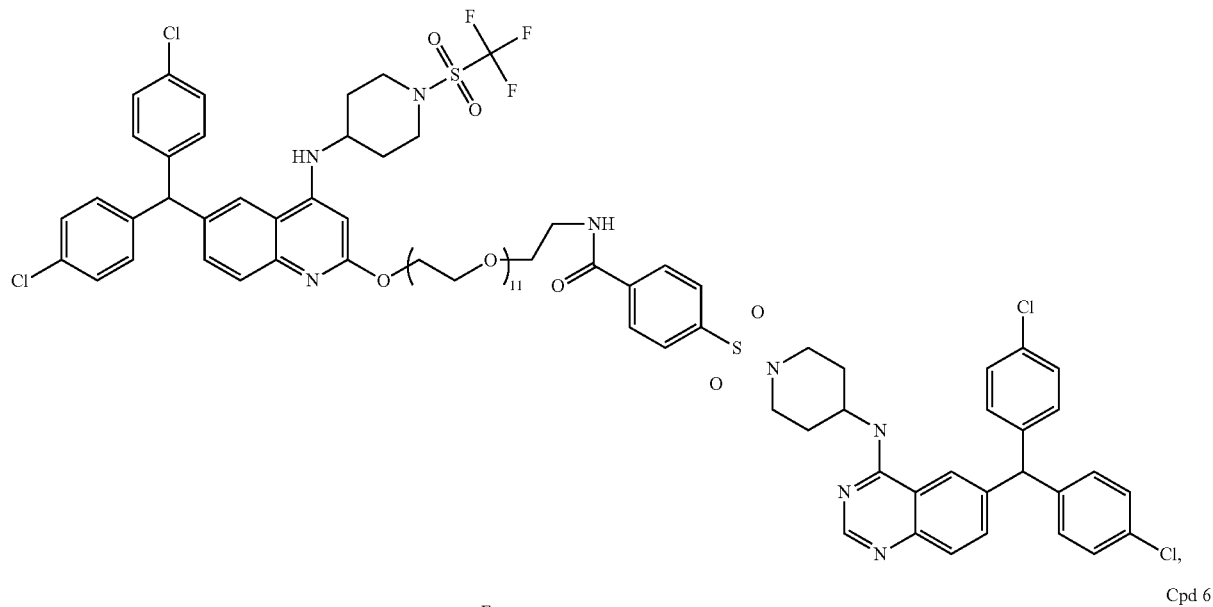
Cpd 5
Cpd 6
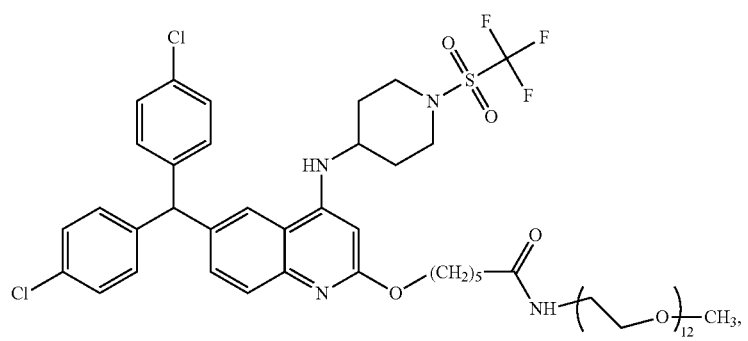
Cpd 7
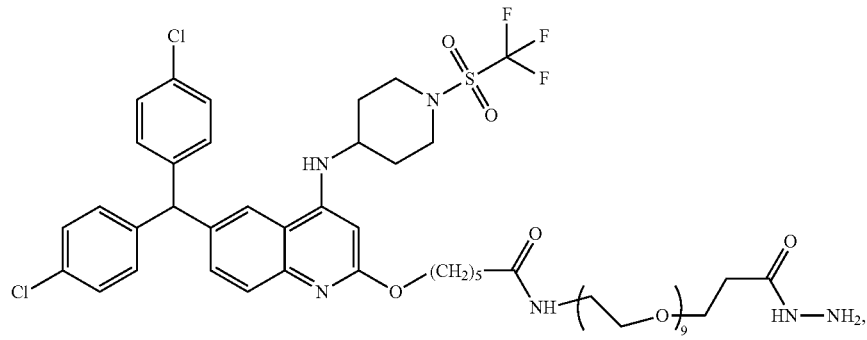
Cpd 8
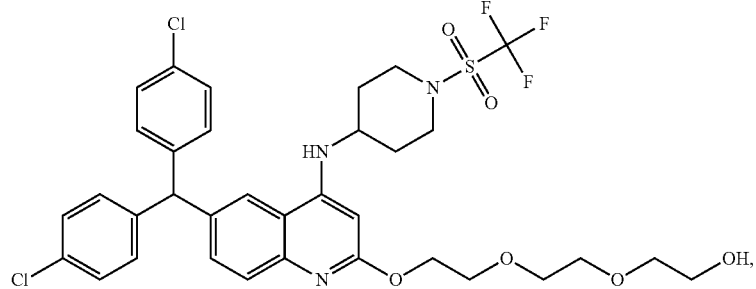

Cpd 9
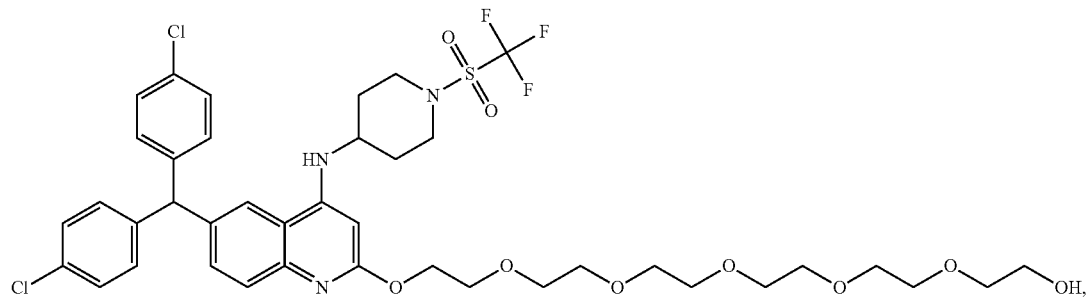
Cpd 10
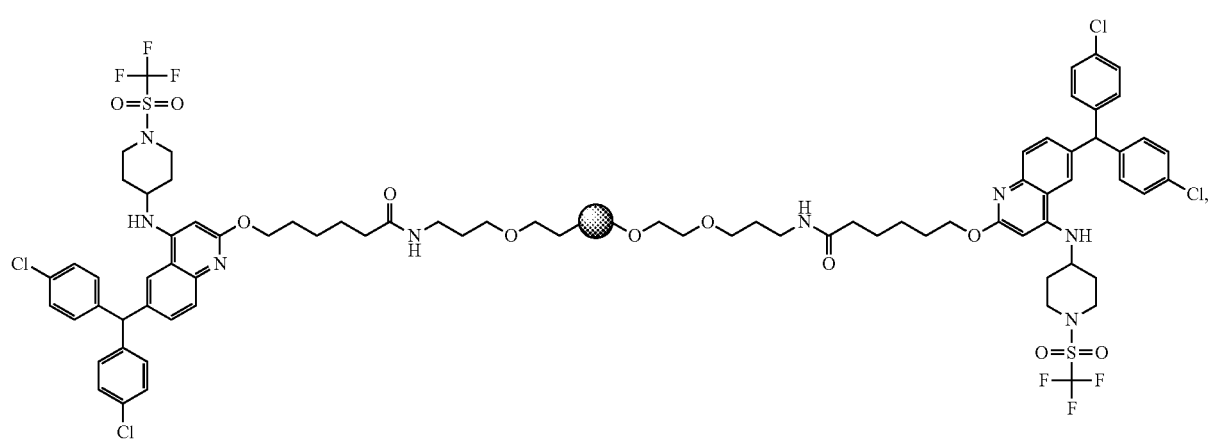
= 20 kD PEG
Cpd 11
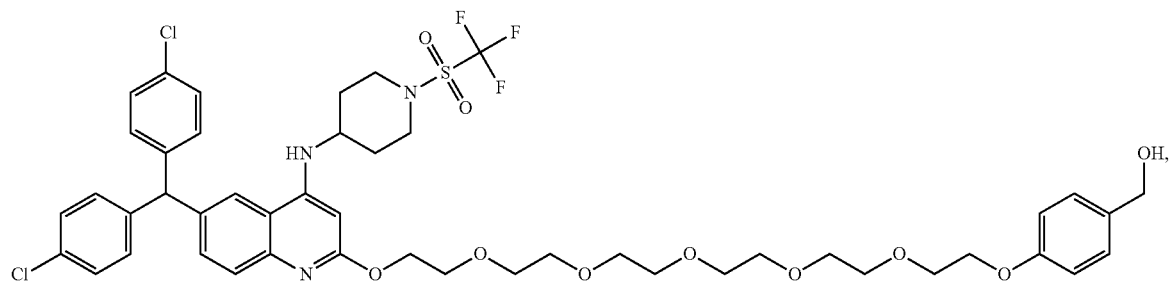
Cpd 12
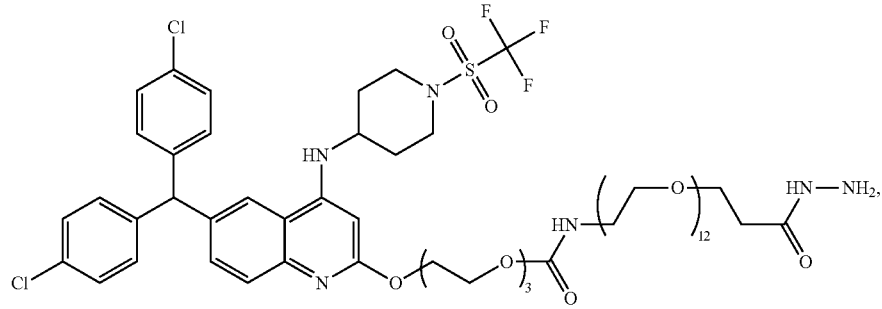

-continued
Cpd 13
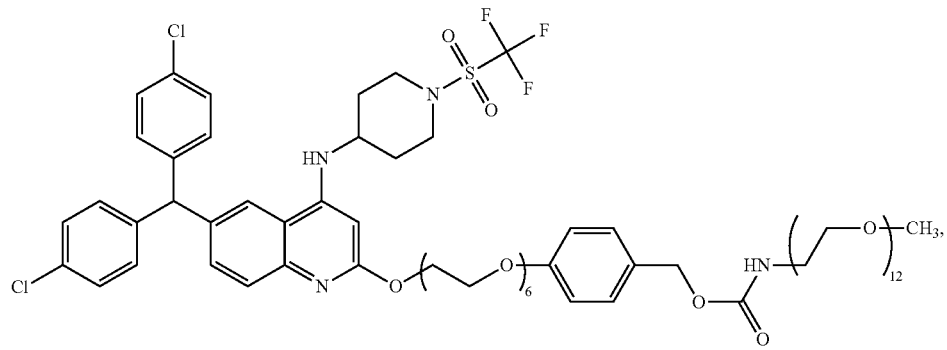
Cpd 14
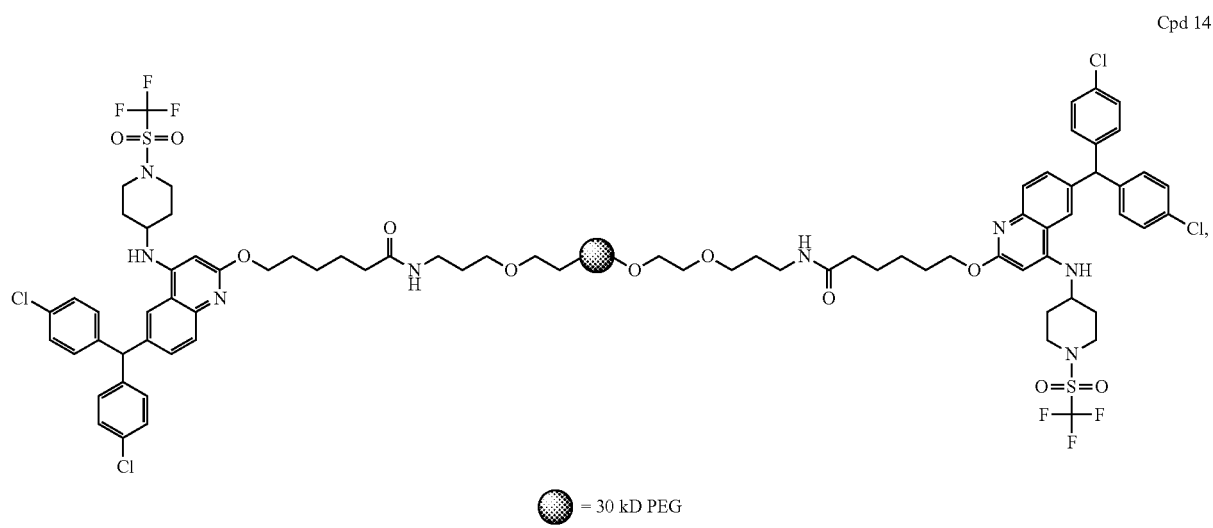
= 30 kD PEG
Cpd 15
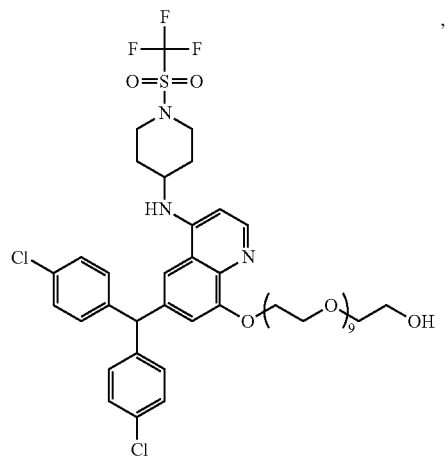
Cpd 16
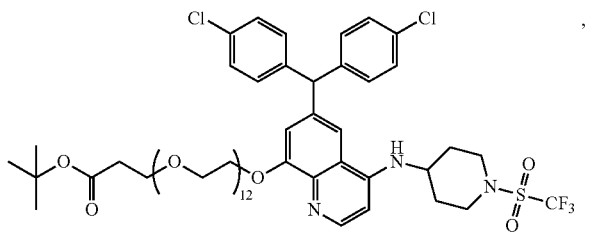

-continued
Cpd 17
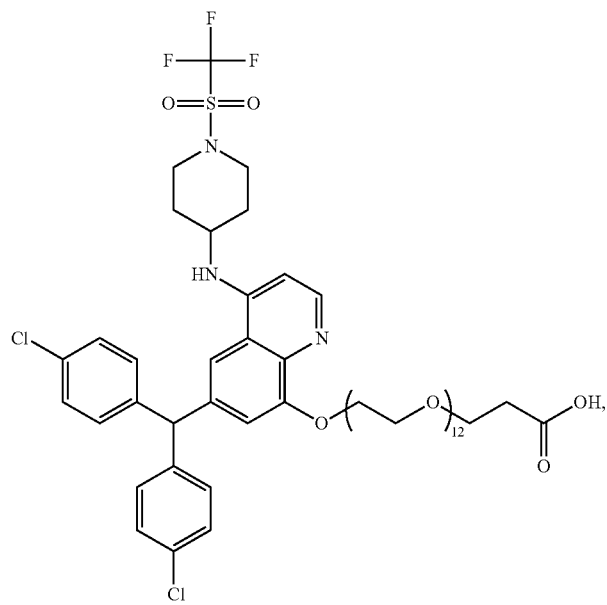
Cpd 18
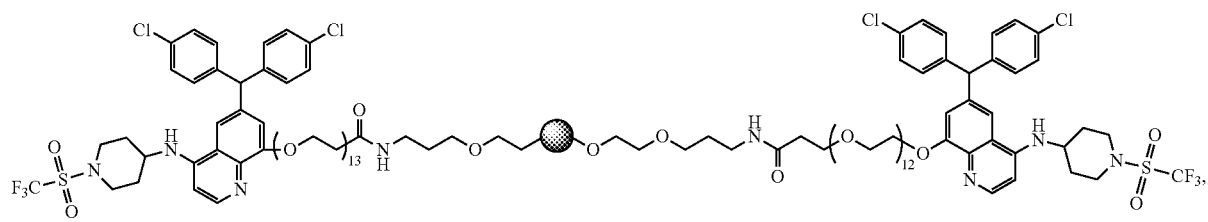
Cpd 19
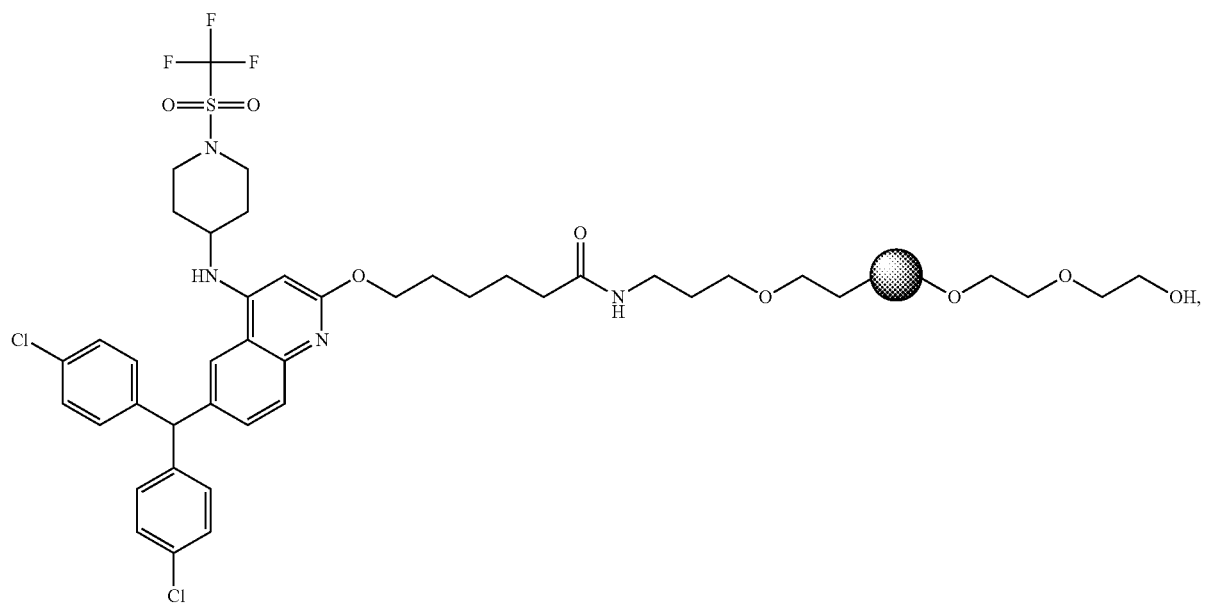

-continued
Cpd 20
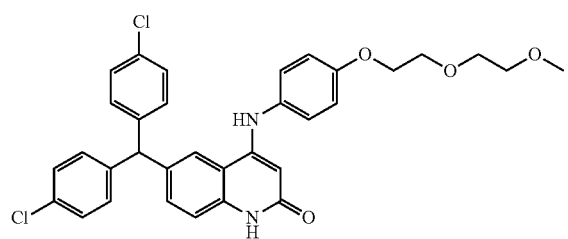
Cpd 21
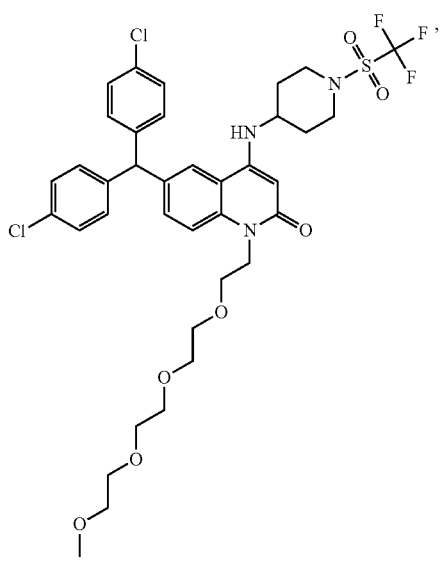
Cpd 22
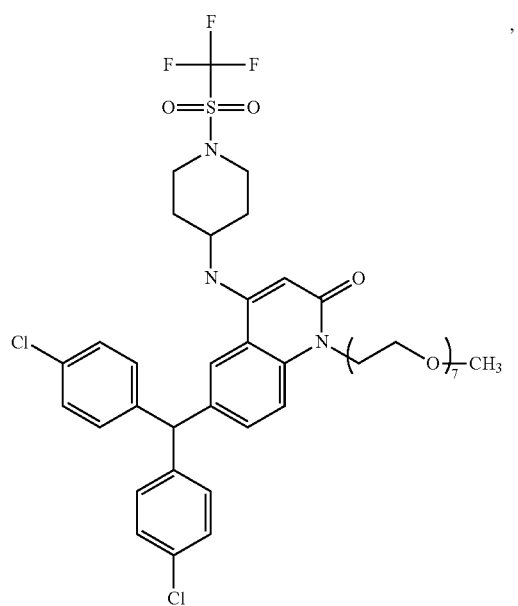
Cpd 23
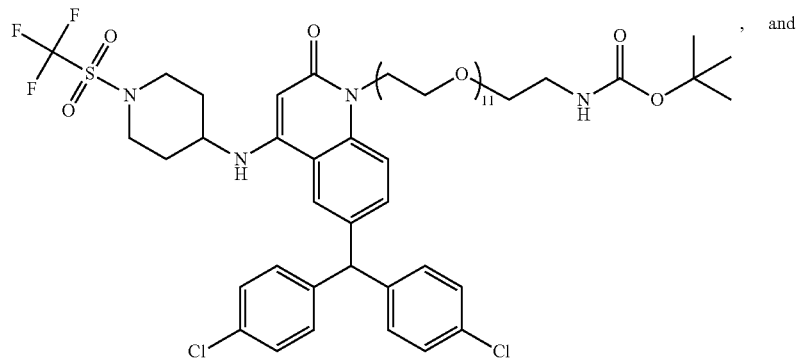
, and

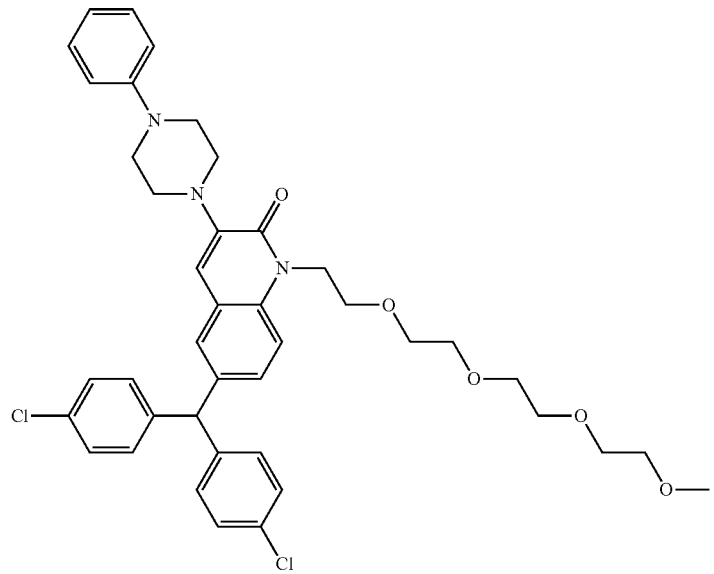

Cpd 24

18. A pharmaceutical composition comprising a compound of claim 1 or 11 and at least one of a pharmaceutically acceptable carrier, a pharmaceutically acceptable excipient, and a pharmaceutically acceptable diluent.

19. The pharmaceutical composition of claim 18, wherein the composition is a solid oral dosage form.

20. The pharmaceutical composition of claim 18, wherein the composition is a syrup, an elixir or a suspension.

21. A method of treating a disorder modulated by the CB1 receptor, comprising administering to a subject in need thereof a therapeutically effective amount of the compound of claim 1 or 11.

22. A method of treating a disorder, wherein said disorder is affected by the inverse agonism of the CB1 receptor, comprising administering to a subject in need thereof a therapeutically effective amount of the compound of claim 1 or 11.

23. The method of claim 22 wherein said disorder is selected from the group consisting of obesity, Type II diabetes mellitus, and Syndrome X.

24. A method of treating a disorder selected from the group consisting of obesity, Type II diabetes mellitus, and Syndrome X, comprising administering to a subject in need thereof a therapeutically effective amount of the composition of claim 18.

25. A method of treating a condition selected from the group consisting of obesity, Type II diabetes mellitus, and Syndrome X, comprising administering to a subject in need thereof, a therapeutically effective amount of a compound of claim 1 or 11.

26. A pharmaceutical composition comprising a compound of claim 17 and at least one of a pharmaceutically acceptable carrier, a pharmaceutically acceptable excipient, and a pharmaceutically acceptable diluent.

27. The pharmaceutical composition of claim 26, wherein the composition is a solid oral dosage form.

28. The pharmaceutical composition of claim 26, wherein the composition is a syrup, an elixir or a suspension.

29. A method of treating a disorder modulated by the CB1 receptor, comprising administering to a subject in need thereof a therapeutically effective amount of the compound of claim 17.

30. A method of treating a disorder, wherein said disorder is affected by the inverse agonism of the CB1 receptor, comprising administering to a subject in need thereof a therapeutically effective amount of the compound of claim 17.

31. The method of claim 30 wherein said disorder is selected from the group consisting of obesity, Type II diabetes mellitus, and Syndrome X.

32. A method of treating a disorder selected from the group consisting of obesity, Type II diabetes mellitus, and Syndrome X, comprising administering to a subject in need thereof a therapeutically effective amount of the composition of claim 26.

33. A method of treating a condition selected from the group consisting of obesity, Type II diabetes mellitus, and Syndrome X, comprising administering to a subject in need thereof, a therapeutically effective amount of a compound of claim 17.

* * * * *